US012582696B2

(12) United States Patent
Stappenbeck et al.

(10) Patent No.: US 12,582,696 B2
(45) Date of Patent: Mar. 24, 2026

(54) DEBARYOMYCES SPECIES AS AN INDICATOR OF NON-HEALING ULCERS IN CROHN'S DISEASE

(71) Applicant: Washington University, St. Louis, MO (US)

(72) Inventors: Thaddeus Stappenbeck, St. Louis, MO (US); Umang Jain, St. Louis, MO (US)

(73) Assignee: Washington University, St. Louis, MO (US)

( * ) Notice: Subject to any disclaimer, the term of this patent is extended or adjusted under 35 U.S.C. 154(b) by 924 days.

(21) Appl. No.: 17/784,589

(22) PCT Filed: Dec. 10, 2020

(86) PCT No.: PCT/US2020/064376
§ 371 (c)(1),
(2) Date: Jun. 10, 2022

(87) PCT Pub. No.: WO2021/119358
PCT Pub. Date: Jun. 17, 2021

(65) Prior Publication Data
US 2023/0218713 A1      Jul. 13, 2023

Related U.S. Application Data

(60) Provisional application No. 62/946,427, filed on Dec. 10, 2019.

(51) Int. Cl.
| | |
|---|---|
| *A61K 38/12* | (2006.01) |
| *A61K 31/4196* | (2006.01) |
| *A61K 31/513* | (2006.01) |
| *A61P 1/04* | (2006.01) |
| *A61P 31/10* | (2006.01) |

(52) U.S. Cl.
CPC .......... *A61K 38/12* (2013.01); *A61K 31/4196* (2013.01); *A61K 31/513* (2013.01); *A61P 1/04* (2018.01); *A61P 31/10* (2018.01)

(58) Field of Classification Search
CPC .. A61K 38/12; A61K 31/4196; A61K 31/513; A61P 1/04; A61P 31/10
See application file for complete search history.

(56) References Cited

U.S. PATENT DOCUMENTS

| | | |
|---|---|---|
| 2011/0195094 A1 | 8/2011 | Ying et al. |
| 2018/0050034 A1* | 2/2018 | Gerbe .................... A61K 45/06 |
| 2019/0307843 A1 | 10/2019 | Bartizal et al. |

FOREIGN PATENT DOCUMENTS

| | | | |
|---|---|---|---|
| WO | WO-2018085200 A1 * | 5/2018 | ............. A61P 31/10 |
| WO | 2018102407 A1 | 6/2018 | |
| WO | 2019126556 A2 | 6/2019 | |
| WO | 2019173763 A1 | 9/2019 | |

OTHER PUBLICATIONS

Sokol et al, Fungal microbiota dysbiosis in IBD, Gut, 2017, 66, pp. 1039-1048.*
Liguori et al, Fungal Dysbiosis in Mucosa-associated Microbiota of Crohn's Disease Patients, Journal of Crohn's and Colitis, 2016, pp. 296-305.*
Beyda et al, Treatment of Candida famata bloodstream infections: case series and review of the literature, J Antimicrob Chemother, 2013, 68, pp. 438-443.*
Extended European Search Report for European Application No. 20899977.1, mailed Oct. 17, 2023, 09 Pages.
International Search Report and Written Opinion for International Application No. PCT/US2020/064376, mailed May 20, 2021, 11 Pages.
Irwin et al., Zinc—a free database of commercially available compounds for virtual screening. J Chem Inf Model. Jan.-Feb. 2005; 45(1):177-82.
Koda-Kimble et al., Applied Therapeutics: The Clinical Use of Drugs, Lippincott Williams & Wilkins, 2013. TOC only. 41 pages.
Lipinski et al., Drug-like properties and the causes of poor solubility and poor permeability. J Pharmacol Toxicol Methods. Jul.-Aug. 2000; 44(1):235-49.
Sharqel. Applied Biopharmaceutics & Pharmacokinetics, McGraw-Hill/Appleton & Lange, ISBN 0071375503. 2012. TOC only. 3 pages.
Uchegbu and Schatzlein. Polymers in Drug Delivery, CRC, ISBN—10: 0849325331. 2006. TOC only. 3 pages.

* cited by examiner

*Primary Examiner* — Li N Komatsu
(74) *Attorney, Agent, or Firm* — Jason R. Bond; Casimir Jones, S.C.

(57) ABSTRACT

Methods for treating, selecting a treatment, and monitoring a treatment for an inflammatory bowel disease in a patient in need are disclosed. Treatments include administering an antifungal compound. The method for selecting and monitoring a treatment includes detecting a biomarker indicative of an amount of the fungus *Debaryomyces hansenii* within the sample. The treatment is administered if the biomarker is above a threshold level and the biomarker may be monitored before and during treatment. Biomarkers include abundance of fungal DNA in the patient's gut microbiota and anti-fungal antibodies in the blood of the patient.

5 Claims, 54 Drawing Sheets

Specification includes a Sequence Listing.

ANTIMICROBICS

| | |
|---|---|
| POS | Positive Control |
| AND | Anidulafungin |
| AB | Amphotericin B |
| MF | Micafungin |
| CAS | Caspofungin |
| FC | 5-Flucytosine |
| PZ | Posaconazole |
| VOR | Voriconazole |
| IZ | Itraconazole |
| FZ | Fluconazole |

SENSITITRE™ YEASTONE™ PLATE FORMAT

Plate Code: YO9

| | 1 | 2 | 3 | 4 | 5 | 6 | 7 | 8 | 9 | 10 | 11 | 12 |
|---|---|---|---|---|---|---|---|---|---|---|---|---|
| A | POS | AND 0.015 | AND 0.03 | AND 0.06 | AND 0.12 | AND 0.25 | AND 0.5 | AND 1 | AND 2 | AND 4 | AND 8 | AB 0.12 |
| B | MF 0.008 | MF 0.015 | MF 0.03 | MF 0.06 | MF 0.12 | MF 0.25 | MF 0.5 | MF 1 | MF 2 | MF 4 | MF 8 | AB 0.25 |
| C | CAS 0.008 | CAS 0.015 | CAS 0.03 | CAS 0.06 | CAS 0.12 | CAS 0.25 | CAS 0.5 | CAS 1 | CAS 2 | CAS 4 | CAS 8 | AB 0.5 |
| D | FC 0.06 | FC 0.12 | FC 0.25 | FC 0.5 | FC 1 | FC 2 | FC 4 | FC 8 | FC 16 | FC 32 | FC 64 | AB 1 |
| E | PZ 0.008 | PZ 0.015 | PZ 0.03 | PZ 0.06 | PZ 0.12 | PZ 0.25 | PZ 0.5 | PZ 1 | PZ 2 | PZ 4 | PZ 8 | AB 2 |
| F | VOR 0.008 | VOR 0.015 | VOR 0.03 | VOR 0.06 | VOR 0.12 | VOR 0.25 | VOR 0.5 | VOR 1 | VOR 2 | VOR 4 | VOR 8 | AB 4 |
| G | IZ 0.015 | IZ 0.03 | IZ 0.06 | IZ 0.12 | IZ 0.25 | IZ 0.5 | IZ 1 | IZ 2 | IZ 4 | IZ 8 | IZ 16 | AB 8 |
| H | FZ 0.12 | FZ 0.25 | FZ 0.5 | FZ 1 | FZ 2 | FZ 4 | FZ 8 | FZ 16 | FZ 32 | FZ 64 | FZ 128 | FZ 256 |

FIG. 5B

Identification in Crohn's     Isolation and Culture     Introduction in mice leads to worsened phenotype     Re-isolation from the diseased mice

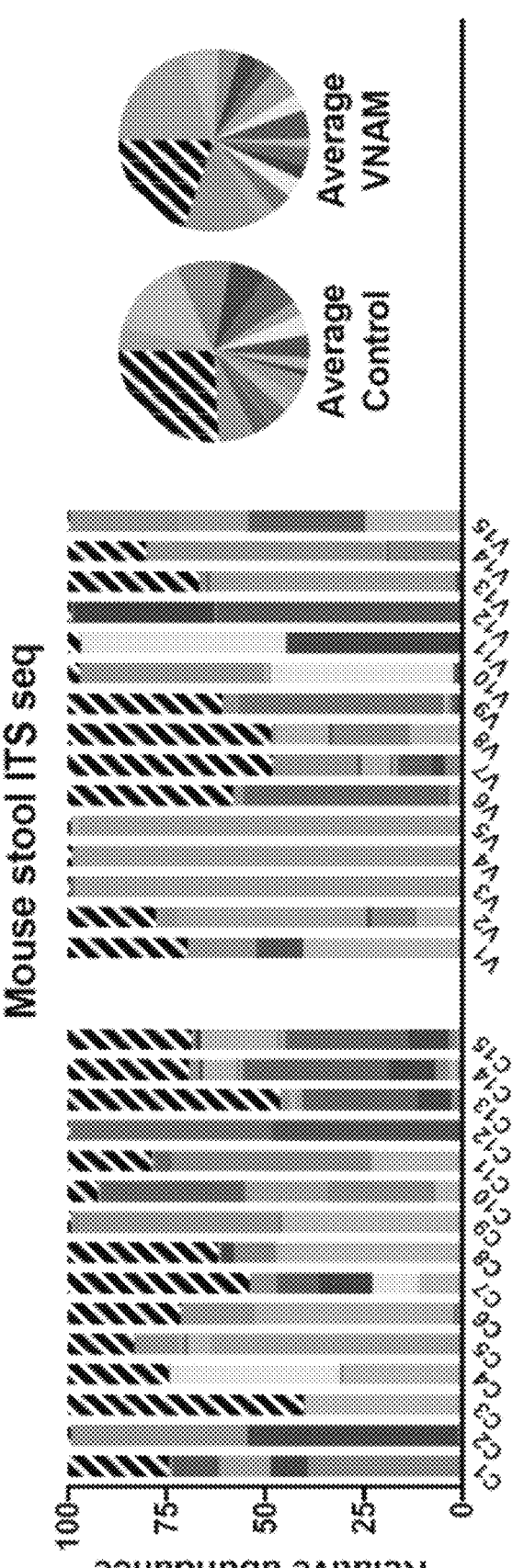
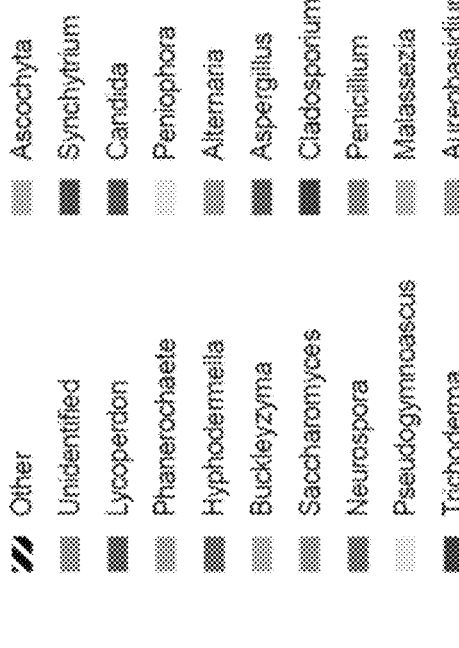
FIG. 14

```
Q 1     ACCAAGGTATCATGGTCGGTATGGGACAAAAGGACTCTTATGTTGGGGATGAAGCCCAAT
        ||||||||||||||||||||||||||||||||||||||||||||||||||||||||||||
S 24    ACCAAGGTATCATGGTCGGTATGGGACAAAAGGACTCTTATGTTGGGGATGAAGCCCAAT

Q 61    CCAAGAGAGGTATCTTGACCTTGAGATACCCTATCGAACACGGTATTGTCACCAACTGGG
        ||||||||||||||||||||||||||||||||||||||||||||||||||||||||||||
S 84    CCAAGAGAGGTATCTTGACCTTGAGATACCCTATCGAACACGGTATTGTCACCAACTGGG

Q 121   ACGATATGGAAAAGATCTGGCATCACACCTTCTACAACGAATTGAGAGTTGCCCCAGAAG
        ||||||||||||||||||||||||||||||||||||||||||||||||||||||||||||
S 144   ACGATATGGAAAAGATCTGGCATCACACCTTCTACAACGAATTGAGAGTTGCCCCAGAAG

Q 181   AACACCCAGTTTTGTTGACCGAAGCCCCAATGAACCCTAAATCTAACCGTGAAAAGATGA
        ||||||||||||||||||||||||||||||||||||||||||||||||||||||||||||
S 204   AACACCCAGTTTTGTTGACCGAAGCCCCAATGAACCCTAAATCTAACCGTGAAAAGATGA

Q 241   CCCAAATCATGTTTGAAACCTTCAACGTACCAGCCTTCTACGTTTCTATTCAAGCCGTCT
        ||||||||||||||||||||||||||||||||||||||||||||||||||||||||||||
S 264   CCCAAATCATGTTTGAAACCTTCAACGTACCAGCCTTCTACGTTTCTATTCAAGCCGTCT

Q 301   TATCTTTATACTCGTCTGGTAGAACCACCGGTATCGTTTTAGATTCGGGTGATGGTGTTA
        ||||||||||||||||||||||||||||||||||||||||||||||||||||||||||||
S 324   TATCTTTATACTCGTCTGGTAGAACCACCGGTATCGTTTTAGATTCGGGTGATGGTGTTA

Q 361   CTCACGTTGTTCCAATTTACGCCGGTTTCTCCTTACCACACGGTATCTTAAGAATTGACT
        ||||||||||||||||||||||||||||||||||||||||||||||||||||||||||||
S 384   CTCACGTTGTTCCAATTTACGCCGGTTTCTCCTTACCACACGGTATCTTAAGAATTGACT

Q 421   TGGCTGGTAGAGACTTGACCGACTACTTGATGAAGATCTTGTCCGAAAGAGGTTACACTT
        ||||||||||||||||||||||||||||||||||||||||||||||||||||||||||||
S 444   TGGCTGGTAGAGACTTGACCGACTACTTGATGAAGATCTTGTCCGAAAGAGGTTACACTT

Q 481   TCTCCACCACCGCTGAAAGAGAAATTGTCCGTGATATCAAAGAAAAATTATGTTATGTTG
        ||||||||||||||||||||||||||||||||||||||||||||||||||||||||||||
S 504   TCTCCACCACCGCTGAAAGAGAAATTGTCCGTGATATCAAAGAAAAATTATGTTATGTTG

Q 541   CCTTGGACTTTGAACAAGAAATGCAAACTTCATCTCAATCCTCCGCCATCGAAAAGTCTT
        ||||||||||||||||||||||||||||||||||||||||||||||||||||||||||||
S 564   CCTTGGACTTTGAACAAGAAATGCAAACTTCATCTCAATCCTCCGCCATCGAAAAGTCTT

Q 601   ACGAATTACCTGATGGTCAAGTTATTACTATCGGTAACGAAAGATTTAGAGCTTCCGAAG
        ||||||||||||||||||||||||||||||||||||||||||||||||||||||||||||
S 624   ACGAATTACCTGATGGTCAAGTTATTACTATCGGTAACGAAAGATTTAGAGCTTCCGAAG

Q 661   CTTTGTTCCGTCCTTCTGACTTAGGTTTAGAAGCCGCTGGTATTGACCAAACCACTTACA
        ||||||||||||||||||||||||||||||||||||||||||||||||||||||||||||
S 684   CTTTGTTCCGTCCTTCTGACTTAGGTTTAGAAGCCGCTGGTATTGACCAAACCACTTACA

Q 721   ACTCGATTATGAAGTGTGATGTCGATGTCAGAAAGGAATTATACGGTAACATTGTTATGT
        ||||||||||||||||||||||||||||||||||||||||||||||||||||||||||||
S 744   ACTCGATTATGAAGTGTGATGTCGATGTCAGAAAGGAATTATACGGTAACATTGTTATGT

Q 781   CTGGTGGTACCACCATGTTCCCTGGTAT (SEQ ID NO:1)
        |||||||||||||||||||||||||||
S 804   CTGGTGGTACCACCATGTTCCCTGGTAT (SEQ ID NO:2)
```

FIG. 15

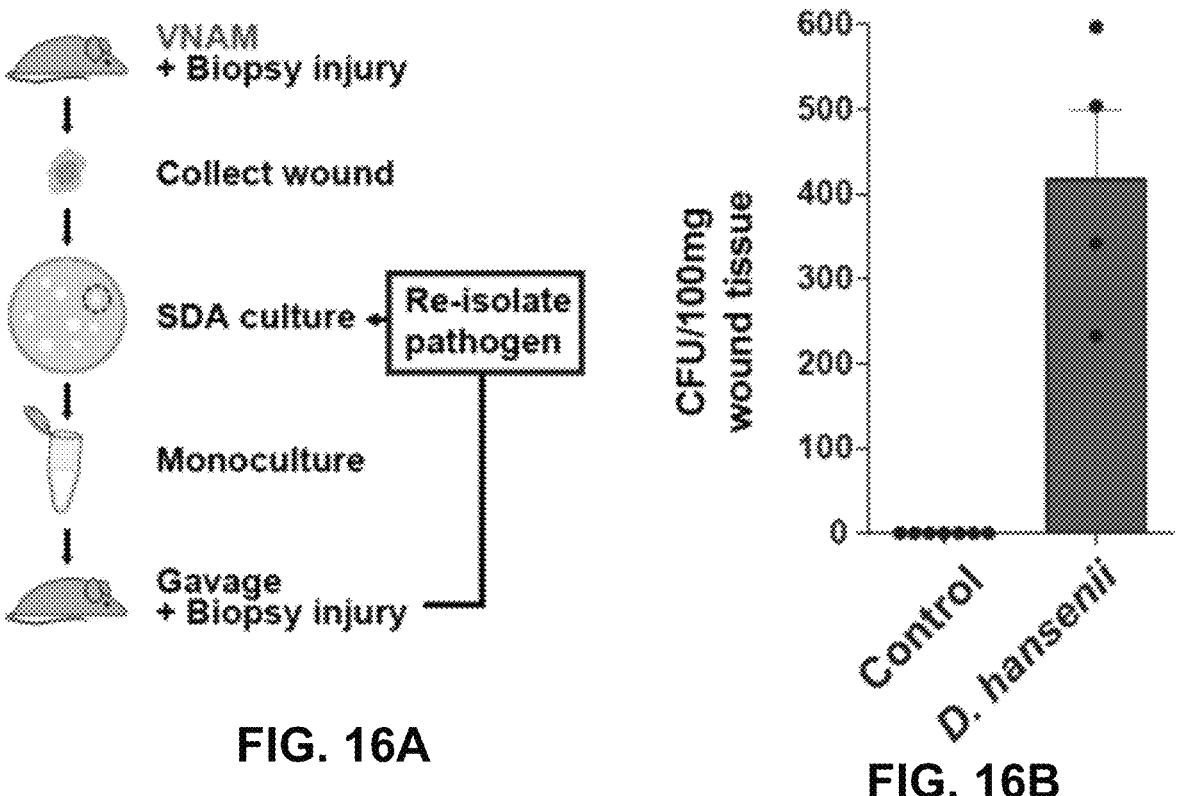
FIG. 16A
FIG. 16B
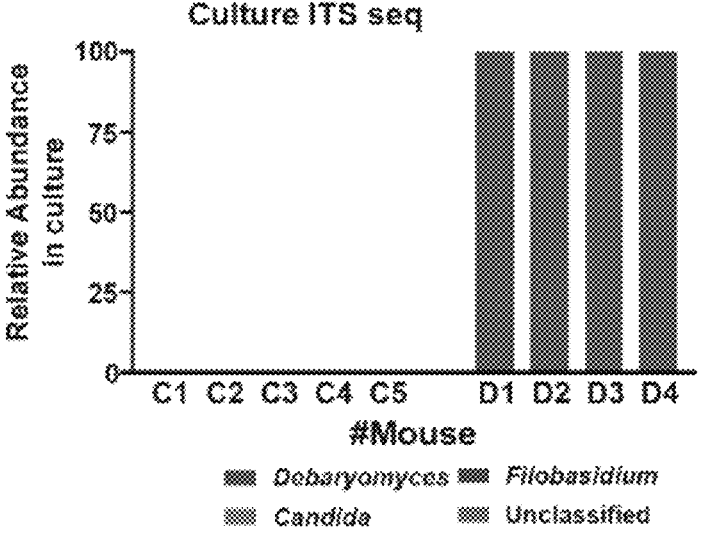
FIG. 16C

Day 8 Wound lysate

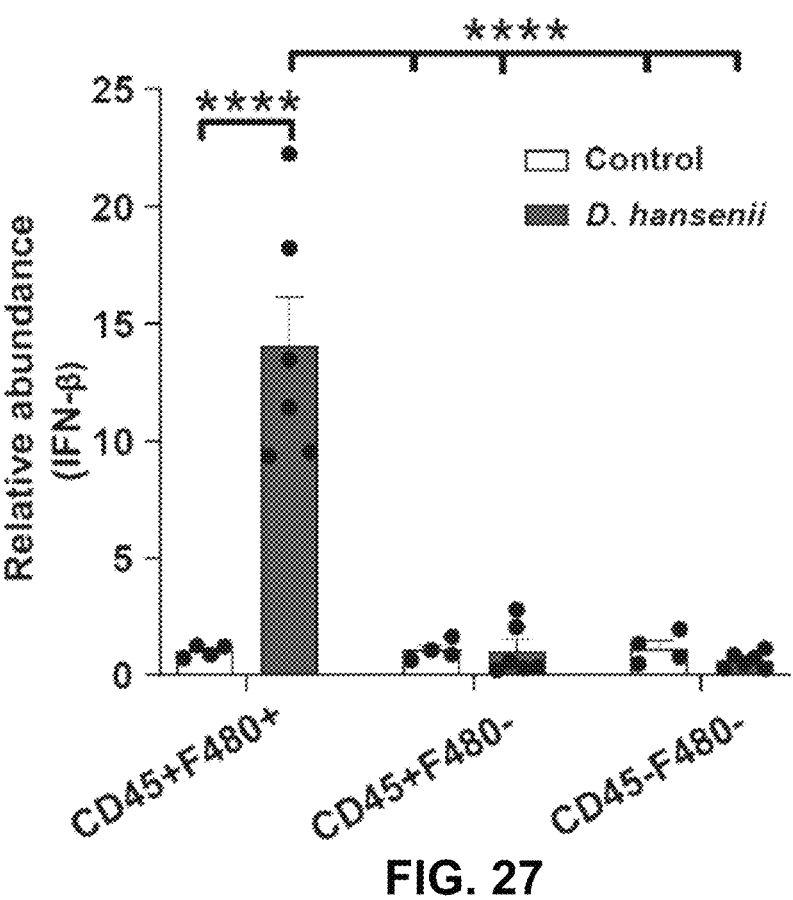
FIG. 27
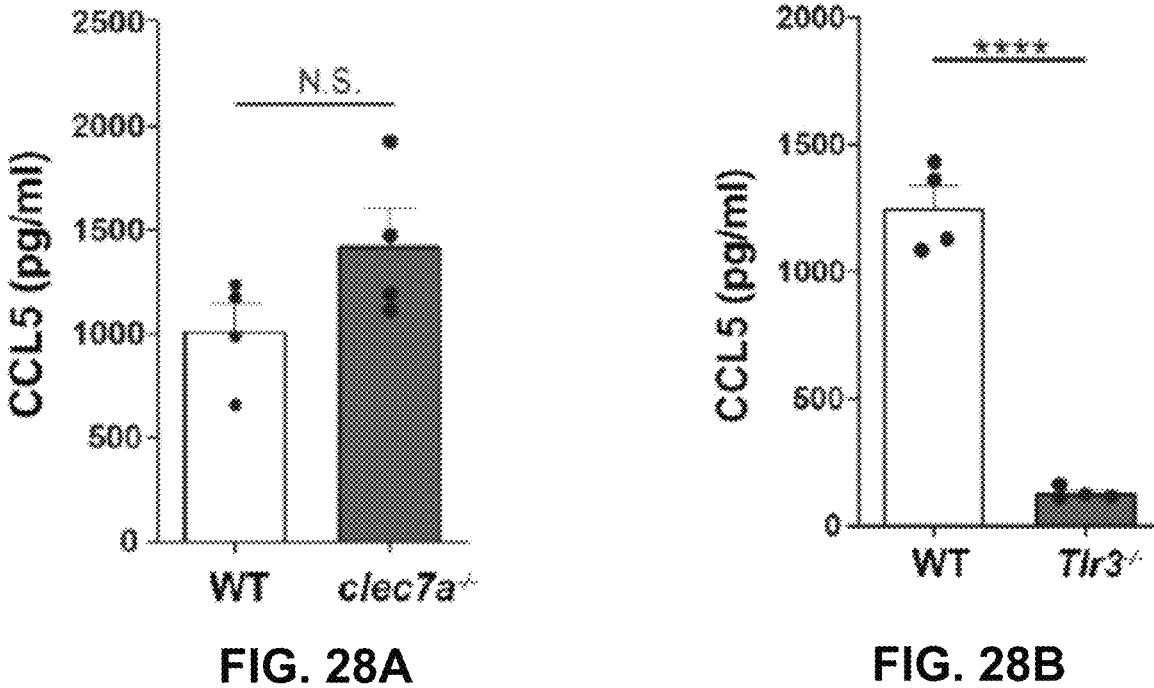
FIG. 28A                      FIG. 28B

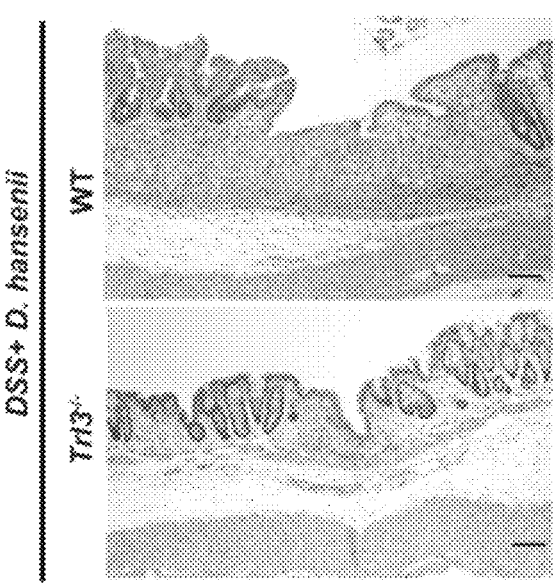
FIG. 28C
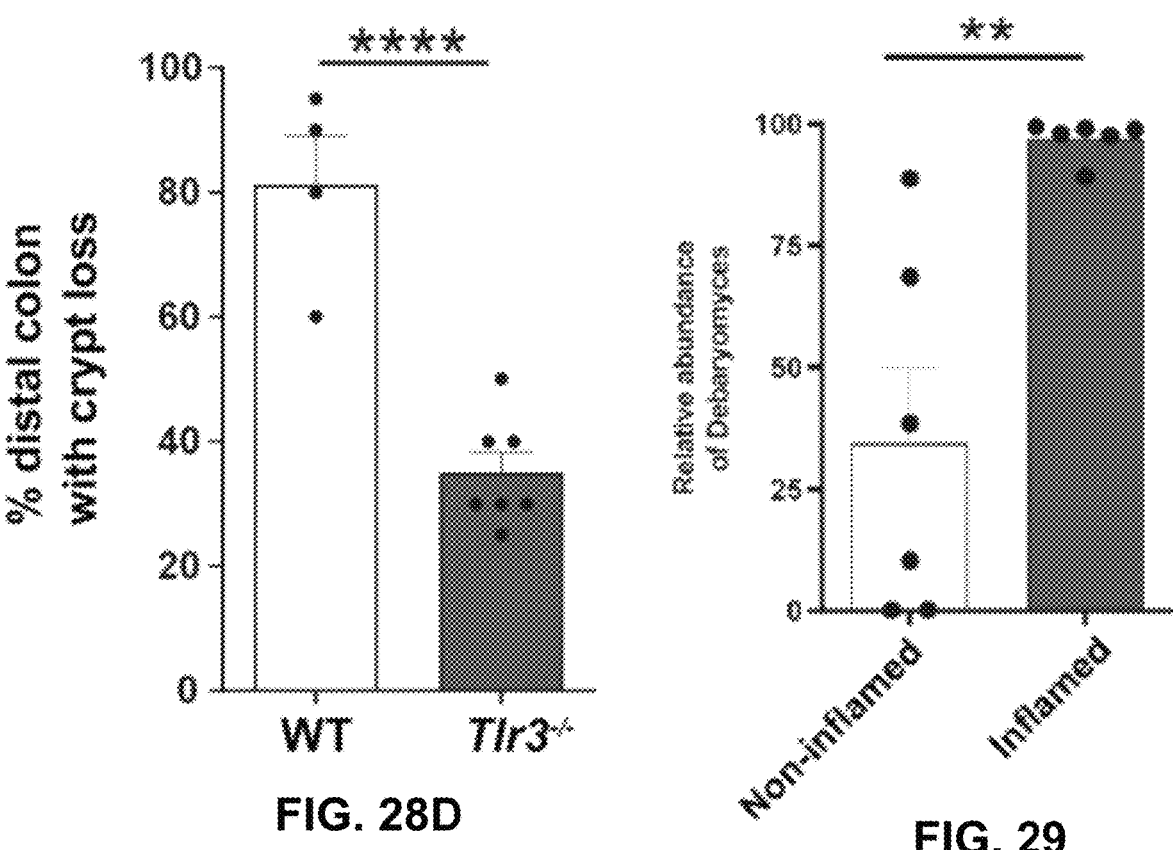
FIG. 28D
FIG. 29

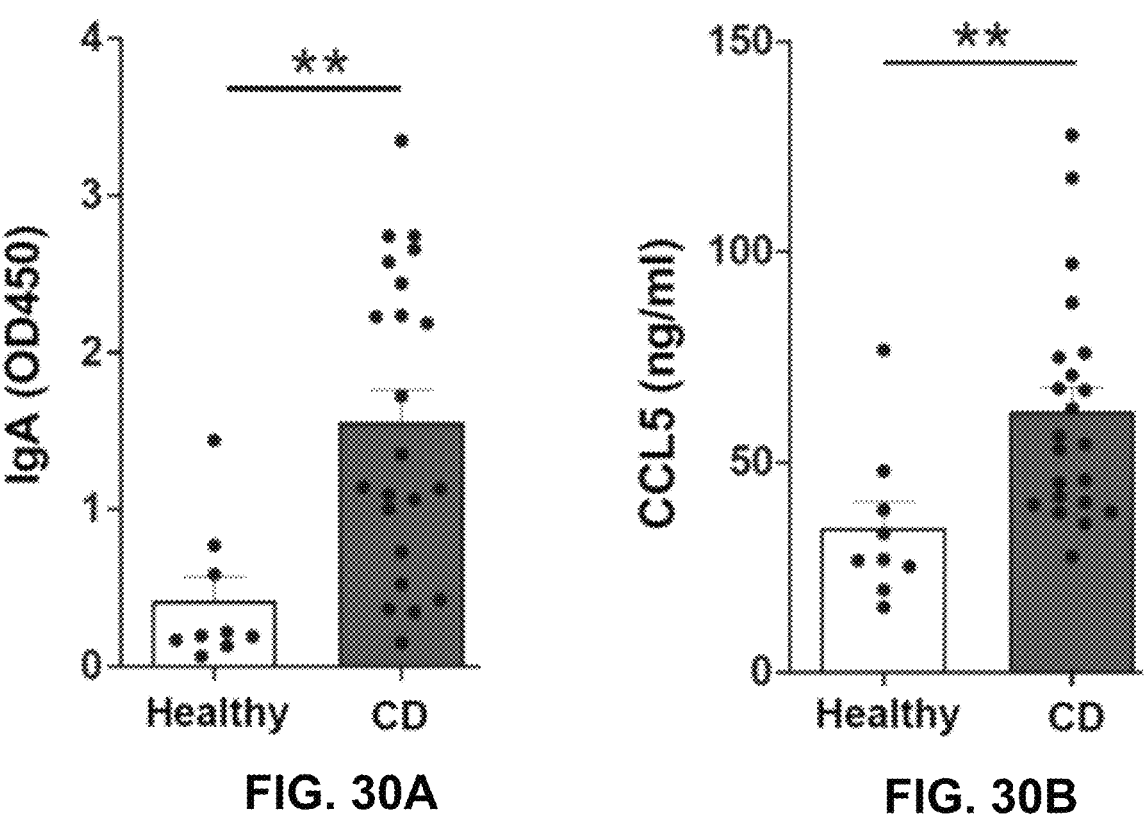
FIG. 30A
FIG. 30B
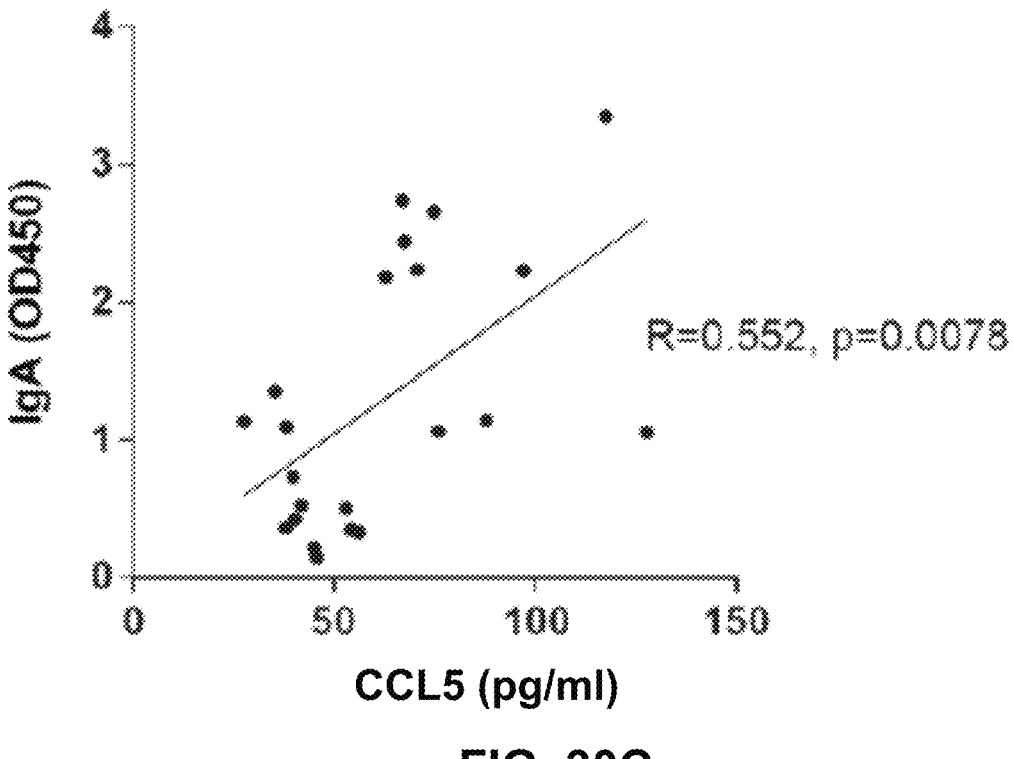
FIG. 30C

Mouse XL Cytokine Array
Transparency Overlay

| Coordinate | Analyte/Control |
| --- | --- |
| A1, A2 | Reference Spots |
| A3, A4 | Adiponectin/Acrp30 |
| A5, A6 | Amphiregulin |
| A7, A8 | Angiopoietin-1 |
| A9, A10 | Angiopoietin-2 |
| A11, A12 | Angiopoietin-like 3 |
| A13, A14 | BAFF/BLyS/TNFSF13B |
| A15, A16 | C1q R1/CD93 |
| A17, A18 | CCL2/JE/MCP-1 |
| A19, A20 | CCL3/CCL4/MIP-1α/β |
| A21, A22 | CCL5/RANTES |
| A23, A24 | Reference Spots |
| B3, B4 | CCL6/C10 |
| B5, B6 | CCL11/Eotaxin |
| B7, B8 | CCL12/MCP-5 |
| B9, B10 | CCL17/TARC |
| B11, B12 | CCL19/MIP-3β |
| B13, B14 | CCL20/MIP-3α |
| B15, B16 | CCL21/6Ckine |
| B17, B18 | CCL22/MDC |
| B19, B20 | CD14 |
| B21, B22 | CD40/TNFRSF5 |
| C3, C4 | CD160 |
| C5, C6 | Chemerin |
| C7, C8 | Chitinase 3-like 1 |
| C9, C10 | Coagulation Factor III/Tissue Factor |
| C11, C12 | Complement Component C5/C5a |
| C13, C14 | Complement Factor D |
| C15, C16 | C-Reactive Protein/CRP |
| C17, C18 | CX3CL1/Fractalkine |
| C19, C20 | CXCL1/KC |
| C21, C22 | CXCL2/MIP-2 |
| D1, D2 | CXCL9/MIG |
| D3, D4 | CXCL10/IP-10 |
| D5, D6 | CXCL11/I-TAC |
| D7, D8 | CXCL13/BLC/BCA-1 |
| D9, D10 | CXCL16 |
| D11, D12 | Cystatin C |

| Coordinate | Analyte/Control |
| --- | --- |
| D13, D14 | DKK-1 |
| D15, D16 | DPPIV/CD26 |
| D17, D18 | EGF |
| D19, D20 | Endoglin/CD105 |
| D21, D22 | Endostatin |
| D23, D24 | Fetuin A/AHSG |
| E1, E2 | FGF acidic |
| E3, E4 | FGF-21 |
| E5, E6 | Flt-3 Ligand |
| E7, E8 | Gas 6 |
| E9, E10 | G-CSF |
| E11, E12 | GDF-15 |
| E13, E14 | GM-CSF |
| E15, E16 | HGF |
| E17, E18 | ICAM-1/CD54 |
| E19, E20 | IFN-γ |
| E21, E22 | IGFBP-1 |
| E23, E24 | IGFBP-2 |
| F1, F2 | IGFBP-3 |
| F3, F4 | IGFBP-5 |
| F5, F6 | IGFBP-6 |
| F7, F8 | IL-1α/IL-1F1 |
| F9, F10 | IL-1β/IL-1F2 |
| F11, F12 | IL-1ra/IL-1F3 |
| F13, F14 | IL-2 |
| F15, F16 | IL-3 |
| F17, F18 | IL-4 |
| F19, F20 | IL-5 |
| F21, F22 | IL-6 |
| F23, F24 | IL-7 |
| G1, G2 | IL-10 |
| G3, G4 | IL-11 |
| G5, G6 | IL-12 p40 |
| G7, G8 | IL-13 |
| G9, G10 | IL-15 |
| G11, G12 | IL-17A |
| G13, G14 | IL-22 |
| G15, G16 | IL-23 |
| G17, G18 | IL-27 p28 |

| Coordinate | Analyte/Control |
| --- | --- |
| G19, G20 | IL-28A/B |
| G21, G22 | IL-33 |
| G23, G24 | LDL R |
| H1, H2 | Leptin |
| H3, H4 | LIF |
| H5, H6 | Lipocalin-2/NGAL |
| H7, H8 | LIX |
| H9, H10 | M-CSF |
| H11, H12 | MMP-2 |
| H13, H14 | MMP-3 |
| H15, H16 | MMP-9 |
| H17, H18 | Myeloperoxidase |
| H19, H20 | Osteopontin (OPN) |
| H21, H22 | Osteoprotegerin/TNFRSF11B |
| H23, H24 | PD-ECGF/Thymidine phosphorylase |
| I1, I2 | PDGF-BB |
| I3, I4 | Pentraxin 2/SAP |
| I5, I6 | Pentraxin 3/TSG-14 |
| I7, I8 | Periostin/OSF-2 |
| I9, I10 | Pref-1/DLK-1/FA1 |
| I11, I12 | Prolactin |
| I13, I14 | Proprotein Convertase 9/PCSK9 |
| I15, I16 | RAGE |
| I17, I18 | RBP4 |
| I19, I20 | Reg3G |
| I21, I22 | Resistin |
| J1, J2 | Reference Spots |
| J3, J4 | E-Selectin/CD62E |
| J5, J6 | P-Selectin/CD62P |
| J7, J8 | Serpin E1/PAI-1 |
| J9, J10 | Serpin F1/PEDF |
| J11, J12 | Thrombopoietin |
| J13, J14 | TIM-1/KIM-1/HAVCR |
| J15, J16 | TNF-α |
| J17, J18 | VCAM-1/CD106 |
| J19, J20 | VEGF |
| J21, J22 | WISP-1/CCN4 |
| J23, J24 | Negative Control |

```
                           SEQUENCE LISTING

<160> NUMBER OF SEQ ID NOS: 24

<210> SEQ ID NO 1
<211> LENGTH: 808
<212> TYPE: DNA
<213> ORGANISM: Debaryomyces hansenii

<400> SEQUENCE: 1
accaaggtat catggtcggt atgggacaaa aggactctta tgttggggat gaagcccaat        60
ccaagagagg tatcttgacc ttgagatacc ctatcgaaca cggtattgtc accaactggg       120
acgatatgga aaagatctgg catcacacct tctacaacga attgagagtt gccccagaag       180
aacacccagt tttgttgacc gaagccccaa tgaaccctaa atctaaccgt gaaaagatga       240
cccaaatcat gtttgaaacc ttcaacgtac cagccttcta cgtttctatt caagccgtct       300
tatctttata ctcgtctggt agaaccaccg gtatcgtttt agattcgggt gatggtgtta       360
ctcacgttgt tccaatttac gccggtttct ccttaccaca cggtatctta agaattgact       420
tggctggtag agacttgacc gactacttga tgaagatctt gtccgaaaga ggttacactt       480
tctccaccac cgctgaaaga gaaattgtcc gtgatatcaa agaaaaatta tgttatgttg       540
ccttggactt tgaacaagaa atgcaaactt catctcaatc ctccgccatc gaaaagtctt       600
acgaattacc tgatggtcaa gttattacta tcggtaacga aagatttaga gcttccgaag       660
ctttgttccg tccttctgac ttaggtttag aagccgctgg tattgaccaa accacttaca       720
actcgattat gaagtgtgat gtcgatgtca gaaaggaatt atacggtaac attgttatgt       780
ctggtggtac caccatgttc cctggtat                                         808

<210> SEQ ID NO 2
<211> LENGTH: 808
<212> TYPE: DNA
<213> ORGANISM: Artificial Sequence
<220> FEATURE:
<223> OTHER INFORMATION: SYNTHETIC SEQUENCE

<400> SEQUENCE: 2
accaaggtat catggtcggt atgggacaaa aggactctta tgttggggat gaagcccaat        60
ccaagagagg tatcttgacc ttgagatacc ctatcgaaca cggtattgtc accaactggg       120
acgatatgga aaagatctgg catcacacct tctacaacga attgagagtt gccccagaag       180
aacacccagt tttgttgacc gaagccccaa tgaaccctaa atctaaccgt gaaaagatga       240
cccaaatcat gtttgaaacc ttcaacgtac cagccttcta cgtttctatt caagccgtct       300
tatctttata ctcgtctggt agaaccaccg gtatcgtttt agattcgggt gatggtgtta       360
ctcacgttgt tccaatttac gccggtttct ccttaccaca cggtatctta agaattgact       420
tggctggtag agacttgacc gactacttga tgaagatctt gtccgaaaga ggttacactt       480
tctccaccac cgctgaaaga gaaattgtcc gtgatatcaa agaaaaatta tgttatgttg       540
ccttggactt tgaacaagaa atgcaaactt catctcaatc ctccgccatc gaaaagtctt       600
acgaattacc tgatggtcaa gttattacta tcggtaacga aagatttaga gcttccgaag       660
ctttgttccg tccttctgac ttaggtttag aagccgctgg tattgaccaa accacttaca       720
actcgattat gaagtgtgat gtcgatgtca gaaaggaatt atacggtaac attgttatgt       780
```

```
ctggtggtac caccatgttc cctggtat                                             808

<210> SEQ ID NO 3
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 3
aacggtgaga gatttctgtg c                                                    21

<210> SEQ ID NO 4
<211> LENGTH: 20
<212> TYPE: DNA
<213> ORGANISM: Artificial Sequence
<220> FEATURE:
<223> OTHER INFORMATION: SYNTHETIC SEQUENCE

<400> SEQUENCE: 4
agctggcagt attcccacag                                                      20

<210> SEQ ID NO 5
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 5
tttggtggcg ggagcaatcc t                                                    21

<210> SEQ ID NO 6
<211> LENGTH: 24
<212> TYPE: DNA
<213> ORGANISM: Artificial Sequence
<220> FEATURE:
<223> OTHER INFORMATION: SYNTHETIC SEQUENCE

<400> SEQUENCE: 6
cgatgcgaga accaagagat ccgt                                                 24

<210> SEQ ID NO 7
<211> LENGTH: 25
<212> TYPE: DNA
<213> ORGANISM: Artificial Sequence
<220> FEATURE:
<223> OTHER INFORMATION: SYNTHETIC SEQUENCE

<400> SEQUENCE: 7
gcgactatga acaggtttcc aacga                                                25

<210> SEQ ID NO 8
<211> LENGTH: 24
<212> TYPE: DNA
<213> ORGANISM: Artificial Sequence
<220> FEATURE:
<223> OTHER INFORMATION: SYNTHETIC SEQUENCE

<400> SEQUENCE: 8
ccttcaatgt aacatcagcg gccc                                                 24

<210> SEQ ID NO 9
<211> LENGTH: 22
<212> TYPE: DNA
<213> ORGANISM: Artificial Sequence
```

```
<220> FEATURE:
<223> OTHER INFORMATION: SYNTHETIC SEQUENCE

<400> SEQUENCE: 9
cttggtcatt tagaggaagt aa                                                  22

<210> SEQ ID NO 10
<211> LENGTH: 20
<212> TYPE: DNA
<213> ORGANISM: Artificial Sequence
<220> FEATURE:
<223> OTHER INFORMATION: SYNTHETIC SEQUENCE

<400> SEQUENCE: 10
gctgcgttct tcatcgatgc                                                     20

<210> SEQ ID NO 11
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 11
gaggctcttc agaatgagca aa                                                  22

<210> SEQ ID NO 12
<211> LENGTH: 19
<212> TYPE: DNA
<213> ORGANISM: Artificial Sequence
<220> FEATURE:
<223> OTHER INFORMATION: SYNTHETIC SEQUENCE

<400> SEQUENCE: 12
ctctgcggtc agtctctct                                                      19

<210> SEQ ID NO 13
<211> LENGTH: 19
<212> TYPE: DNA
<213> ORGANISM: Artificial Sequence
<220> FEATURE:
<223> OTHER INFORMATION: SYNTHETIC SEQUENCE

<400> SEQUENCE: 13
ctggagccat gggtatgca                                                      19

<210> SEQ ID NO 14
<211> LENGTH: 20
<212> TYPE: DNA
<213> ORGANISM: Artificial Sequence
<220> FEATURE:
<223> OTHER INFORMATION: SYNTHETIC SEQUENCE

<400> SEQUENCE: 14
aagcacaagc cgagactgct                                                     20

<210> SEQ ID NO 15
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 15
aagctcagcc agaactggtc t                                                   21
```

```
<210> SEQ ID NO 16
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 16
atggcctggg acctaaaggt gaa                                        23

<210> SEQ ID NO 17
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 17
aggtcggtgt gaacggattt g                                          21

<210> SEQ ID NO 18
<211> LENGTH: 23
<212> TYPE: DNA
<213> ORGANISM: Artificial Sequence
<220> FEATURE:
<223> OTHER INFORMATION: SYNTHETIC SEQUENCE

<400> SEQUENCE: 18
tgtagaccat gtagttgagg tca                                        23

<210> SEQ ID NO 19
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 19
gacctgccgt ctagaaaaac c                                          21

<210> SEQ ID NO 20
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 20
gctgtagcca aattcgttgt c                                          21

<210> SEQ ID NO 21
<211> LENGTH: 21
<212> TYPE: DNA
<213> ORGANISM: Artificial Sequence
<220> FEATURE:
<223> OTHER INFORMATION: SYNTHETIC SEQUENCE

<400> SEQUENCE: 21
ctggagcagc tgaatggaaa g                                          21

<210> SEQ ID NO 22
<211> LENGTH: 22
<212> TYPE: DNA
<213> ORGANISM: Artificial Sequence
<220> FEATURE:
<223> OTHER INFORMATION: SYNTHETIC SEQUENCE
```

-continued

```
<400> SEQUENCE: 22
cttctccgtc atctccatag gg                                                22

<210> SEQ ID NO 23
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 23
tgcccacgtc aaggagtatt tc                                                22

<210> SEQ ID NO 24
<211> LENGTH: 22
<212> TYPE: DNA
<213> ORGANISM: Artificial Sequence
<220> FEATURE:
<223> OTHER INFORMATION: SYNTHETIC SEQUENCE

<400> SEQUENCE: 24
aacccacttc ttctctgggt tg                                                22
```

*DEBARYOMYCES* SPECIES AS AN INDICATOR OF NON-HEALING ULCERS IN CROHN'S DISEASE

CROSS-REFERENCE TO RELATED APPLICATIONS

This application is the United States national phase of International Application No. PCT/US2020/64376 filed Dec. 10, 2020. This application claims priority from U.S. Provisional Application Ser. No. 62/946,427 filed on Dec. 10, 2019, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

The Sequence Listing, which is a part of the present disclosure, includes a computer readable format (CRF) document entitled "019293-WO-US_SUBSTITUTE_SEQ_LISTING_ST25.TXT" sized 7 kb and created on 28 Nov. 2022 comprising nucleotide and/or amino acid sequences of the present invention. The subject matter of the Sequence Listing is incorporated herein by reference in its entirety.

FIELD OF THE DISCLOSURE

The present disclosure generally relates to methods of diagnosis, treatment, treatment selection, and treatment monitoring for an inflammatory bowel disease.

BACKGROUND OF THE DISCLOSURE

Inflammatory bowel diseases (IBDs) including ulcerative colitis and Crohn's disease are inflammatory conditions of the small intestine and colon. In 2015, approximately 3 million adults were diagnosed with IBD in the United States, a significant increase from 2009 (2 million). IBD is a complex disease, which occurs because of interaction between environment and genetic components, leading to inflammatory responses in the intestine. The most common treatment strategy for IBD is to inhibit inflammation by administration of anti-inflammatory compounds such as anti-TNF drugs. However, a significant proportion of IBD patients do not respond to anti-TNF drugs and there remains an unmet need for effective therapeutics against the disease.

When a tissue is injured, appropriate wound healing is necessary to regain function. Wounds can remain chronically non-healed due to a persistent injury stimulus and/or failure of repair, both of which can promote chronic inflammation. Taken together, poor repair and chronic inflammation are key features of human intestinal diseases, most notably inflammatory bowel diseases (IBD), including Crohn's disease (CD) and ulcerative colitis (UC). In IBD, dysregulation of pro-inflammatory processes occurs along with shifts in the composition of microbial populations (including bacteria, fungi, and viruses) in the intestinal lumen. The potential link between specific microbes and inflammation in IBD has been of long-standing interest. It is unclear how specific microbes, especially fungi, can inhibit the normal healing response and perpetuate damage in IBD.

2

SUMMARY

In one aspect, a method for treating an inflammatory bowel disease in a patient in need is disclosed that includes administering a therapeutically effective amount of an antifungal compound to the patient in need. In some aspects, the inflammatory bowel disease is selected from Crohn's disease and ulcerative colitis. In some aspects, the antifungal compound is administered to reduce levels of fungi in the gut microbiome of the patient. In some aspects, the antifungal compound is administered to reduce levels of fungi of the genus *Debaryomyces* in the gut microbiome of the patient. In some aspects, the antifungal compound is administered to reduce levels of fungi of the species *Debaryomyces hansenii* in the gut microbiome of the patient. In some aspects, the antifungal compound is selected from fluconazole, caspofungin, flucytosine, any variation thereof, and any combination thereof. In some aspects, the antifungal compound is caspofungin and any variation thereof.

In another aspect, a method for selecting a treatment for an inflammatory bowel disease to be administered to a patient in need is disclosed. The method includes obtaining a sample from the patient, detecting a biomarker within the sample, and selecting the treatment if the biomarker is above a threshold level. The biomarker is indicative of a fungus amount within a gut microbiome of the patient. The treatment includes administering a therapeutically effective amount of an antifungal compound to the patient in need. In some aspects, the sample is selected from a fecal sample, a blood sample, an intestinal biopsy sample, and an excised intestinal tissue sample. In some aspects, the inflammatory bowel disease is selected from Crohn's disease and ulcerative colitis. In some aspects, detecting the biomarker within the sample further includes at least one of i) detecting an abundance of DNA sequences of the fungi within a sample that may be the fecal sample, the intestinal biopsy sample, the excised intestinal tissue sample, and any combination thereof; ii) detecting a concentration of antibodies against the fungus within a blood sample or a serum sample. In some aspects, the antifungal compound is administered to reduce levels of the fungi in the gut microbiome of the patient. In some aspects, the antifungal compound is administered to reduce intestinal levels of fungi of the genus *Debaryomyces* in the gut microbiome of the patient. In some aspects, the antifungal compound is administered to reduce intestinal levels of fungi of the species *Debaryomyces hansenii* in the gut microbiome of the patient. In some aspects, the antifungal compound is selected from fluconazole, caspofungin, flucytosine, any variation thereof, and any combination thereof. In some aspects, the antifungal compound caspofungin and any variation thereof.

In an additional aspect, a method for monitoring a treatment for an inflammatory bowel disease administered to a patient in need is disclosed. The method includes obtaining a pre-treatment sample from the patient prior to administering the treatment and at least one post-treatment sample after administering the treatment. The methods also includes detecting a biomarker within the sample and comparing the biomarker within the pre-treatment sample and within the at least one post-treatment sample to determine if the biomarker increases or decreases after administering the treatment. The biomarker is indicative of a fungus amount within a gut microbiome of the patient. In some aspects, the method further includes continuing the treatment if the biomarker decreases after administering the treatment or modifying the treatment if the biomarker increases after administering the treatment. In some aspects, the sample is selected from a fecal sample, a blood sample, an intestinal biopsy sample, and an excised intestinal tissue sample. In some aspects, the inflammatory bowel disease is selected from Crohn's disease and ulcerative colitis. In some aspects, detecting the biomarker within the sample further includes at least one of i) detecting an abundance of DNA sequences of the fungi within a sample, where the sample may be the fecal sample, the intestinal biopsy sample, the excised intestinal tissue sample, and any combination thereof; and ii) detecting a concentration of antibodies against the fungus within the blood sample or the serum sample. In some aspects, the antifungal compound is administered to reduce levels of the fungi in the gut microbiome of the patient. In some aspects, the antifungal compound is administered to reduce levels of fungi of the genus *Debaryomyces* in the gut microbiome of the patient. In some aspects, the antifungal compound is administered to reduce intestinal levels of fungi of the species *Debaryomyces hansenii* in the gut microbiome of the patient. In some aspects, the antifungal compound is selected from fluconazole, caspofungin, flucytosine, any variation thereof, and any combination thereof. In some aspects, the antifungal compound is caspofungin or variation thereof.

Other aspects of the disclosure are described in the detailed description and examples below.

DESCRIPTION OF THE DRAWINGS

The following drawings illustrate various aspects of the disclosure.

FIG. 5B is a table mapping the antifungal screen of FIG. 5A.

FIG. 14: High throughput ITS sequencing of mouse fecal DNA. (A) Stool was collected from Kool-Aid (control) or VNAM treated mice, DNA was extracted and the ITS region was amplified followed by high throughput sequencing. Relative abundances of identified genera are shown for each individual mouse sample (C=control mice, V=VNAM-treated mice) as stacked bars, and for the average per treatment group as pie charts (n=15 mice/group from 4 experiments). Only genera with a combined mean across both groups of >1.5% relative abundance are plotted. All other genera are combined into "Other."

FIG. 15: Fungal colonies isolated from wounds in VNAM-treated mice were identified as *D. hansenii*. (A) Sequence alignment of the ACT1 gene from isolate B6A1 (obtained from the wound of a VNAM treated mouse) using NCBI BLASTN. The top 20 hits in the nucleotide collection database available through NCBI with greater than 99% identity were for *D. hansenii* (or *C. famata*); alignment to the first hit is shown.

FIG. 27: CD45+F480+ cells are a major source of IFN-(3 in the colonic wounds of *D. hansenii* infected mice. WT mice were administered PBS (controls) or *D. hansenii*, exposed to DSS for 7 days followed by 5 days of regular drinking water. Relative expression of IFN-(3 in the indicated cell fractions isolated from the wounds of mice exposed to DSS in the presence or absence of *D. hansenii* (n=4-6 mice/group from 2 separate experiments). Significance was determined by two-way ANOVA and TUKEY's post-hoc test: ****p<0.0001. All values are displayed as mean±SEM.

FIG. 28: Pathogenic effects of *D. hansenii* are partially dependent on TLR3. Bone marrow-derived macrophages from (A) clec7a–/–, or (B) Tlr3–/– mice and respective WT littermate controls were cultured in the presence or absence of live *D. hansenii* (MOI 1:10) for 24 hours followed by quantification of CCL5 in the supernatant by ELISA (n=4 independent experiments). Significance was determined by unpaired Student's t-test: ****p<0.0001. N.S. indicates not significant. (C) Representative images (Bars=100 μm) of H&E stained sections of colons from Tlr3–/– and WT littermate controls gavaged with *D. hansenii* and exposed to DSS followed by two weeks recovery. (D) Crypt loss in the groups from (C) (n=4-7 mice per group from 3 experiments). Significance was determined by unpaired Student's t-test: ****p<0.0001.

FIG. 29: Debaryomyces is significantly enriched in inflamed compared to uninflamed regions from CD patients. Mean relative abundance of Debaryomyces in the indicated groups from the surgical cohort (as shown in FIG. 11D) (n=6 CD patients/group). Significance was determined by paired Student's t-test: **p<0.01.

FIG. 30: *D. hansenii* antibodies and CCL5 are increased in the serum of CD patients. (A) IgA antibodies directed against a clinical isolate of *D. hansenii* (CDA1) and (B) CCL5 were measured in the serum by ELISA. Significance was determined by unpaired Student's t-test: **p<0.01. (C) Linear regression analysis demonstrated a significant correlation between serum IgA against *D. hansenii* and CCL5.

Figure 1A:
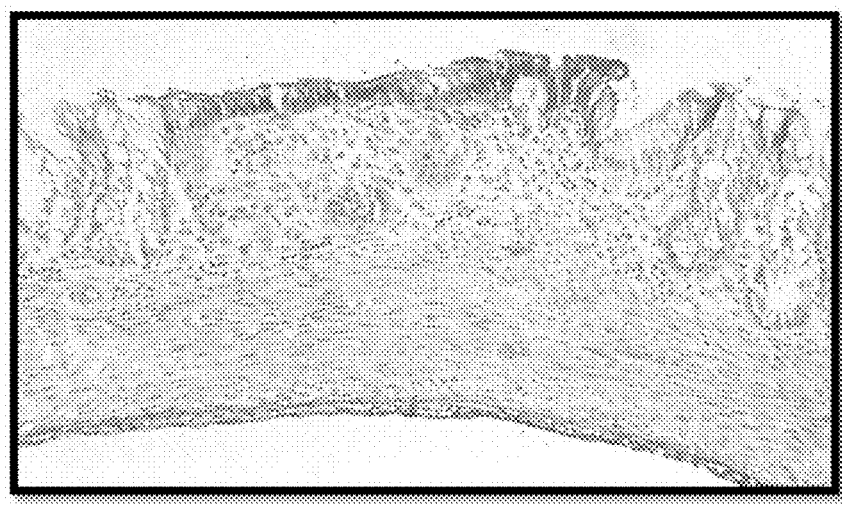
FIG. 1A contains a microscope image of a defective intestinal wound in a mouse model.

Those of skill in the art will understand that the drawings, described below, are for illustrative purposes only. The drawings are not intended to limit the scope of the present teachings in any way.

DETAILED DESCRIPTION

Alterations of the mycobiota composition associated with Crohn's disease (CD) are challenging to link to defining elements of pathophysiology such as poor injury repair. *D. hansenii* is commonly found in a variety of dairy products, in particular different varieties of cheese, processed meats and is considered to be a rare human fungal pathogen. Two independent reports recently showed *D. hansenii* is association with UC and colorectal cancer, however, the functional role of *D. hansenii* in the context of human diseases has not yet been characterized.

Here, we confirmed that both mouse and human isolates of *D. hansenii* impede repair providing a novel host micro-bial axis that can be targeted to improve mucosal healing in IBD. We provide direct evidence that mycobiota ecosystem in the tissue is not well reflected in the fecal material and it was only profiling of intestinal tissue that allowed us to isolate *D. hansenii* and test functionality. Thus, our findings support the use of a combination of culture-dependent and independent approaches from affected organs to identify pathogenic microbiota members in human diseases.

Using culture-dependent and independent methods, we discovered that *Debaryomyces hansenii* preferentially local-ized to and was abundant within incompletely healed intes-tinal wounds of mice and inflamed mucosal tissues of CD subjects. *D. hansenii* cultures from injured mice and inflamed CD tissues impaired colonic healing when intro-duced into injured conventionally-raised or gnotobiotic mice. We re-isolated *D. hansenii* from injured areas of these mice, fulfilling Koch's postulates. Mechanistically, *D. han-senii* impaired mucosal healing via myeloid cell-specific type 1 Interferon (IFN)/CCL5 axis. Taken together, we have identified a fungus that inhabits inflamed CD tissue and can lead to dysregulated mucosal healing.

The present disclosure is based, at least in part, on the discovery that a fungus species previously uncharacterized within the gut microbiota, *Debaryomyces* sp. has a detri-mental role in intestinal healing. As described in detail below, it was discovered that *Debaryomyces* fungus was enriched in patients of Crohn's disease, indicating a possible contribution of *Debaryomyces* fungus to the pathology of Crohn's disease and potentially other inflammatory bowel diseases (IBD).

Although numerous studies have shown changes in gut microbiota in inflammatory bowel diseases (IBD), the rel-evance of individual species to the pathogenesis remains understudied. Additionally, the role of bacteria has been extensively explored, but how fungal population impacts IBD is relatively unclear.

Without being limited to any particular theory, one man-ner by which a single microbe can be considered a cause of a disease is by evaluating if the microbe can fulfill Koch's postulates. Koch's postulates were published in 1890 and are defined as: 1) the microorganism must be found in abundance in organisms suffering from the disease; 2) the microorganism must be isolated from a diseased organism and grown in pure culture; 3) the cultured microorganism should cause disease when introduced into a healthy organ-ism; and 4) the microorganism must be re-isolated from the inoculated, diseased experimental host and identified as being identical to the original specific causative agent.

As disclosed in the examples below, fungus of the *Debaryomyces* sp. was cultured from inflamed tissue of Crohn's disease. The role of *Debaryomyces* sp. in disruption of intestinal healing was confirmed by orally administering *Debaryomyces* sp. to mice and demonstrating defective repair. Further, live *Debaryomyces* fungus was re-cultured from wounds of colonized mice, indicating the fulfillment of Koch's postulates. Furthermore, to avoid artifacts of culture, unbiased sequencing inflamed tissue detects the presence of *Debaryomyces* sp.

One aspect of the present disclosure provides a method of diagnosing an inflammatory bowel disease, such as Crohn's disease, by detecting *Debaryomyces* fungus in an IBD patient. The *Debaryomyces* fungus may be detected by any known method without limitation including, but not limited to, sequencing of gut microbiota, immunological assays of blood or serum, and any other suitable assay.

In another aspect, the present disclosure provides a method of treating an IBD, such as Crohn's disease, by administration of an antifungal compound to the IBD patient. In one aspect, the IBD patient may be administered caspofungin to treat Crohn's disease.

Therapeutic Methods

Also provided is a process of treating, preventing, or reversing an inflammatory bowel disease such as Crohn's disease in a subject in need of administration of a therapeu-tically effective amount of an antifungal compound, so as to reduce the abundance of *Debaryomyces* sp. fungus in the gut, thereby reducing the detrimental effect of *Debaryomy-ces* sp. fungus on intestinal wound healing. Non-limiting examples of suitable antifungal compounds that may be administered to treating, preventing, or reversing an inflam-matory bowel disease such as Crohn's disease include fluconazole, caspofungin, and flucytosine. In one aspect, a process of treating, preventing, or reversing an inflammatory bowel disease such as Crohn's disease includes administer-ing a therapeutically effective amount of caspofungin to a patient in need.

Methods described herein are generally performed on a subject in need thereof. A subject in need of the therapeutic methods described herein can be a subject having, diagnosed with, suspected of having, or at risk for developing an inflammatory bowel disease such as Crohn's disease. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of an antifungal compound, for example, that amount that would cause the desired therapeutic effect in a subject while minimizing undesired side effects. In various embodiments, an effective amount of an antifungal compound described herein can substantially inhibit the detrimental effect of intestinal wounding associated with an inflammatory bowel disease such as Crohn's disease, slow the progress of intestinal wounding, or limit the development of intestinal wounding.

According to the methods described herein, administra-tion can be parenteral, pulmonary, oral, topical, intradermal, intramuscular, intraperitoneal, intravenous, intrathecal, intracranial, intracerebroventricular, subcutaneous, intrana-sal, epidural, ophthalmic, buccal, or rectal administration.

When used in the treatments described herein, a thera-peutically effective amount of the antifungal compound can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reduce the detrimental effect of *Debaryomyces* sp. on intestinal wound healing.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of the antifungal compound can occur as a single event or over a time course of treatment. For example, the antifungal compound can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for an inflammatory bowel disease such as Crohn's disease.

An antifungal compound can be administered simultaneously or sequentially with another agent, such as an antibiotic, an anti-inflammatory, or another agent. For example, an antifungal compound can be administered simultaneously with another agent, such as an antibiotic or an anti-inflammatory. Simultaneous administration can occur through administration of separate compositions, each containing one or more of an antifungal compound, an antibiotic, an anti-inflammatory, or another agent. Simultaneous administration can occur through administration of one composition containing two or more of an antifungal compound, an antibiotic, an anti-inflammatory, or another agent. An antifungal compound can be administered sequentially with an antibiotic, an anti-inflammatory, or another agent. For example, an antifungal compound can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, intrathecal, intracranial, intracerebroventricular, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump that may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors;

hydrophobicity character x log P of about –2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compounds during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Methods

In various aspects, the detection of the levels of fungus within the gut microbiota using any of the methods described herein may be used in methods of diagnosing an inflammatory bowel disease, selecting a treatment for inflammatory bowel disease and/or monitoring treatment of an inflammatory bowel disease as disclosed herein.

In some aspects, a method for diagnosing an inflammatory bowel disease may include obtaining a sample from a patient and detecting a biomarker indicative of an amount of a fungus within the gut microbiome of the patient. If the biomarker exceeds a threshold level, the patient may be diagnosed with an inflammatory bowel disease. In other aspects, the measured level of the biomarker may be used to assess the severity of the diagnosed inflammatory bowel disease, the patient prognosis, and/or to select a treatment. In some aspects, a method of selecting a treatment for an inflammatory bowel disease includes selecting a treatment that includes comprising administering a therapeutically effective amount of an antifungal compound to the patient in need if the biomarker within the sample exceeds a threshold value.

In other aspects, the method of monitoring treatment for an inflammatory bowel disease includes comparing the biomarker levels measured from a pre-treatment sample and at least one post-treatment sample. The treatment is continued if the biomarker decreases after treatment and the treatment is modified if the biomarker increases after treatment.

Any suitable sample described herein may be used in the above methods including, but not limited to fecal samples, blood/plasma samples, intestinal biopsy samples, and excised intestinal tissue samples.

In various aspects, the biomarkers include any suitable biomarker indicative of a fungus amount within the gut microbiome of the patient as described herein. Non-limiting examples of suitable biomarkers include an abundance of fungal DNA sequences within a sample, wherein the sample may be a fecal sample, an intestinal biopsy sample, or an excised intestinal tissue sample. Other non-limiting examples of suitable biomarkers include a concentration of antibodies against the fungus within a blood or serum sample. In various aspects, the biomarkers may be measured using any of the methods described herein. Non-limiting examples of suitable biomarker measurement methods include DNA sequencing, immunological assays, and any other suitable assay or measurement method without limitation.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Effect of Antibiotics on Intestinal Healing

Figure 1B:
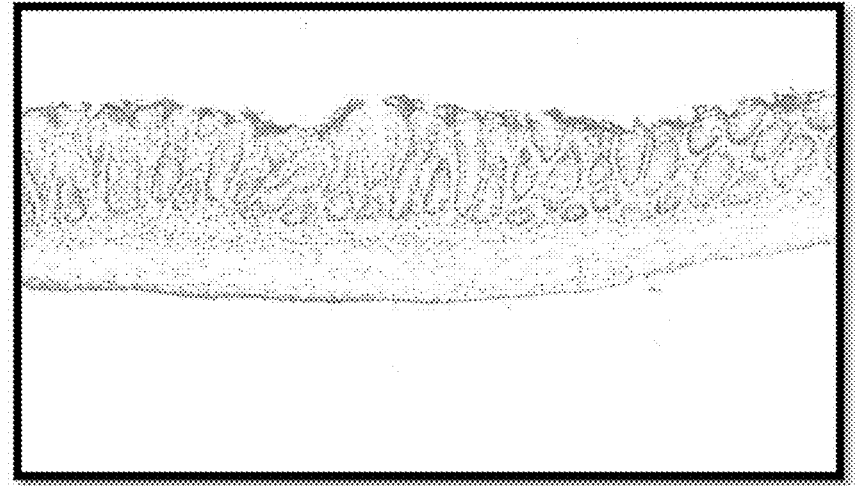
FIG. 1B contains a microscope image of intestinal wound healing in a mouse administered antibiotics (Abx).
Figure 1C:
FIG. 1C contains a microscope image of intestinal wound healing in a mouse co-administered antibiotics (Abx) and antifungals.
Figure 2A:
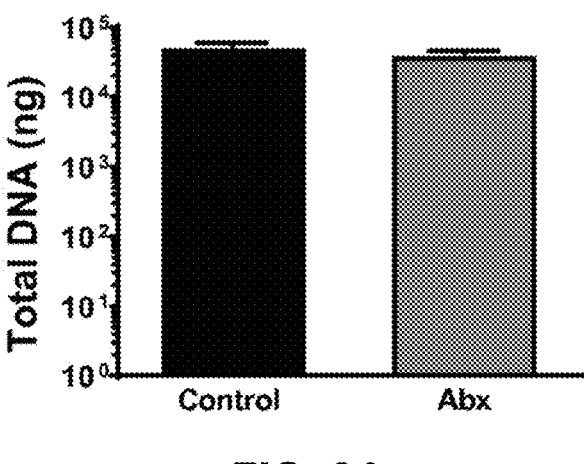
FIG. 2A is a graph summarizing the total DNA counts from tissue sequencing of unhealed wounds within intestinal tissues of mice treated with antibiotics (Abx) and untreated (Control).
Figure 2B:
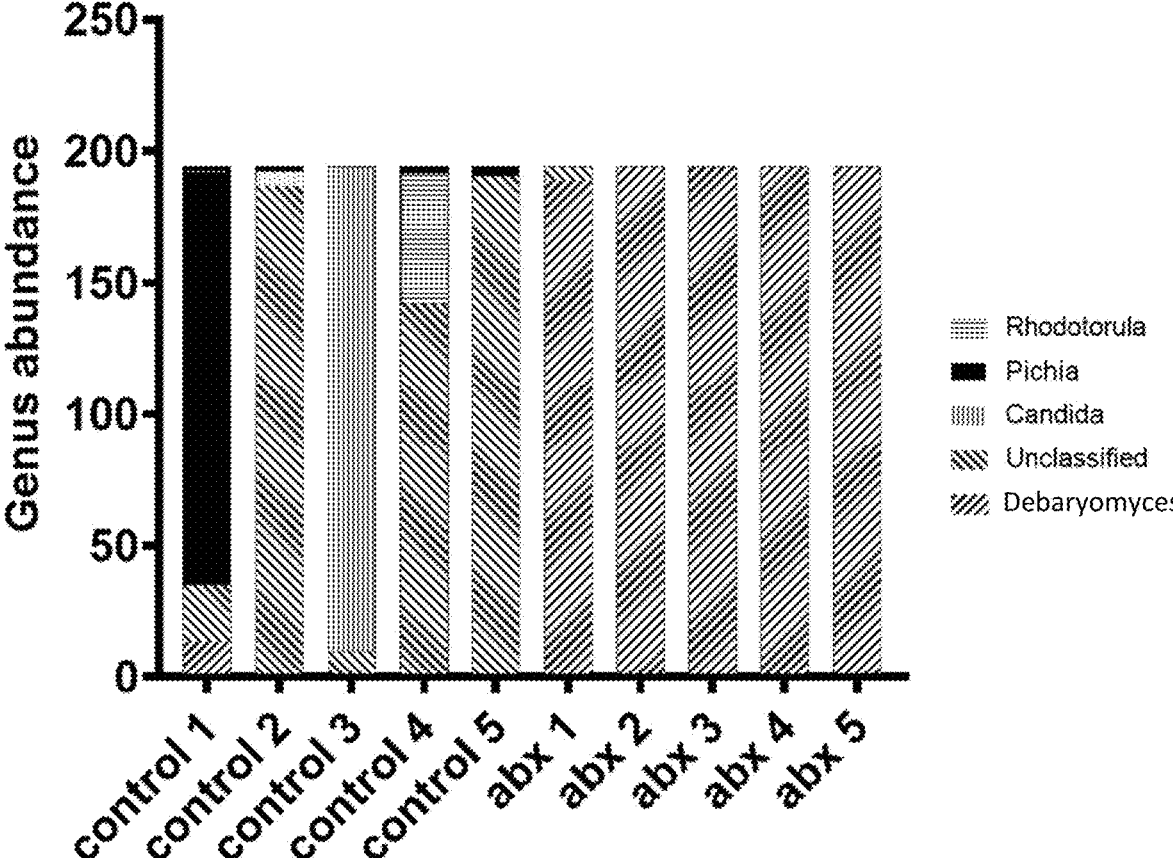
FIG. 2B is a graph summarizing the abundance of various fungal genera based on DNA counts from tissue sequencing of unhealed wounds within intestinal tissues of mice treated with antibiotics (Abx) and untreated (Control).
Figure 2C:
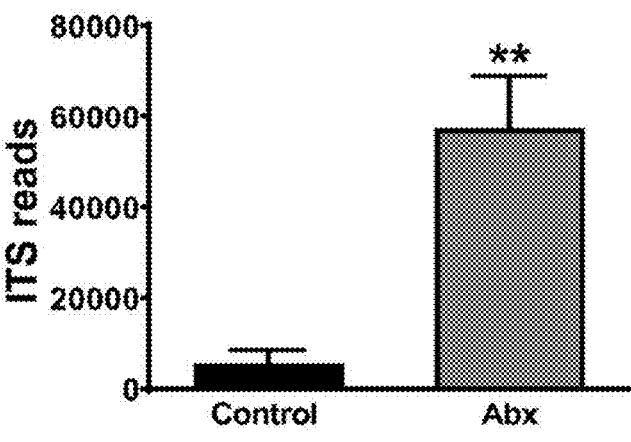
FIG. 2C is a graph summarizing the ITS reads from ITS sequencing of unhealed wounds within intestinal tissues of mice treated with antibiotics (Abx) and untreated (Control).
Figure 2D:
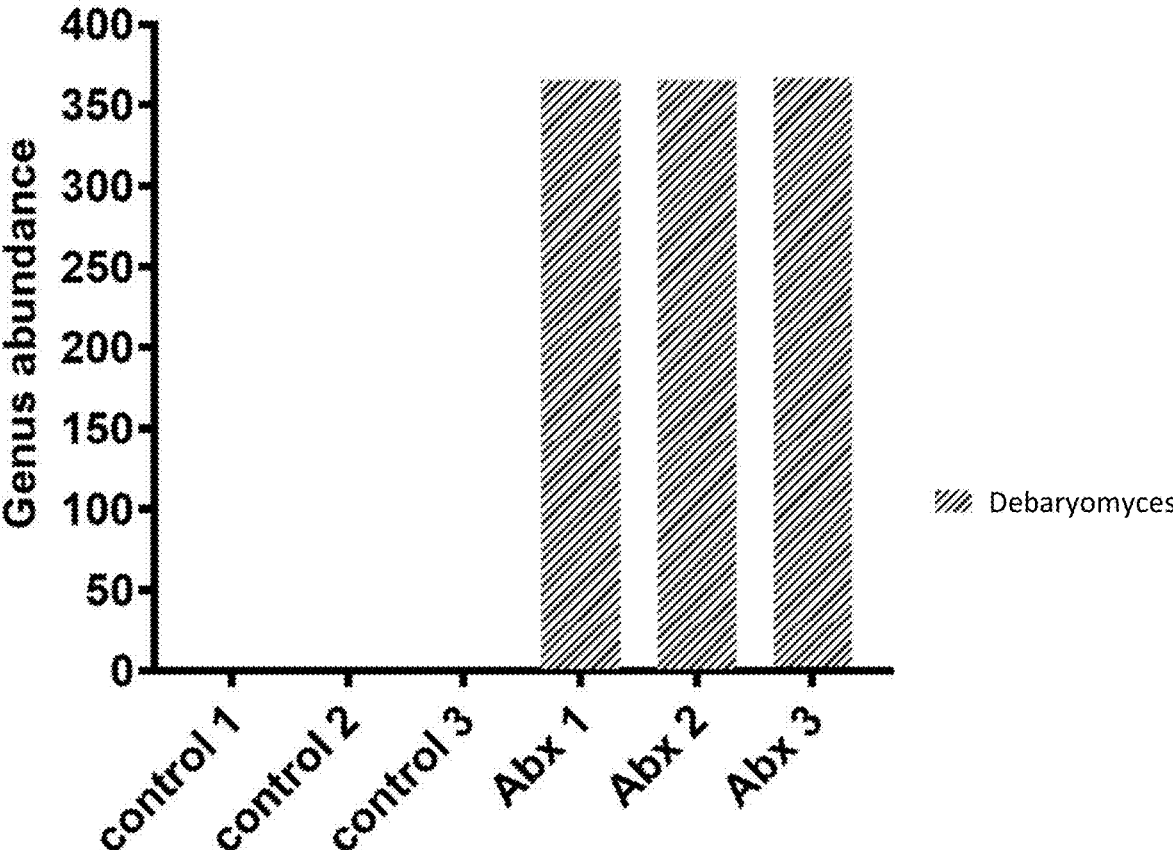
FIG. 2D is a graph summarizing the abundance of fungal genera based on ITS sequencing of pooled colonies from unhealed wounds within intestinal tissues of mice treated with antibiotics (Abx) and untreated (Control).

Mice treated with antibiotics (Abx) demonstrated defective intestinal healing post-injury, as illustrated in FIG. 1B. This phenotype could be rescued when Abx fed mice were concomitantly administered antifungal drugs, as illustrated in FIG. 1C. Hypothesizing that specific fungi contribute to the phenotype, colonic tissue of the mice was sequenced and an overwhelming enrichment of *Debaryomyces* sp. was detected in Abx fed mice, as summarized in FIGS. 2A, 2B, 2C, and 2D. 3. *Debaryomyces* sp. was subsequently cultured from colonic wound tissue of Abx, but not control mice or uninjured areas, confirming that live fungus inhabited wounds in Abx treated mice.

Figure 3A:
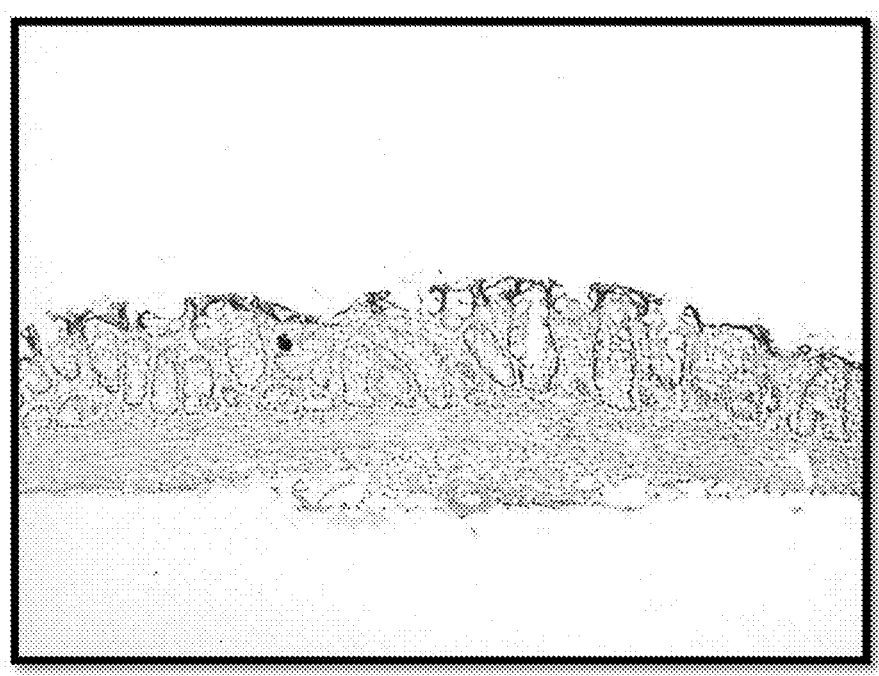
FIG. 3A contains a microscope image of a mouse intestine (control).
Figure 3B:
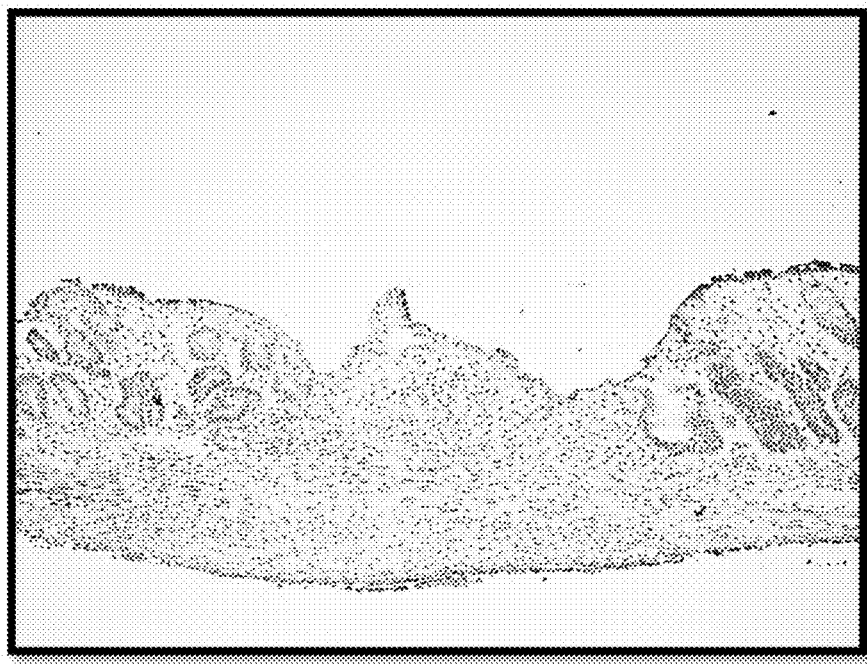
FIG. 3B contains a microscope image illustrating defective intestinal wound healing in a mouse inoculated with *Debaryomyces* sp.

To address if *Debaryomyces* sp. can affect healing, wounds were created in specific pathogen-free mice and the mice were gavaged with either PBS (controls. FIG. 3A) or *Debaryomyces* sp. *Debaryomyces* sp. colonized the wounds (FIG. 3B) and resulted in lack of colonic crypts and defective healing on 12-day post-injury as opposed to completely regenerated crypts in controls, as illustrated in FIG. 3A and FIG. 3B.

To understand the mechanism, an unbiased analysis of cytokines/chemokines of the wounded tissues revealed that out of 111 cytokines, only 4 chemokines were significantly (>2 fold) changed in infected wounds compared to controls. Interestingly, none of the known inflammatory cytokines such as TNF or IL6 was affected by *Debaryomyces* sp. Secondary validation using KO mice showed that CCL5 appears to mediate the effects of *Debaryomyces* sp. on inhibiting wound repair.

Example 2: Role of *Debaryomyces* Sp. in Crohn's Disease

Figure 4A:
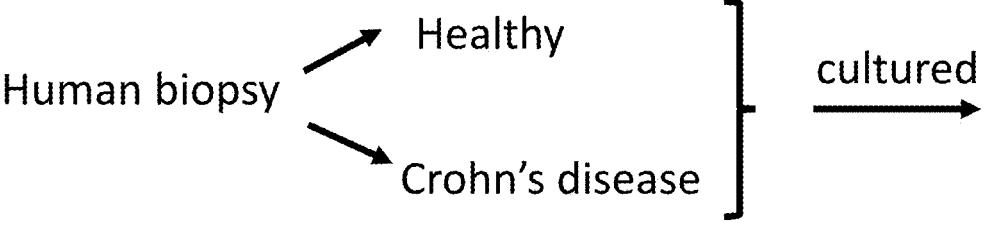
FIG. 4A is a flow chart illustrating the steps of obtaining samples for ITS sequencing from healthy volunteers (healthy) and Crohn's patients (patient).
Figure 4B:
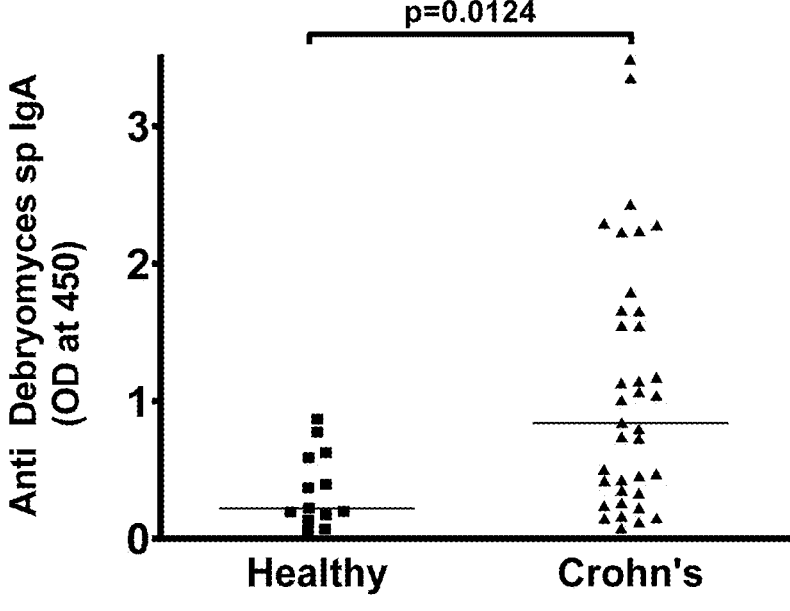
FIG. 4B is a graph comparing the abundance of *Debaryomyces* sp. within intestinal wounds associated with Crohn's patients versus healthy controls using an antibody-based assay.
Figures 4C, 4D:
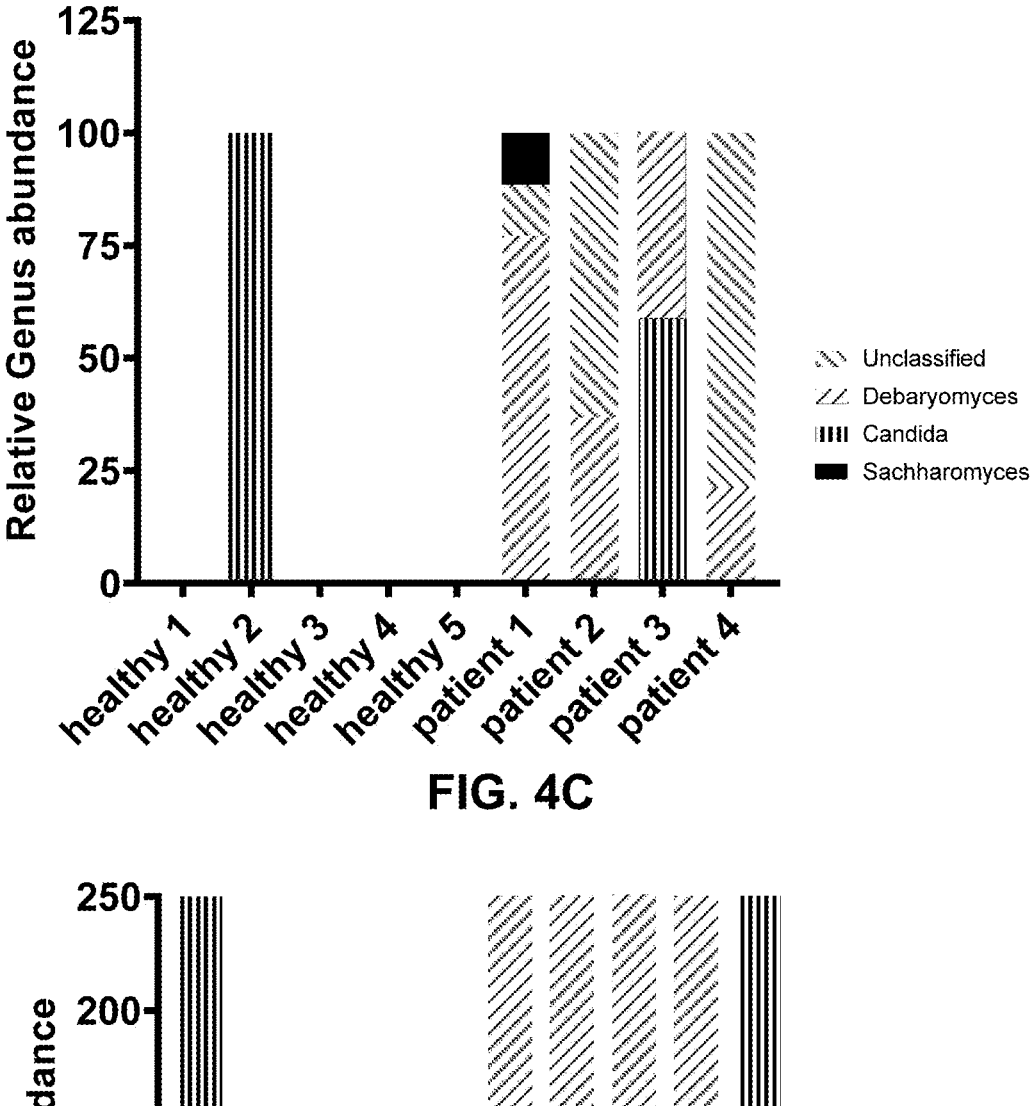
FIG. 4C is a graph summarizing the relative abundances of fungi genera in Crohn's patients versus healthy controls based on ITS sequencing.
FIG. 4D is a graph summarizing the abundances of fungi genera in Crohn's patients versus healthy controls based on ITS sequencing.

To assess the role of *Debaryomyces* sp. in Crohn's disease, the following experiments were conducted. A schematic diagram summarizing these experiments is provided as FIG. 4A. Surgical and biopsy samples were collected from 20 patients and 10 healthy controls. The samples were subjected to tissue sequencing analysis and tissue culture analysis. Using sequencing on surgical specimens, *Debaryomyces* sp. was detected in 75 percent of inflamed areas of intestines of Crohn's disease but not in uninflamed areas, as summarized in FIGS. 4C and 4D.

Figure 4E:
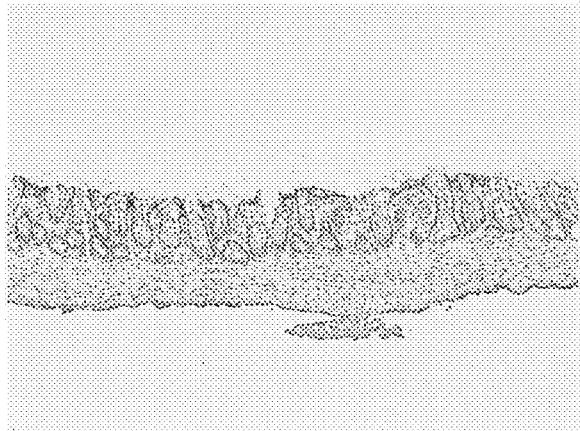
FIG. 4E contains a microscope image of a healthy human intestine.
Figure 4F:
FIG. 4F contains a microscope image of a human intestine of an XC (control).

To functionally test human isolated *Debaryomyces* sp, healing was evaluated in injured SPF mice gavaged with human *Debaryomyces* sp. Mice were also gavaged with *Candida albicans*, the second most common fungus found in patients of Crohn's disease. Interestingly, *Debaryomyces* sp, but not *Candida albicans*, induced defective healing demonstrated by lack of crypts and presence of cellular infiltrate in the wound bed, as illustrated in FIGS. 4E and 4F. The enrichment of *Debaryomyces* sp. in inflamed tissue was also associated with significantly higher IgA antibodies against *Debaryomyces* sp. in the serum of Crohn's disease patients, as summarized in FIG. 4B. In summary, these data suggest that the presence of *Debaryomyces* sp. in the inflamed tissue of Crohn's disease might be responsible for defective healing.

Example 3: Effectiveness of Antifungal Drugs Against *Debaryomyces* Sp.

Figure 5A:
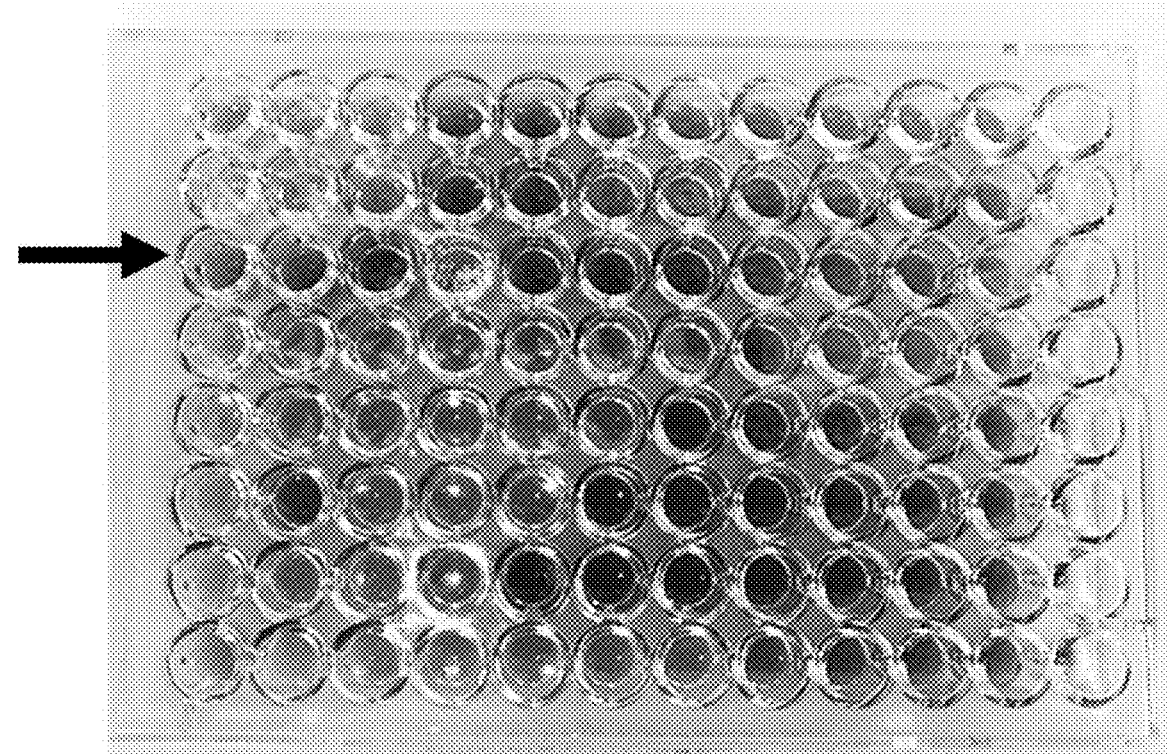
FIG. 5A is an image of a screen with water-soluble antifungals.
Figure 6A:
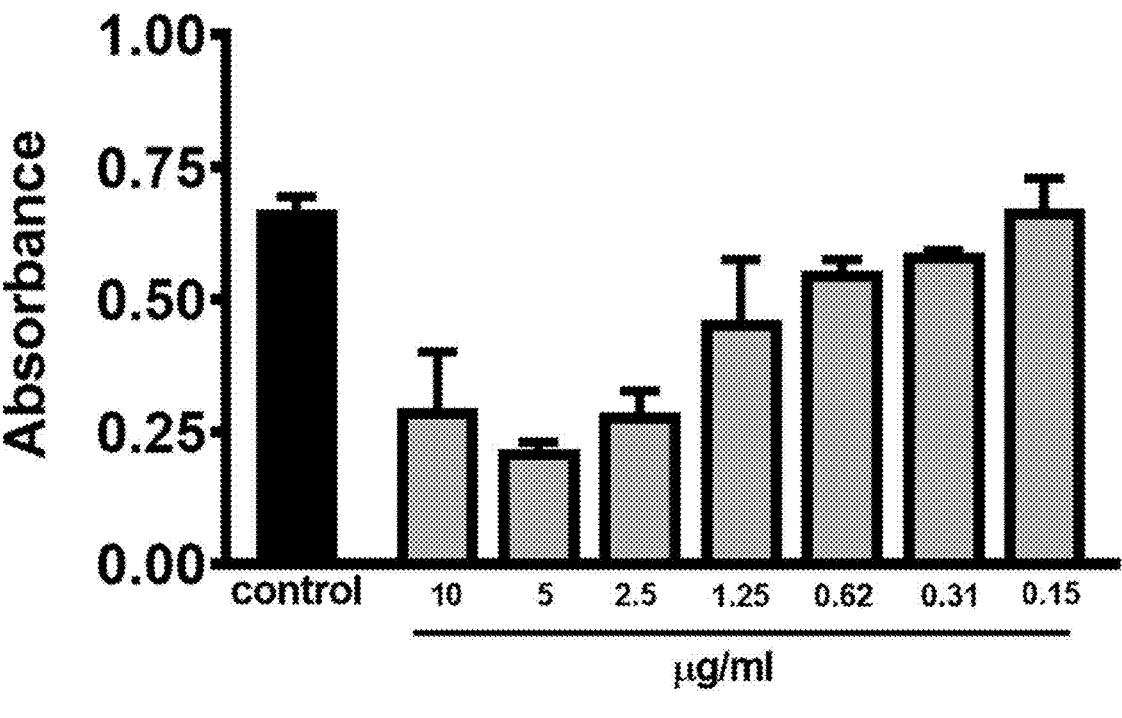
FIG. 6A is a graph summarizing the dose-response of the antifungal fluconazole against *Debaryomyces* sp.
Figure 6B:
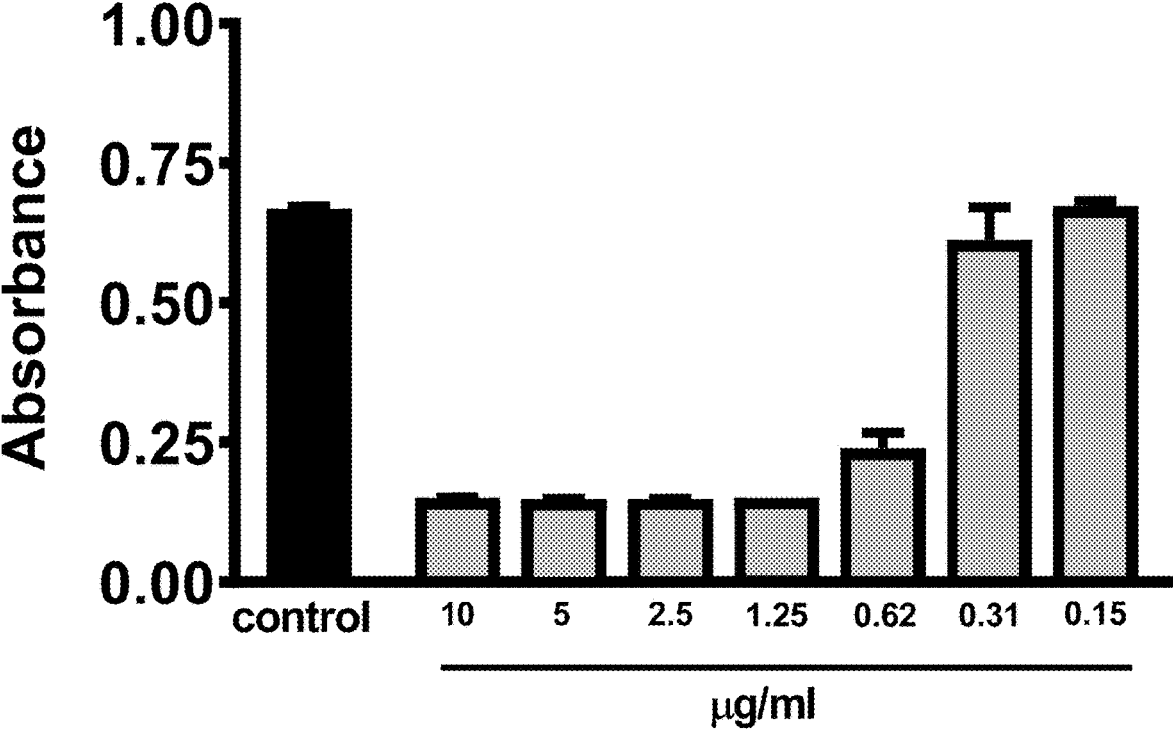
FIG. 6B is a graph summarizing the dose-response of the antifungal caspofungin against *Debaryomyces* sp.
Figure 6C:
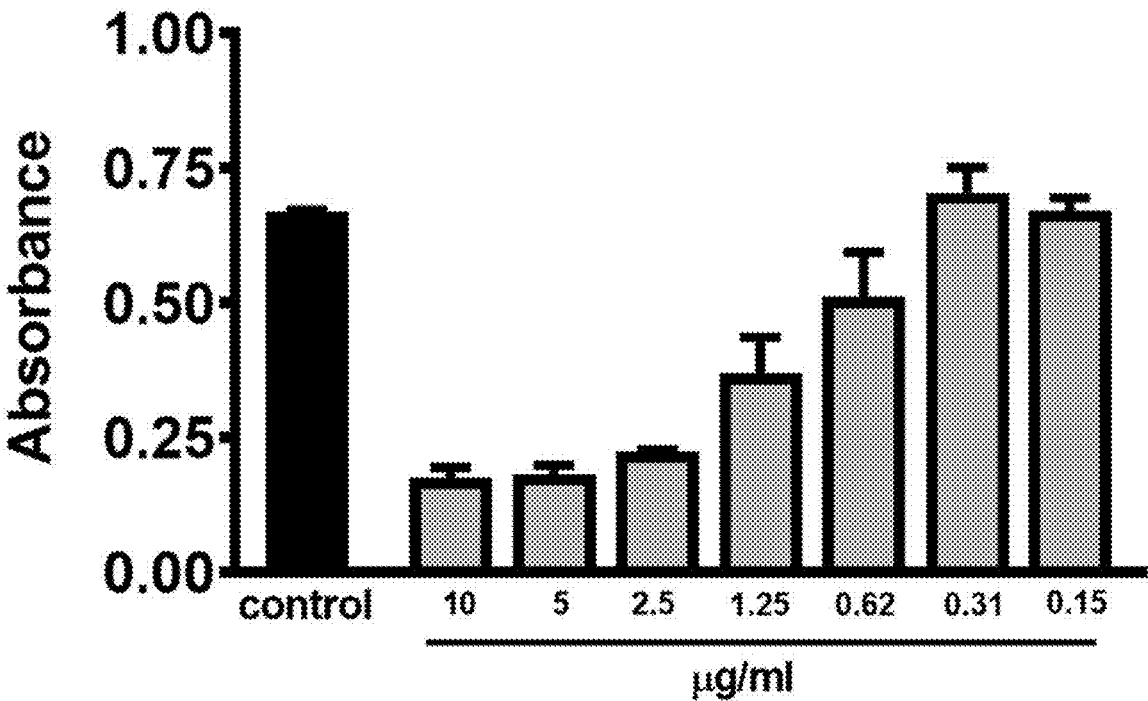
FIG. 6C is a graph summarizing the dose-response of the antifungal flucytosine against *Debaryomyces* sp.
Figure 7:
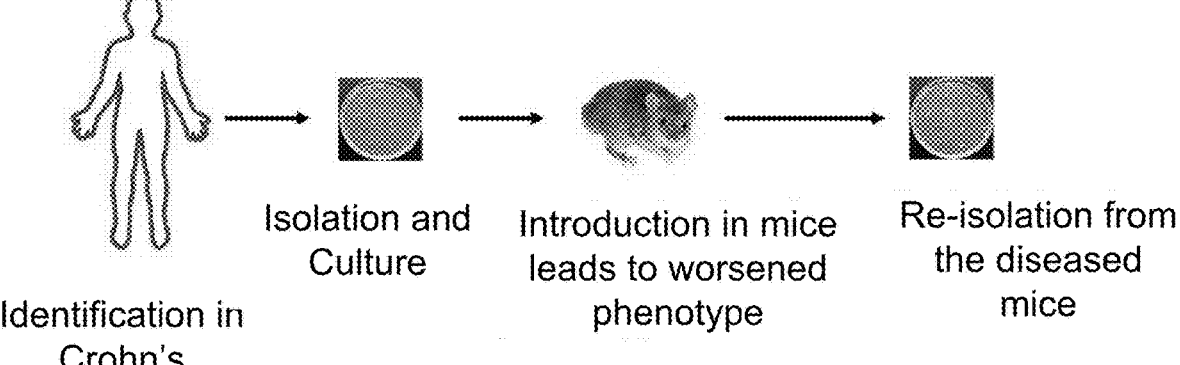
FIG. 7 is a schematic diagram illustrating a method of assessing the role of *Debaryomyces* sp. in Crohn's disease.

To evaluate the most potent antifungal drug against *Debaryomyces* sp., a mini screen was conducted with known water-soluble antifungals (see FIGS. 5A and 5B) and found that caspofungin (CAS) was the most effective at lowest concentrations (MIC-0.62 µg/ml) compared to azoles that are commonly used for treatment in humans, as summarized in FIG. 6A (fluconazole), FIG. 6B (caspofungin), and FIG. 6C (flucytosine).

Example 4: Effectiveness of Antibiotic Drugs on Mucosal Healing

To test the role of microbes in mucosal wound repair, a biopsy injury model was used where the timing and site of injuries are known in each experiment. Wound repair in this model occurs in distinct phases. Barrier re-establishment begins immediately upon injury and lasts for 4 days, and is characterized by the formation of wound associated epithelial (WAE) cells that cover the denuded mucosa. Wound channel formation phase (day 4-day 8), involves extensive proliferation of epithelial cells in crypts adjacent to the wound, forming channels that emanate towards the center of the wound. These two phases culminate in the formation of new crypts that is complete within 12 days post-injury.

Mucosal healing in this model occurs in distinct phases where immediately upon injury, neutrophils are recruited to the injured site followed by the restoration of an epithelial barrier to initiate healing. The second phase of healing is characterized by an expansion of fibroblasts and macrophages in the wound bed that is concomitant with enhanced epithelial proliferation in the crypts immediately adjacent to the area of injury eventually leading to formation of new crypts. Arrest of the healing process at any phase typically leads to chronic inflammation characterized by a large area lacking crypts and infiltration by immune cells. Without being limited to any particular theory, disruption of the bacterial microbiota by specific antibiotics can negatively affect repair in this model, in part through augmentation of prostaglandin E2 (PGE2) production that in turn arrests repair by preventing epithelial stem cell expansion.

C57BL6 WT were purchased from Jackson Laboratories (Bar Harbor, ME) or Taconic Biosciences and acclimatized in a specific pathogen-free facility for 1 week before conducting any experiment. Biopsy forceps and a miniaturized colonoscope system (Karl Storz) were used to create mucosal wounds in the distal colon of mice as described previously. Briefly, mice were anesthetized using ketamine/xylazine and stool pellets were removed from the colon by flushing with PBS. Next, 3 French biopsy forceps were inserted into the colon and 3-5 thickness areas of mucosa and submucosa were removed under the guidance of an endoscopy camera. Biopsy injured mice were euthanized, and wounds were collected on days 4, 6, 8, and 12 to evaluate healing. Biopsy injury was performed by investigators blinded to the treatments.

Antibiotic-treated (VNAM) mice received the following cocktail for 4 weeks prior to biopsy injury until the day of sacrifice in drinking water: 0.5 g/L Vancomycin, 1 g/L Neomycin, 1 g/L Ampicillin, 1 g/L Metronidazole, and 1 g/L Kool-aid. Control mice received Kool-aid alone. Mice were treated with VNAM in the following figures: FIG. 8A-F, FIG. 9A-E, FIG. 12A-D, FIG. 13, FIG. 14, and FIG. 19A. For studying the effects of PGE2 inhibition, VNAM pretreated mice were biopsy injured and intraperitoneally injected with NS-398 (Cayman Chemical, 2.5 mg/kg body weight) from day 4-day 10 (twice daily) and sacrificed on day 12.

Colons were collected after the recovery phase; the wound length was measured and then they were flushed with sterile PBS to remove fecal pellets. Next, the colons were opened longitudinally and pinned in formalin, washed with 70% ethanol, and embedded in 2% agar for paraffin processing. 5 µm sections were cut and stained with H&E and evaluated by a pathologist blinded to the treatments. Percentage length of inflamed colon was defined as the percentage of colon that presented with 1) ulceration, 2) abnormal crypt morphology (loss of architecture, dropout, or abscess), 3) obvious signs of inflammatory cell influx, and 4) normal goblet cell presence. Crypt loss is defined as the percentage of rectum length with crypt dropout/loss from two representative 10x fields.

For hematoxylin and eosin (H&E) staining, wounds were collected and embedded in optimum cutting temperature (OCT) formulation (Thermo Fisher Scientific), and 5 µm frozen sections were obtained using a cryostat. The slides were fixed in 4% paraformaldehyde (PFA) for 15 mins, washed in water, and stained with hematoxlyin (EMD Millipore). The slides were then stained with eosin, dehydrated, passed through 3 changes of xylene, and mounted using Cytoseal (Thermo Fisher Scientific). Olympus BX-51 microscope and the digital camera DP22 were used to capture images. All wounds are created in the distal colon and smooth muscle was used as an indicator of the wounded region on day 12 (16). Images were analyzed using Olympus CellSens Standard imaging software to measure the wound bed length defined as the distance between the two farthest crypts in the center of the wound bed. 2-3 wounds per mouse were analyzed and wound bed lengths were averaged to obtain one value per mouse.

Figure 8A:
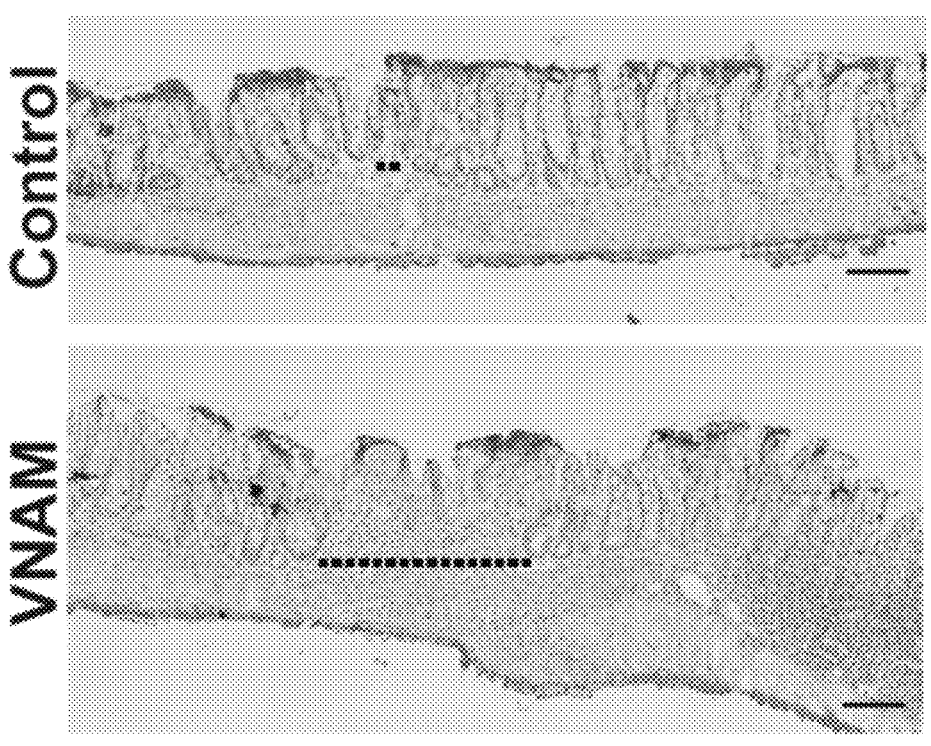
FIG. 8: Broad-spectrum antibiotic-mediated inhibition of colonic crypt regeneration was reversed by treatment with the antifungal drug amphotericin B. (A-B) WT specific pathogen-free mice (SPF) from JAX were given broad-spectrum antibiotics (VNAM) or Kool-Aid (vehicle control) in the drinking water for 4 weeks followed by biopsy injury. (A) Representative images of H&E stained sections from wounds of control or VNAM-treated mice at day 12 post-biopsy injury. (B) Wound bed length from control and VNAM-treated groups at day 12 post-injury (n=11-17 wounds/group from 7-8 mice/group). (C-D) VNAM pre-treated mice were biopsy injured and treated with either NS-398 (PGE2 synthesis inhibitor) or vehicle (control) (twice daily from days 4-10 post-injury). (C) Representative images of H&E stained sections and (D) wound bed length from vehicle and NS-398 treated groups (n=11-12/wounds/group from 5 mice per group) at day 12 post-injury. N.S. indicates not significant. (E-F) VNAM pre-treated mice were administered amphotericin B (AmpB) or vehicle (control) followed by biopsy injury. (E) Representative images of H&E stained sections of wounds day 12 post-injury from vehicle and amphotericin B treated mice. (F) Wound bed length from groups in (E) (n=12-13 wounds/group from 5-7 mice/group). Significance was determined by unpaired Student's t-test: ****p<0.0001. All values in B, D, and F are displayed as mean±SEM. The dashed black line in A, C, and E at the center of the wound represents wound bed length (largest distance between the crypts). Bars=100 μm.
Figure 8B:
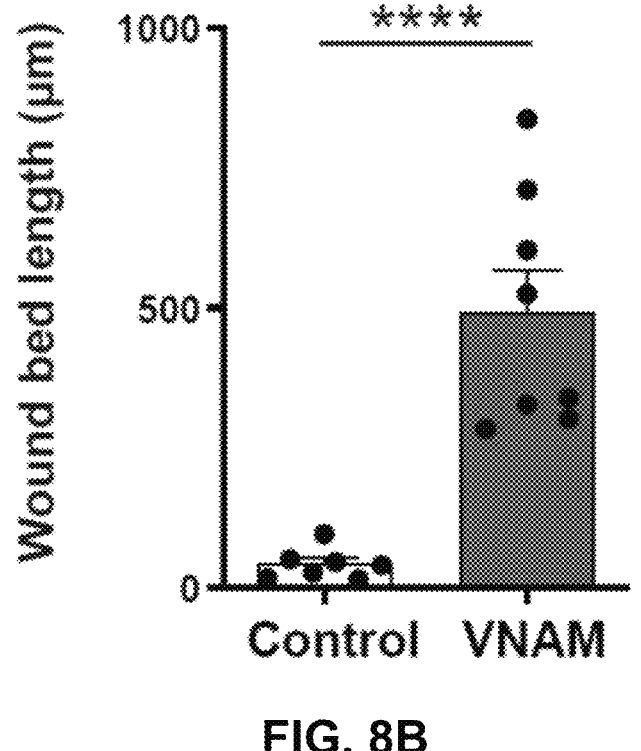
Figure 8C:
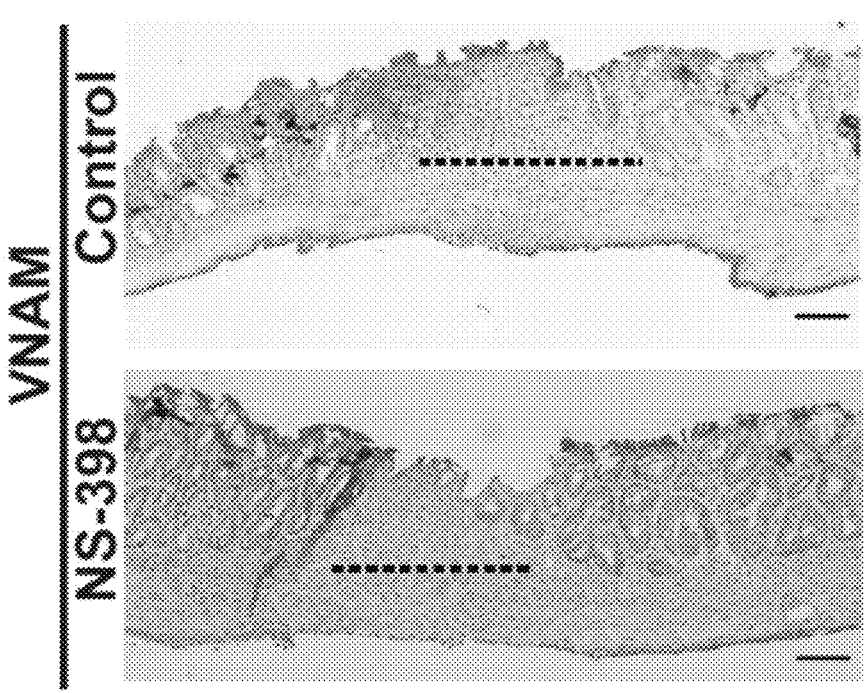
Figure 8D:
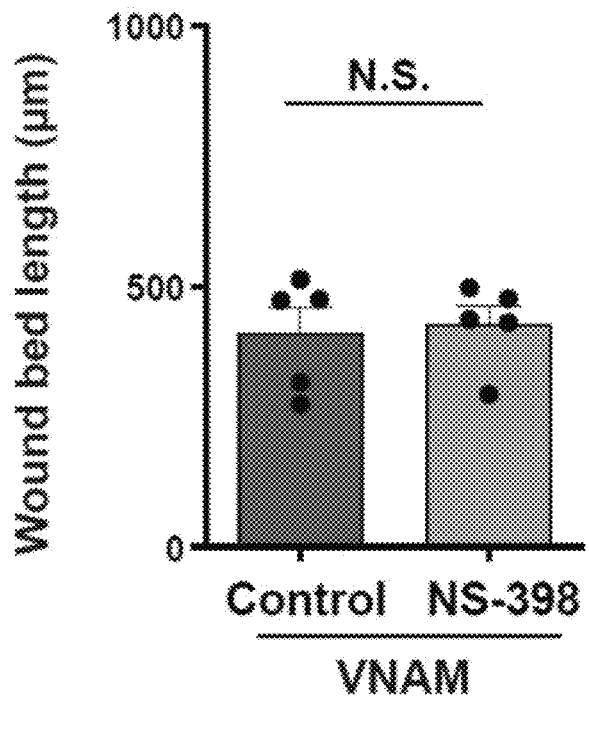
Figure 12A:
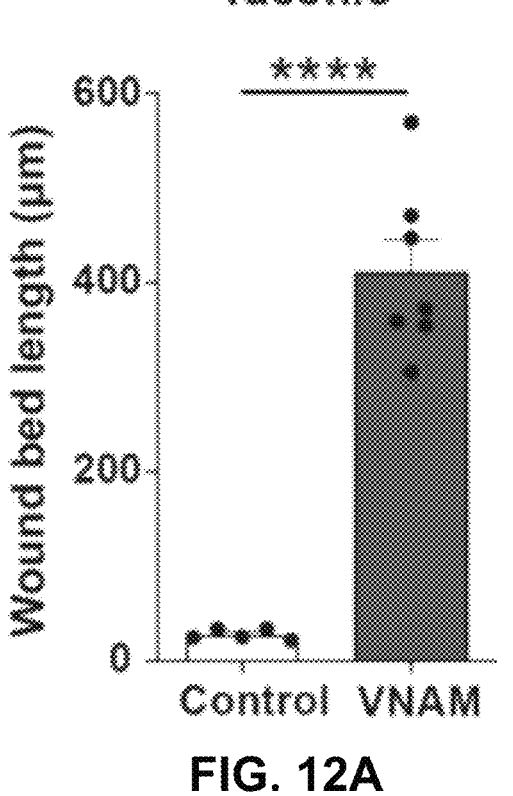
FIG. 12: VNAM associated defects in mucosal healing, epithelial proliferation, and ablation of PGE2 by NS-398 in biopsy injured VNAM pre-treated mice. (A) Quantification of wound bed length at day 12 post-injury in WT SPF mice from Taconic that were administered either a broad-spectrum antibiotic cocktail (Vancomycin, Neomycin, Ampicillin and Metronidazole (VNAM) or Kool-Aid (control) and biopsy injured (n=11-16 wounds/group from 5-7 mice/group from 2 experiments). Significance was determined by unpaired Student's t-test: **p<0.0001. (B-D) WT SPF mice from JAX were administered either a broad-spectrum antibiotic cocktail (Vancomycin, Neomycin, Ampicillin, and Metronidazole (VNAM) or Kool-Aid (control) and biopsy injured. (B) Representative images of crypts adjacent to the wound bed 6 days post-biopsy injury from the indicated groups stained for Ki-67 (proliferating cells), β-catenin (epithelial cells), and bis-benzimide (blue, nuclei). (C) Quantification of Ki-67 positive epithelial cells from mice in (B) (n=17-21 wounds from 6 mice per group from 2 experiments) (D) Wound PGE2 levels at day 6 post-injury in the VNAM administered mice treated with NS-398 or vehicle (control) (n=13-15 wounds/group from 5 mice/group from 2 experiments). Significance was determined by unpaired Student's t-test: p<0.01. All values in (A), (C), and (D) are displayed as mean±SEM.
Figure 12B:
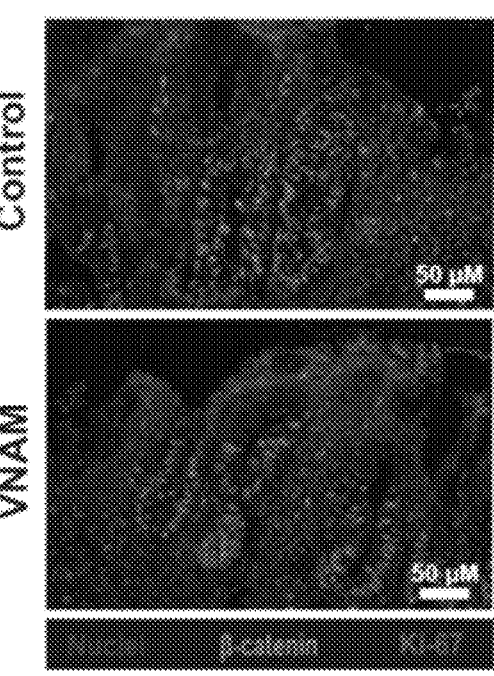
Figure 12C:
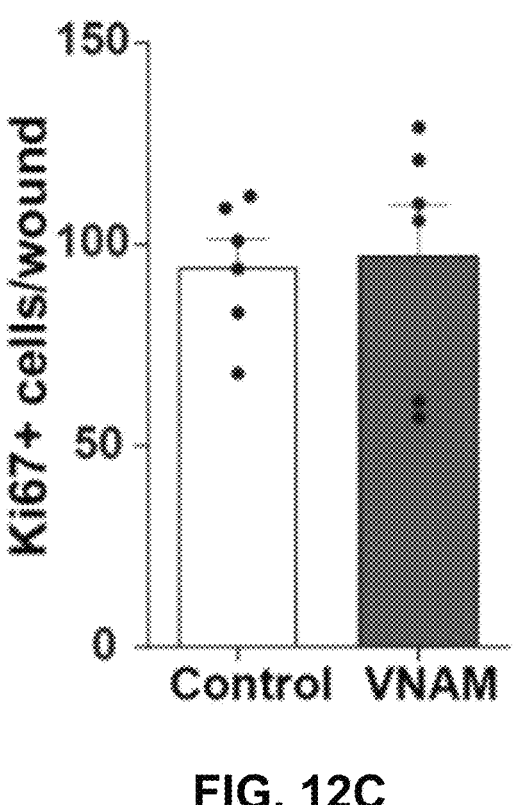
Figure 12D:
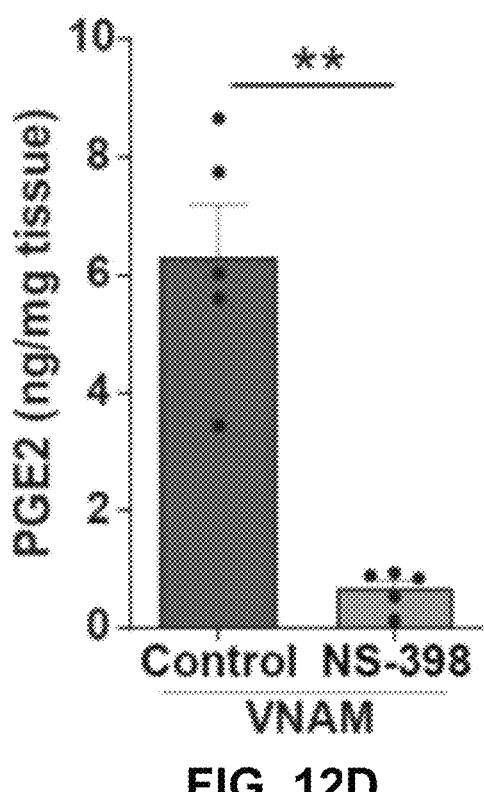

Impaired healing was associated with treatment using a broad-spectrum antibiotic cocktail: vancomycin, neomycin, ampicillin, and metronidazole (VNAM) in WT mice obtained from the two different vendors (FIG. 8A, B and FIG. 12A). The VNAM treatment was neither associated with defects in epithelial proliferation in crypts adjacent to areas of injury, nor could the abnormal wound repair be reversed by inhibition of PGE2 (FIG. 8C, D and FIG. 12B-D), suggesting that additional mechanisms contributed to impaired mucosal healing in VNAM pre-treated mice.

Example 5: Role of Fungal Microbiota in Impaired Mucosal Healing

Multiple lines of evidence suggest that fungi, which can expand in the luminal microbiota following treatment with anti-bacterial compounds may contribute to defective repair post-biopsy injury in VNAM pre-treated mice.

Quantitative PCR was performed on the mice of Ex. 4 to identify fungal microbiota within the intestinal wounds. About three fecal pellets or 10-50 mg samples of intestinal tissue were resuspended in Tris buffer supplemented with 1000 U/ml of lyticase (Sigma), 1 mM EDTA, and 0.2% β-mercaptoethanol (Sigma). DNA was extracted using either the DNeasy PowerLyzer PowerSoil kit (Qiagen) or DNA mini stool extraction kit (Qiagen) according to manufacturer's instructions.

Quantitative PCR was performed using SYBR Green (Roche) or SYBR Green Jumpstart Taq Ready mix (Sigma) on an Eppendorf Mastercycler (Eppendorf) using the following primers as described previously (23, 42, 52)— *Saccharomyces cerevisiae*: forward (5'-AACGGTGAGAGATTTCTGTGC-3', SEQ ID NO:3), reverse (5'-AGCTGGCAGTATTCCCACAG-3', SEQ ID NO:4), *Candida tropicalis*: forward (5'-TTTGGTGGCGG-GAGCAATCCT-3', SEQ ID NO:5), reverse (5'-CGATGCGAGAACCAAGAGATCCGT-3', SEQ ID NO:6), *Debaryomyces hansenii*: forward (5'-GCGACTAT-GAACAGGTTTCCAACGA—3', SEQ ID NO:7), reverse (5'-CCTTCAATGTAACATCAGCGGCCC-3', SEQ ID NO:8) and ITS1-2: forward (5'-CTTGGTCATTTAGAG-GAAGTAA-3', SEQ ID NO:9), reverse (5'-GCTGCGTTCTTCATCGATGC-3', SEQ ID NO:10). The following conditions were used: 94° C. for 10 minutes, followed by 40 cycles of 94° C. for 30 seconds, 55° C. for 30 seconds, and 72° C. for 2 minutes, ending with 72° C. for 30 minutes.

Figure 13A:
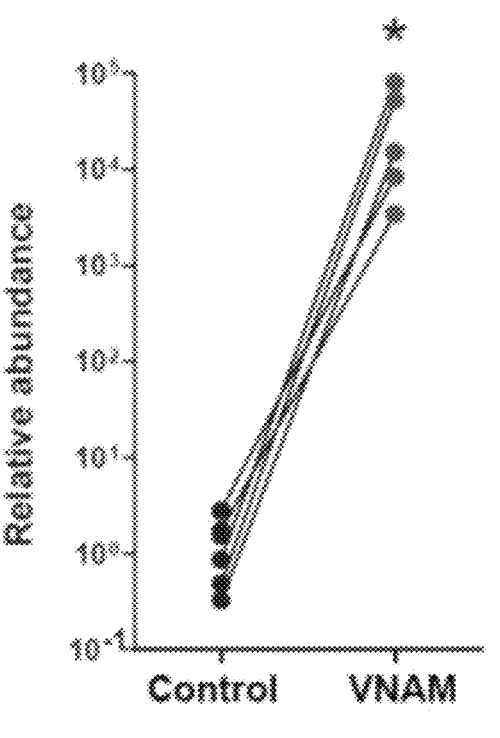
FIG. 13: Increased fungal infiltration in the wounds of VNAM treated mice is reversed by amphotericin B. (A) Genomic DNA was isolated from colonic wounds of control or VNAM fed mice at day 8 post-injury; ITS fungal abundance was analyzed by qPCR and normalized to Gapdh DNA (n=13-19 wounds from 5 mice/group from 2 experiments). Significance was determined by unpaired Student's t-test: *p<0.05. (B) Representative images of day 2 and day 8 wound sections from mice treated with Kool-Aid (control) or VNAM (n=15 wounds from 6 mice/group from 3 experiments) or (C) VNAM in the presence or absence of additional treatment with amphotericin B (n=13 wounds from 6 mice per group from 4 experiments), stained for fungi and bis-benzimide. White arrows denote the presence of fungal antigen in the wound bed (Bars=50 m). Day 2 post-injury represents a time point when the epithelial barrier is still open to the lumen and microbes can freely access the wound area (fungi are detected in all wounds with or without VNAM treatment). In contrast, on day 8, the barrier is completely closed by wound associated epithelial cells and only the microbes that can remain within the wound bed can be detected (fungi are detected only in VNAM treated mice without the addition of amphotericin B).

Quantitative PCR of the ITS region at day 8 post-injury indicated a greater abundance of fungi within intestinal wounds of VNAM pre-treated mice compared to vehicle-treated controls (FIG. 13A).

The anti-*Candida albicans* antibody stains a variety of fungi but does not stain bacteria and therefore was used as an anti-fungal antibody. After overnight incubation, slides were washed in PBS, incubated with secondary antibodies conjugated to Alexa Fluor 594 or 488 (1:500, Invitrogen) for 1 hour at room temperature followed by 3 washes in PBS, counterstaining with bis-benzimide (Hoechst 33258: Invitrogen) and mounting in Fluoromount (Sigma). Zeiss Axio-vert inverted microscope equipped with an Axiocam MRM digital camera was used to visualize and capture images of stained sections. For Ki67 quantification, Ki67 positive cells were counted in high power fields (20×) in 4 crypts adjacent to the wounds on both sides and averaged among all mice per group.

Figure 13B:
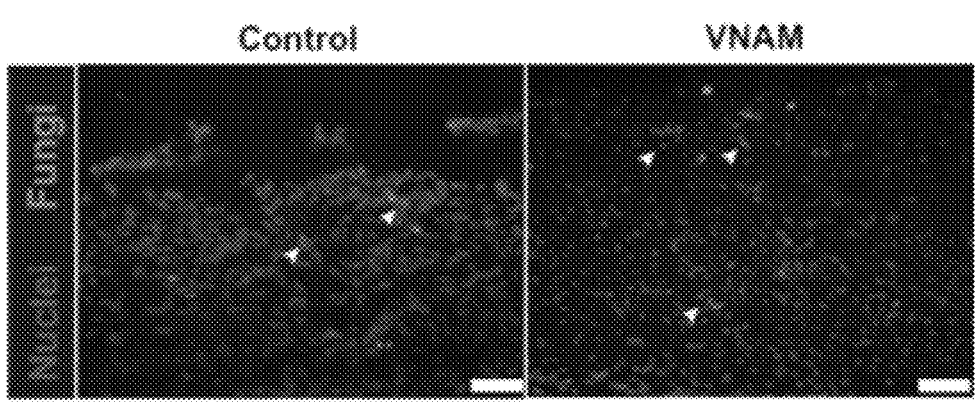

After staining day 8 post-injury sections with the anti-fungal antibody, abundant fungal antigen was detected within all wound sections examined from VNAM pretreated mice; no signal was observed within any wounds of vehicle-treated controls (FIG. 13B).

For antifungal treatment of VNAM-pretreated mice, amphotericin B (0.2 mg/ml in DMSO, Sigma) was orally administered starting 3 days prior to biopsy injury until day 6 post-injury (once daily) and sacrificed on either day 8 or day 12. For antifungal treatment of WT mice (in the absence of VNAM), amphotericin B (0.2 mg/ml in DMSO, Sigma) was orally administered starting 3 days prior to biopsy injury until day 6 post-injury (once daily) and sacrificed on day 12.

Figure 8E:
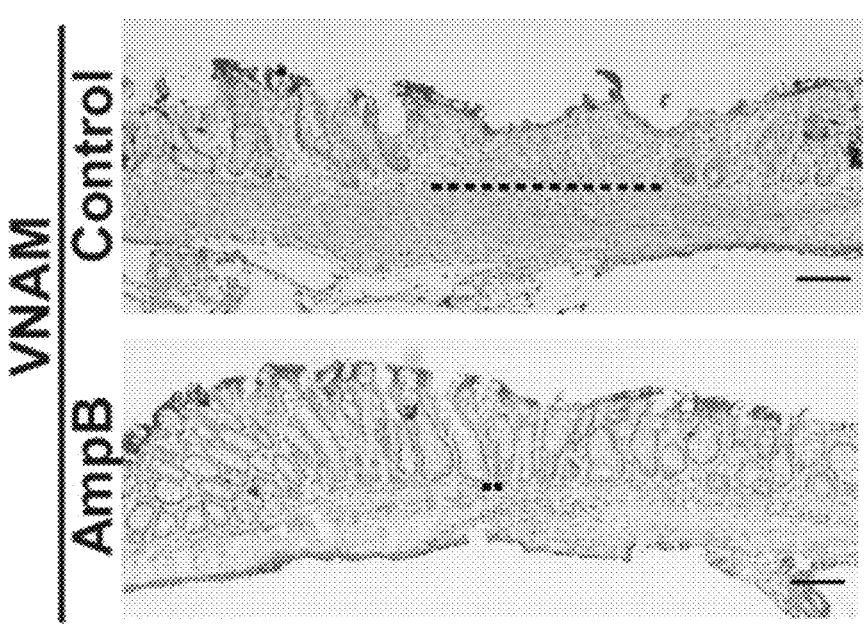
Figure 8F:
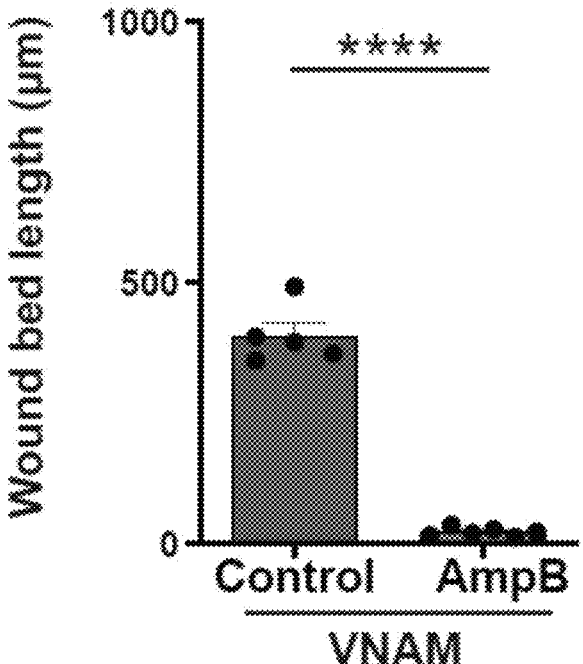
Figure 13C:
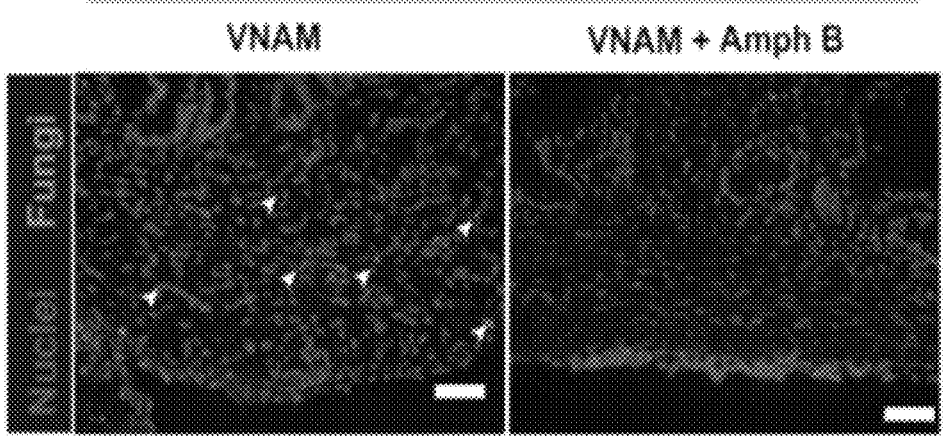

The broad-spectrum antifungal agent amphotericin B reduced fungal antigen detection in the wounds of VNAM-treated mice and reversed the crypt regeneration defects associated with VNAM treatment (FIG. 8E, F and FIG. 13C). Taken together, these data suggest that fungi in the wound bed can inhibit crypt regeneration following injury.

Example 6: Effect of Luminal Microbiota Disturbances on Impaired Mucosal Healing To determine which fungi were enriched following VNAM treatment, we first characterized the luminal myco-biota by isolating DNA from the stool of the VNAM pre-treated mice and controls of Ex. 4, generating ITS amplicons and performing high throughput sequencing.

DNA was isolated using QIAamp 96 DNA QIAcube HT Kit (intestinal tissue and yeast cultures, Qiagen) or DNeasy PowerLyzer PowerSoil kit (stool, Qiagen) according to manufacturer's instructions. High throughput sequencing and analysis for fungal identification from cultures and tissue was performed at GENEWIZ (GENEWIZ, Inc., South Plainfield, NJ). Briefly, 50-100 ng DNA was used to generate amplicons using a panel of primers targeting ITS2 regions designed by GENEWIZ. Besides the ITS target-specific sequences, the primers also contained adaptor sequences allowing uniform amplification of the library with high complexity ready for downstream NGS sequencing on Illumina Miseq platform. For library preparation, end-re-paired adapters were ligated after adenylation of the 3'-ends followed by enrichment by limited cycle PCR. DNA libraries were validated using a DNA 1000 Chip on the Agilent TapeStation (Agilent Technologies, Palo Alto, CA, USA) and were quantified using Qubit 2.0 Fluorometer and mul-tiplexed in equal molar mass. The pooled DNA libraries were loaded on the Illumina instrument according to the manufacturer's instructions. Sequencing was performed using a 2×300/250 paired-end (PE) configuration; image analysis and base calling were conducted by the MiSeq Control Software (MCS) embedded in the MiSeq instrument.

The QIIME data analysis package was used for ITS data analysis. The forward and reverse reads were joined and assigned to samples based on barcode and truncated by cutting off the barcode and primer sequence. Quality filtering on joined sequences was performed and sequences which did not fulfill the following criteria were discarded: sequence length=20. Then the sequences were compared with the reference database (RDP Gold database) using the UCHIME algorithm to detect chimeric sequences, and then the chimeric sequences were removed. The effective sequences were used in the final analysis. Sequences were grouped into operational taxonomic units (OTUs) using the clustering program VSEARCH (1.9.6) against the UNITE ITS database pre-clustered at 97% sequence identity. The Ribosomal Database Program (RDP) classifier was used to assign a taxonomic category to all OTUs at a confidence threshold of 0.8. High throughput ITS sequencing and analysis of mouse stool including DNA extraction, sequencing, and analysis were performed by investigators blinded to the treatments.

For the quantification of bacteria and yeast in stool, relative abundance was calculated by normalizing the $\Delta Ct$ values to the amount of DNA used in the reaction as described previously. For quantification of yeast in intestinal tissue, relative abundance was calculated by the $\Delta Ct$ method and normalized to the amount of Gapdh.

There was significant inter-individual variation in the mycobiota composition of both control and VNAM-treated mice. We did not observe a significant difference in the relative abundance of any detectable fungal genera between these two groups (FIG. 14). We next evaluated the mycobiota of mucosal wounds from control and VNAM-pretreated mice to determine if its composition indeed reflected the highly variable luminal mycobiota. High throughput sequencing of ITS amplicons obtained from wounds identified, in sharp contrast to luminal data, a single dominant genus, *Debaryomyces*, in the VNAM pretreated mice but not controls (FIG. 9A, B).

Figure 9A:
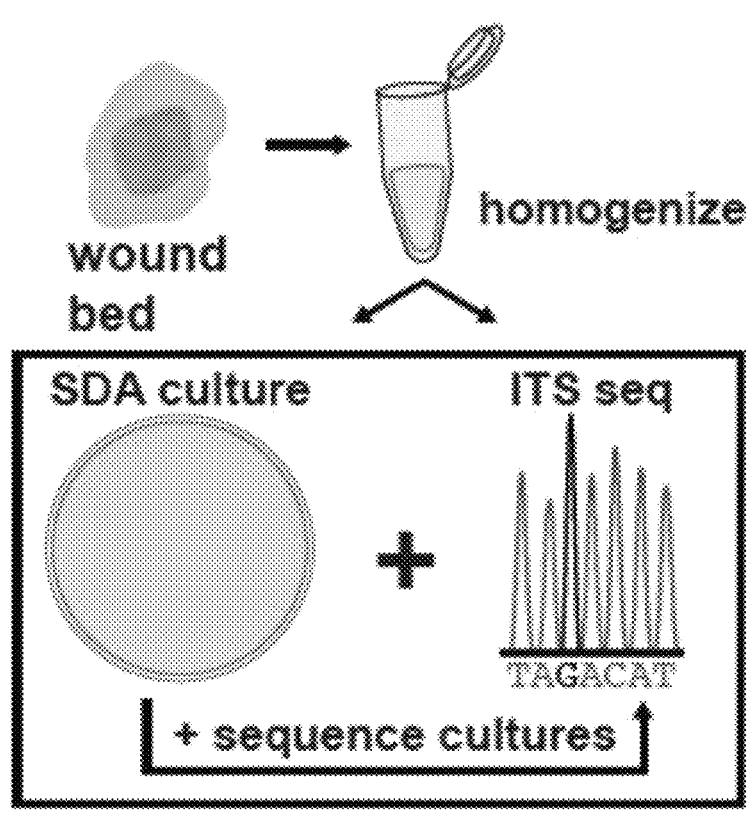
FIG. 9: Debaryomyces was enriched in wounds of VNAM pre-treated mice, and its administration to conventionally-raised or gnotobiotic mice led to impaired crypt regeneration. (A-E) Mice were treated with VNAM or Kool-Aid (vehicle control) followed by biopsy injury. Wounds were collected on day 8 post-injury for fungal analysis. (A) Schematic representation of the procedures for analysis of fungal abundance. (B) Relative abundance of fungi in the wounds of control and VNAM groups as evaluated by high throughput sequencing of tissue DNA. Data for individual mice are shown with relative abundance of different genera on the y-axis. C indicates control and V indicates VNAM. (C) Representative images of colonies growing on SDA plates and (D) counts of viable colonies (n=14-16 wounds/group from 4-6 mice/group). No growth was observed from control wounds. (E) Identification of fungi assessed by ITS sequencing of the pooled colonies per mouse growing in (C and D). All colonies were identified as Debaryomyces. (F-H) SPF WT mice were gavaged with either PBS (controls), *D. hansenii*, or *S. cerevisiae* and biopsy injured. (F) Experimental set up for procedures and analysis. (G) Representative images of H&E stained sections (Bars=100 μm) and (H) quantification of wound bed length at day 12 post-injury (n=13-19 wounds/group from 6-8 mice/group). (I-K) SPF WT mice gavaged with either PBS (control), *D. hansenii*, or *C. tropicalis* were exposed to DSS for 7 days followed by two weeks of recovery (no DSS). (I) Experimental set up displaying time course of gavage and DSS treatment. (J) Representative images of H&E stained sections and (K) percent colonic crypt loss in the indicated groups of mice (n=5-7 mice/group). Significance was determined by one-way ANOVA and TUKEY's post hoc test: ****p<0.0001. All values in D, H, and K are displayed as mean±SEM. The dashed black line in G at the center of the wound represents wound bed length (largest distance between the crypts). Bars=100 μm.
Figure 9B:
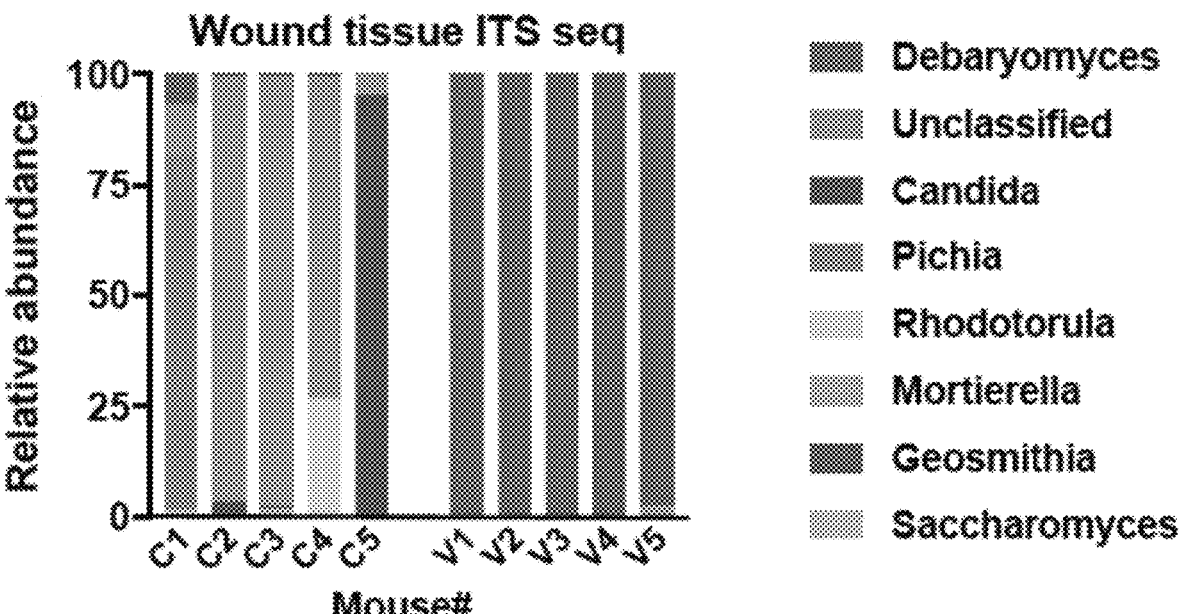

To determine if the sequencing represented live or dead fungi, we cultured wound beds using fungal selective Sabouraud dextrose agar (SDA) plates (FIG. 9A). Biopsy wounds were lightly scraped with a coverslip to remove luminal contents adhered to the tissue. The tissues were then extensively washed in sterile PBS containing ampicillin (Sigma), and manually homogenized using Disposable Tissue Grinder Pestle (Corning). The homogenate was then streaked on SDA plates supplemented with ampicillin followed by incubation at 30° C. for 3 days. All colonies growing on one plate were pooled in a microfuge tube and the relative abundance of different yeasts at genus level per sample was estimated by high throughput sequencing of the ITS amplicons.

Figure 9C:
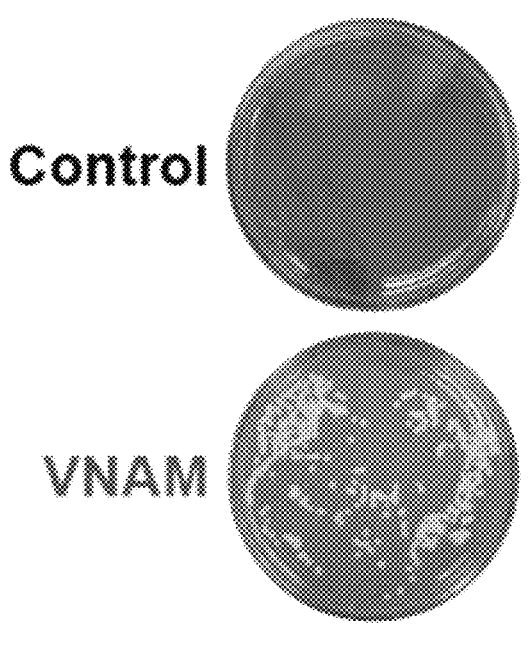
Figure 9D:
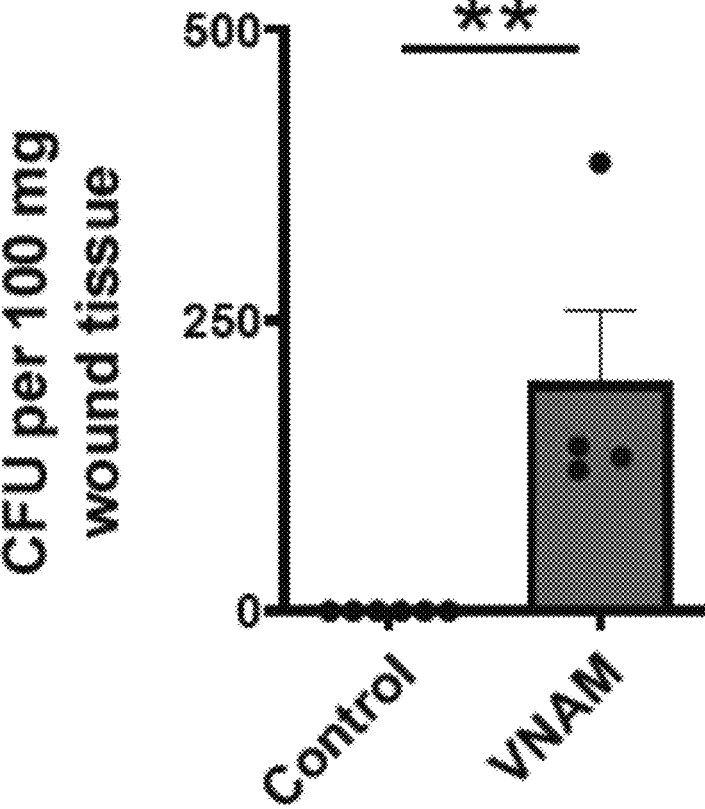
Figures 9E, 9F:
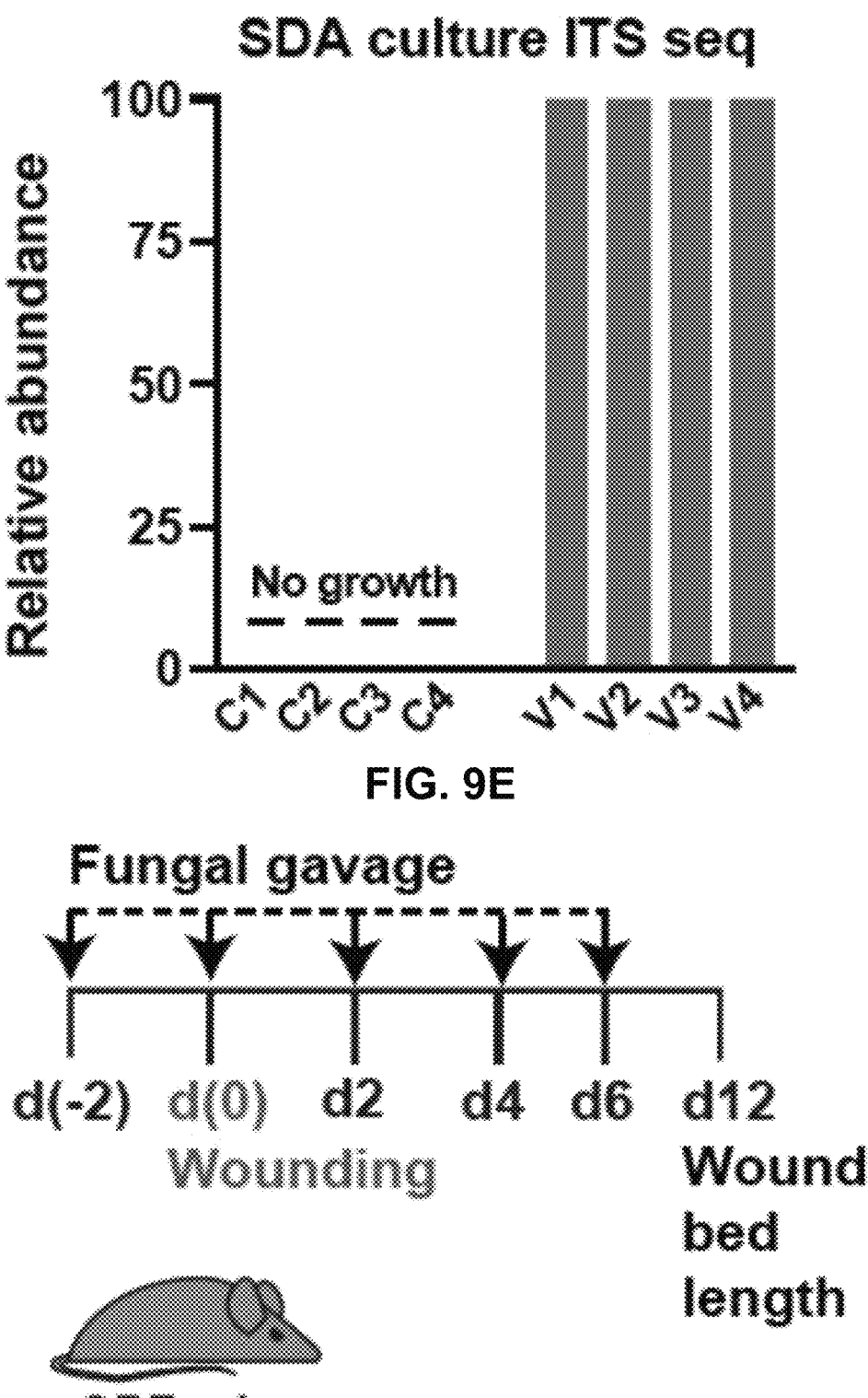

All of the wound homogenates tested from VNAM-pretreated mice contained viable fungal colonies (FIG. 9C). In contrast, none of the wounds from control mice contained fungi (FIG. 9C, D). ITS sequencing of pooled colonies confirmed that the viable colonies obtained from the VNAM-pretreated mice were *Debaryomyces* (FIG. 9E). Further speciation in the genus *Debaryomyces* required additional sequencing of the ACT1 locus, which previously was used to differentiate *Debaryomyces* species. Sequencing of ACT1 showed that individual *Debaryomyces* isolates obtained from the wounds of VNAM-pretreated mice showed a 100% sequence identity to *Debaryomyces hansenii* (also known as *Candida famata*) (FIG. 15 and Table 1).

TABLE 1

| Debaryomyces isolates obtained from VNAM treated mice identified via ACT1 sequencing | | |
| --- | --- | --- |
| Mouse # | Isolate name | Identity |
| 1 | B6A1 | Debaryomyces hansenii |
| 2 | B6B1 | Debaryomyces hansenii |
| 3 | B6C1 | Debaryomyces hansenii |
| 4 | B6D1 | Debaryomyces hansenii |
| 5 | B6E1 | Debaryomyces hansenii |
| 6 | B6F1 | Debaryomyces hansenii |

Example 7: Effect of *Debaryomyces hansenii* on Impaired Mucosal Healing

To investigate if administration of *D. hansenii* was sufficient to impair mucosal healing in conventionally-raised WT mice that were not pre-treated with antibiotics, the following experiments were conducted.

For inoculation experiments, yeasts were expanded in Sabouraud dextrose agar (SDA) for 2-4 days at 30° C. prior to gavage. Mice were gavaged with pure culture of *D. hansenii* (obtained from the wounds of antibiotic-treated mice or inflamed tissues of Crohn's disease) or *Saccharomyces cerevisiae* (ATCC) at ~106 CFU/mouse, unless otherwise stated, in 150 μl of PBS. Controls received PBS only. For all inoculation experiments, gavage occurred 2 days before injury, on the day of injury, and 2, 4, and 6 days post-injury unless otherwise stated.

Figures 9G, 9H:
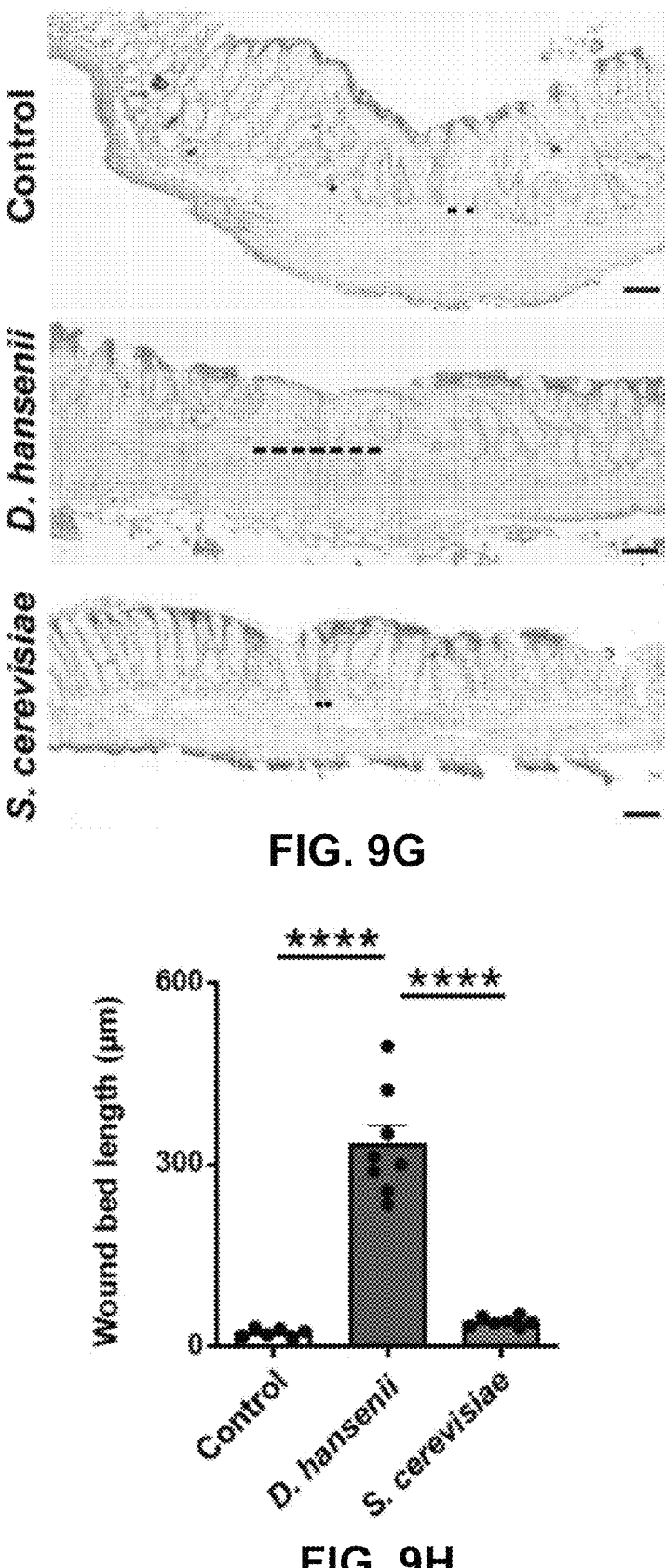
Figures 16D, 16E, 17A:
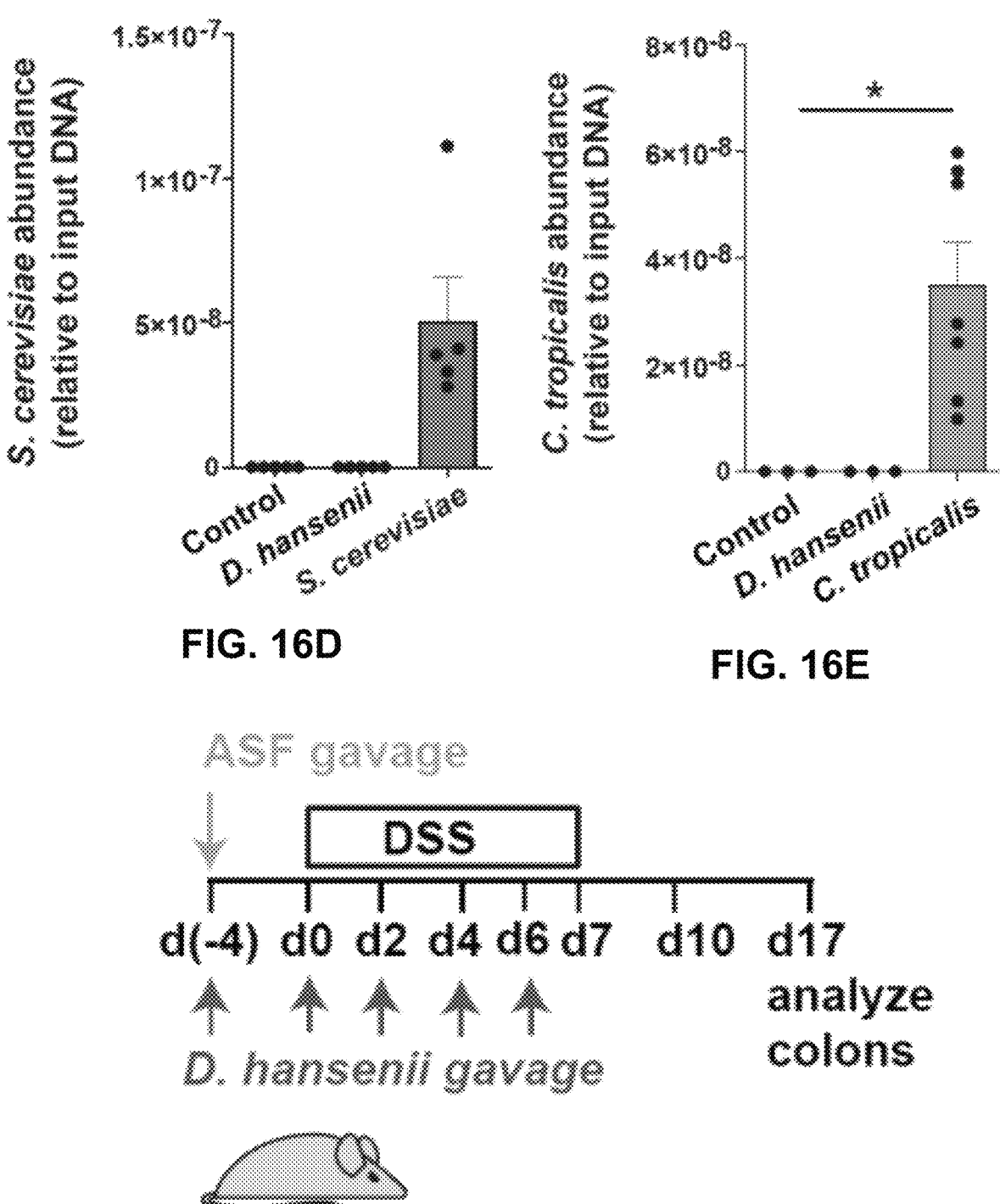
FIG. 16: *D. hansenii* effectively colonizes the wounds of injured SPF WT mice. WT SPF mice were gavaged with *D. hansenii* or PBS (control) then biopsy injured. (A) Schematic representation of the procedures for isolation of and gavage with *D. hansenii*. The gavage and biopsy protocols are identical to that depicted in FIG. 9F. Day 8 wounds from the control and *D. hansenii*-gavaged mice were homogenized and plated on SDA medium. (B) Colony counts and (C) identification of yeast assessed by ITS sequencing of the pooled colonies (n=13-17 wounds/group from 4-7 mice/group from 2 experiments). (C) The majority of the colonies belonged to the genus Debaryomyces with less than 0.05% identified as *Candida, Filobasidium*, and an unclassified genus (note D1, D2, D3, and D4 only show *D. hansenii*). Data is broken down to individual mice on the x-axis. C=control mice and D=*D. hansenii*-gavaged mice. (D) Levels of *S. cerevisiae* and (E) *C. tropicalis* in the lumen of mice gavaged with the indicated species on the X-axis. Relative abundance is plotted and determined by species-specific PCR of stool DNA (relative to the amount of input DNA, n=3-7 mice per group from 2 experiments). Significance was determined by one-way ANOVA and Tukey's post-test: *p<0.05.
FIG. 17: *D. hansenii* did not alter colonization by 8 ASF bacteria in gnotobiotic mice. Germ-free mice pre-colonized with Altered Schaedler flora (ASF) were gavaged with or without *D. hansenii* and exposed to DSS followed by recovery. (A) Experimental set up for procedures and analysis. (B) Bacterial and (C) yeast DNA abundance in the stool of indicated groups of mice as determined by quantitative PCR (relative to input DNA in a PCR reaction, n=3-4 mice per group from 2 experiments). Significance was determined by one-way ANOVA and Tukey's post hoc test: **p<0.01. N.S. indicates not significant. (D) Relative abundance of 8 ASF bacteria in the presence or absence of *D. hansenii* as evaluated by qPCR (n=5 mice per group from 2 experiments). All values in B, C, and D are displayed as mean±SEM. Significance was determined by unpaired Student's t-test. N.S. indicates not significant.

Conventionally-raised WT mice were gavaged with *D. hansenii* (isolate B6A1) before and after biopsy injury (FIG. 9F and FIG. 16A). Viable *D. hansenii* was recovered from wound homogenates of WT mice gavaged with *D. hansenii*, whereas no growth was observed in wound homogenates from controls (FIG. 16B, C). Importantly, colonization of wounds with *D. hansenii*, but not *Saccharomyces cerevisiae*, a yeast commonly found in human gut microbiota (27), impaired crypt regeneration (FIG. 9G, H and FIG. 16D).

Figure 9I:
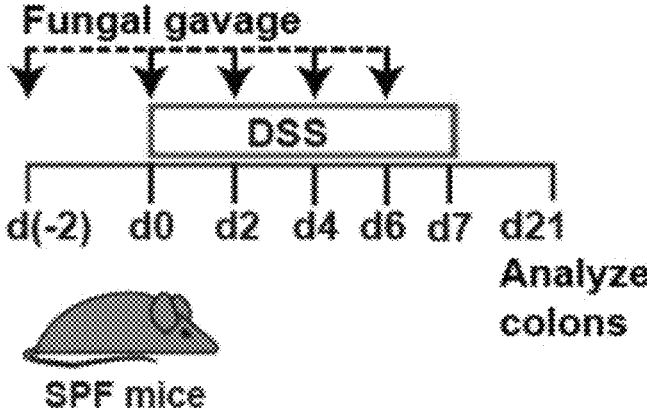

To determine if our findings were specific to the biopsy injury model or were generalizable to other types of damage, we studied the effects of *D. hansenii* on mucosal healing after dextran sodium sulfate (DSS)-induced colonic mucosal damage (FIG. 9I). Mice were given 2.5% dextran sulfate sodium (DSS) (TdB Consultancy) in drinking water for 7 days followed by 10 (germ free mice) or 14 days (SPF mice) of recovery. Germ-free mice were colonized with Altered Schaedler Flora (Taconic) before induction of DSS colitis. To this end, 3-5 fecal pellets obtained from ASF donor mouse (Taconic) were resuspended in sterile PBS and germ-free mice were immediately gavaged with ~150 μl of the suspension. ASF colonization was confirmed by qRT-PCR using primers described elsewhere. In some experiments, ASF pre-colonized germ-free mice were gavaged with 106 CFU of *D. hansenii* in ~150 μl of PBS on indicated days. In some experiments, monocolonization of germ-free mice was achieved by gavaging with 106 CFU of D *hansenii* in ~150 μl of PBS four days before the start of DSS. *D. hansenii* monocolonized germ-free mice and controls (PBS) were administered 1.5% DSS in drinking water for 7 days followed by 10 days of recovery.

Figure 9J:
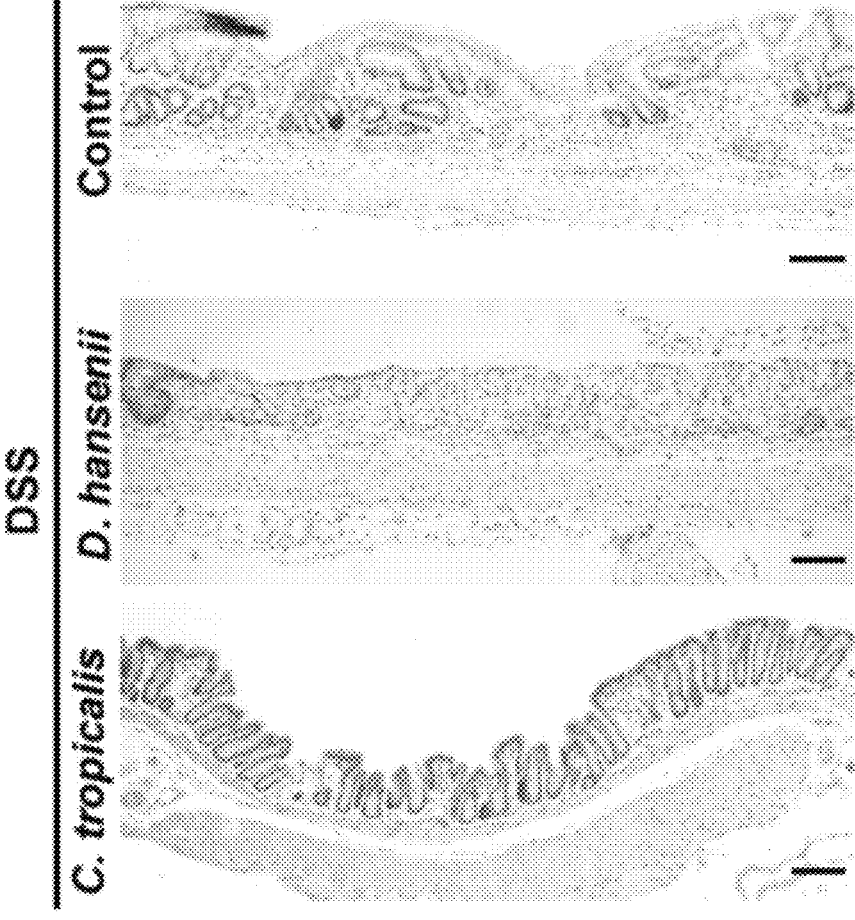
Figure 9K:
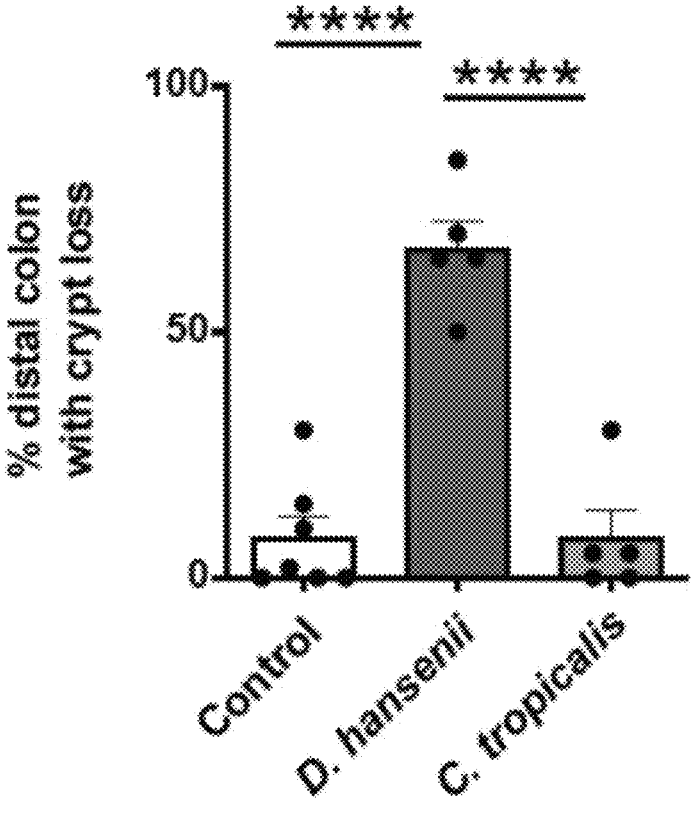
Figures 17B, 17C, 17D:
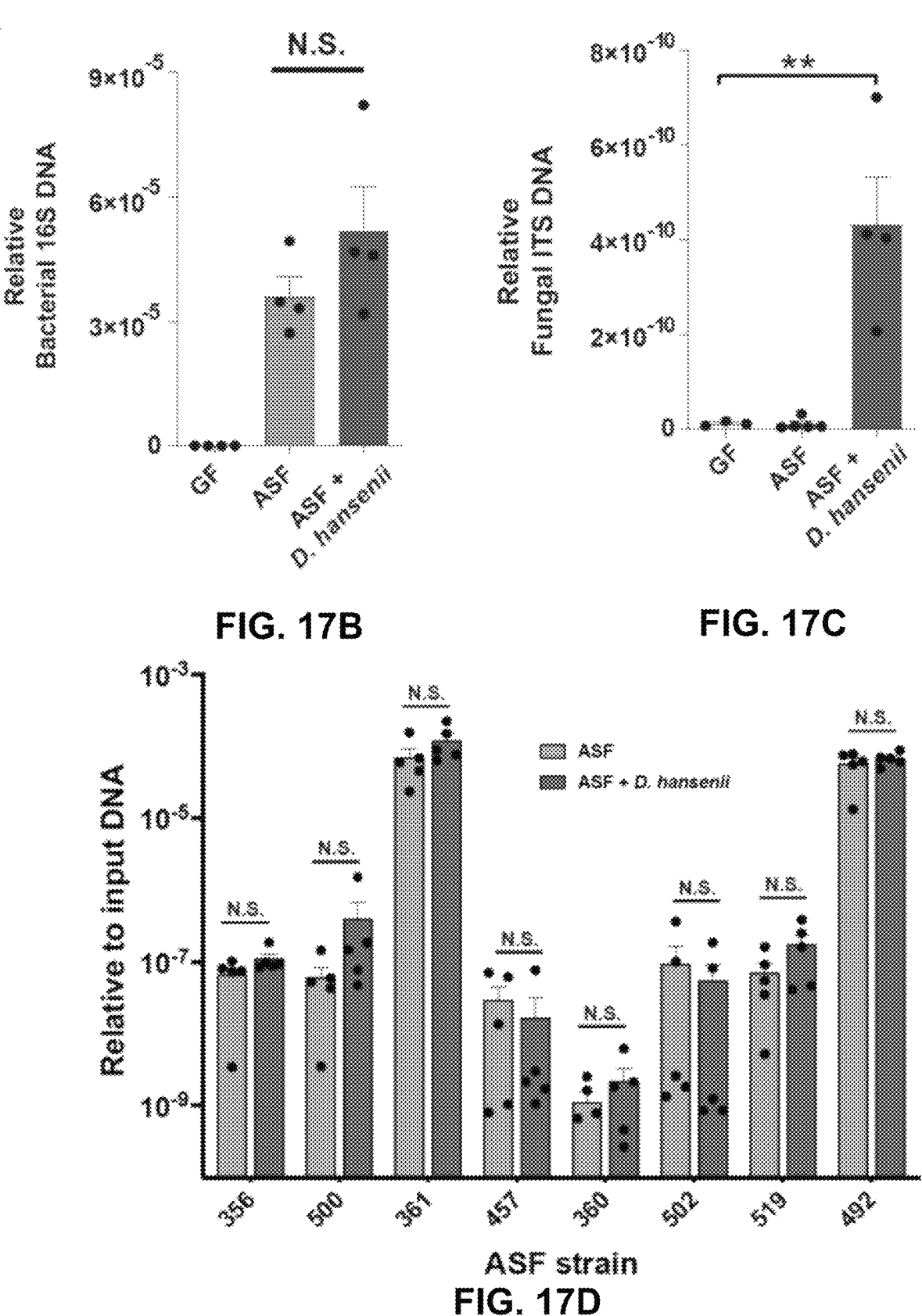
Figure 18A:
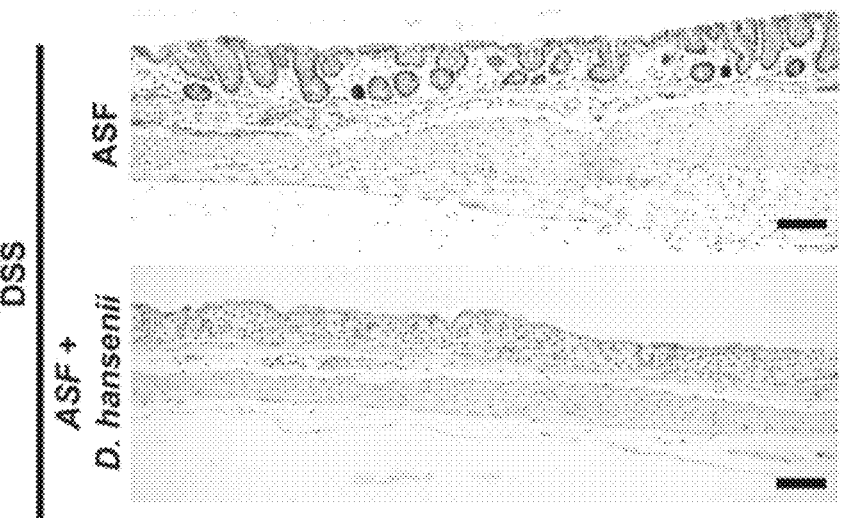
FIG. 18: *D. hansenii* impaired crypt regeneration in ASF colonized gnotobiotic and monocolonized GF mice. (A) Representative images of H&E stained sections of colon from the indicated groups of mice and severity of colon damage evaluated by (B) crypt loss (n=6-7 mice per group from 3 experiments). Significance was determined by unpaired Student's t-test: ****p<0.0001. (C-D) Germ-free mice were monocolonized with *D. hansenii* or treated with PBS (control group), exposed to 1.5% DSS, and healing was evaluated 10 days post-DSS withdrawal. (C). Representative images of H&E stained sections of colon from the indicated groups of mice and severity of colon damage evaluated by (D) percent crypt loss in the distal colon (n=5 mice/group from 2 experiments). Significance was determined by unpaired Student's t-test: **p<0.01. All values in B and D are displayed as mean±SEM. Bars=100 μm.
Figure 18B:
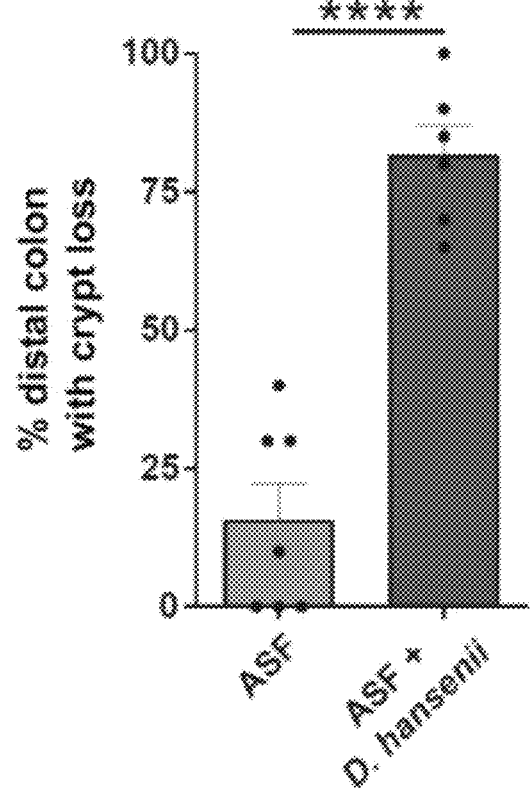
Figure 18C:
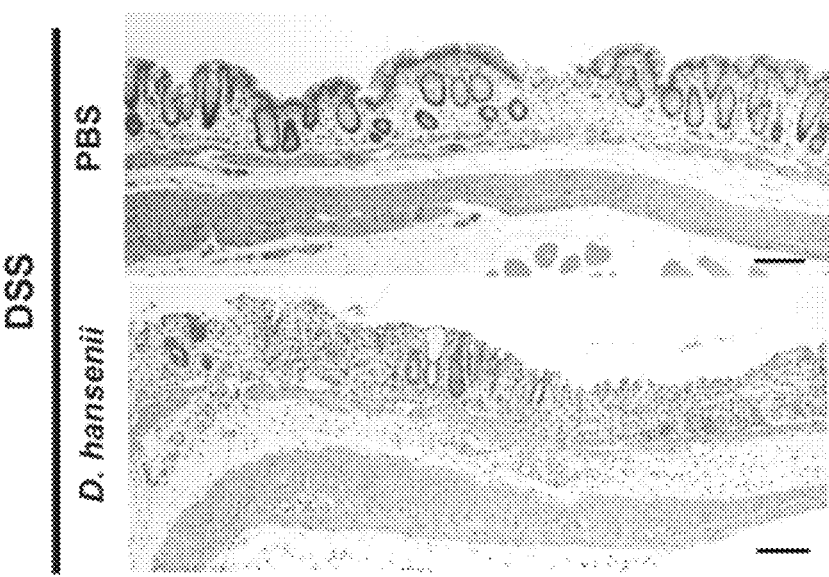
Figure 18D:
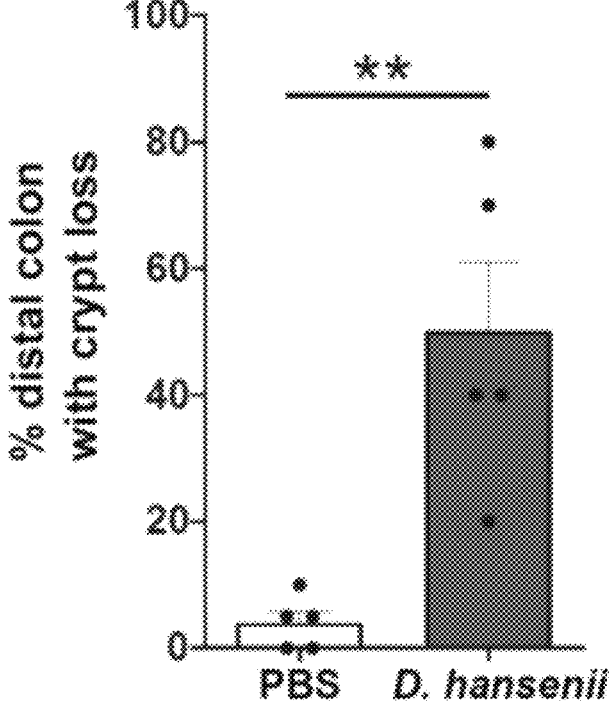

Mice gavaged with *D. hansenii*, showed more extensive mucosal ulceration and increased crypt loss after the recovery phase following cessation of DSS treatment (FIG. 9J, K and FIG. 16E), compared to controls or mice gavaged with *C. tropicalis*, a fungus enriched in the lumen of CD subjects. We also utilized gnotobiotic mice in this injury model. Germ-free mice were colonized with altered Schaedler flora (ASF), a defined bacterial consortium, then treated with DSS in the presence or absence of *D. hansenii* (FIG. 17A-C). *D. hansenii* colonization did not alter the levels of any of the eight ASF bacteria (FIG. 17D). Furthermore, *D. hansenii* impaired healing post DSS injury in ASF colonized gnoto-biotic mice, characterized by extensive crypt loss (FIG. 18A, B). Finally, oral inoculation of GF mice with *D. hansenii*, in the absence of ASF bacteria, also impaired wound healing post DSS injury (FIG. 18C, D). These studies demonstrate, with multiple models of intestinal injury and repair, that *D. hansenii* fulfills Koch's postulates and is sufficient to impair wound healing in the intestine.

Example 8: Mechanisms of Mucosal Healing Impairment by *Debaryomyces hansenii*

To determine the mechanism by which *D. hansenii* impairs healing, experiments were conducted to establish the cell type that *D. hansenii* preferentially localizes with in vivo.

Immunofluorescence analysis was used to assess wound tissues as described below. OCT-embedded fresh frozen wounds were cut using a cryostat to obtain 5 μm sections. The sections were fixed in ice-cold 4% PFA for 15 minutes, followed by blocking in 3% BSA/0.5% Triton-X for 1 hour at room temperature. After blocking, sections were incubated with primary antibodies at 4° C. overnight. The following primary antibodies were used: mouse monoclonal anti-βcatenin (1:2000, BD Transduction Laboratories), rabbit polyclonal anti-*Candida albicans* (1:500, Meridian Life Sciences), rat monoclonal anti-Ki67 (Thermo Fisher Scientific), rat monoclonal anti-Ly-6 G (1:500, BD Pharmingen), rabbit monoclonal anti Cd11c (1:200, Cell Signaling Technology), rat monoclonal Alexa Fluor 488 anti B220 (1:500, BioLegend), rabbit polyclonal anti CD3 (1:500, Abcam), rat monoclonal anti-mouse CD45 (1:200, BD Biosciences) and rat monoclonal anti F4/80 (1:200, Abcam). After overnight incubation, slides were washed in PBS, incubated with secondary antibodies conjugated to Alexa Fluor 594 or 488 (1:500, Invitrogen) for 1 hour at room temperature followed by 3 washes in PBS, counterstaining with bis-benzimide (Hoechst 33258: Invitrogen) and mounting in Fluoromount (Sigma). Zeiss Axiovert inverted microscope equipped with an Axiocam MRM digital camera was used to visualize and capture images of stained sections. For Ki67 quantification, Ki67 positive cells were counted in high power fields (20×) in 4 crypts adjacent to the wounds on both sides and averaged among all mice per group.

Figure 19A:
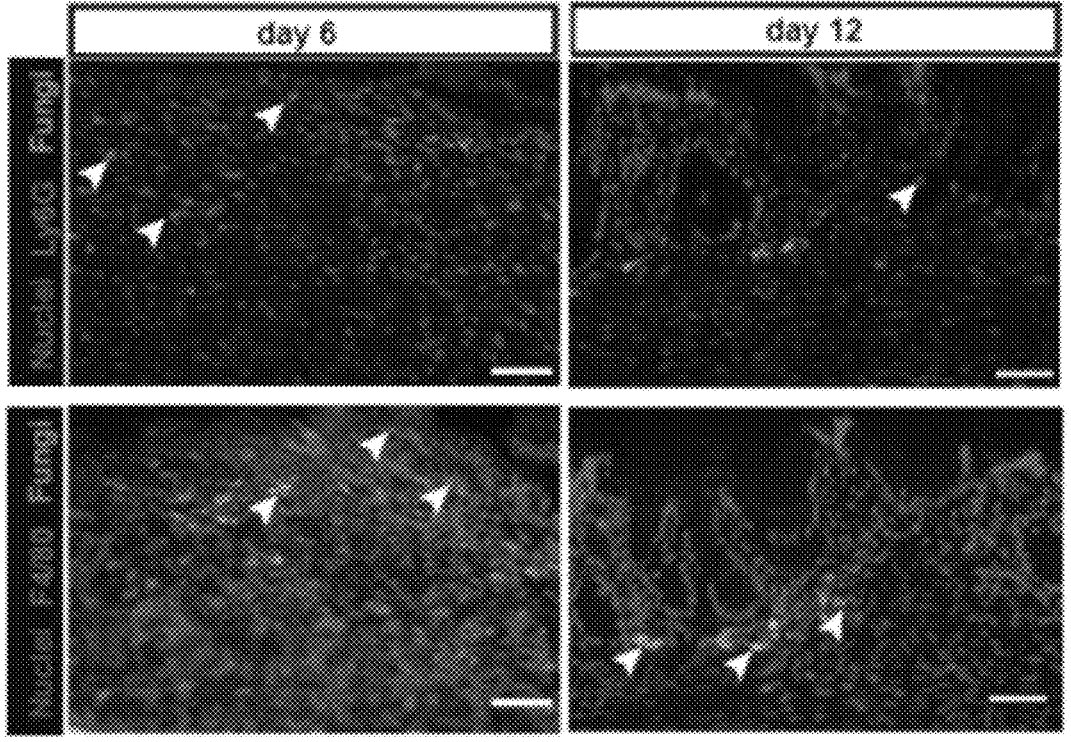
FIG. 19: *D. hansenii* preferentially associates with F4/80 positive macrophages in the colonic wounds of mice. (A) Representative images of wounds (day 6 and 12 post-injury) from VNAM treated mice stained with an anti-fungal antibody, anti Ly6G antibody (upper panel), anti-F480 antibody (lower panel), and bis-benzimide (nuclei) (n=16 wounds from 6 mice per group from 3 experiments). Bars=50 μM. White arrows in the upper panel indicate neutrophils that are away from fungi whereas white arrows in the lower panel denote macrophages that closely associate with fungi in the wound bed. (B) WT mice were intra-rectally administered rhodamine labeled *D. hansenii*, biopsy injured, and wounds. Representative images stained with an anti-F480 antibody (macrophages), and bis-benzimide (nuclei) (n=11 wounds from 5 mice from 2 experiments). Negative controls with PBS gavage showed no signal for *D. hansenii*. Bars=10 μM. White arrows represent *D. hansenii* colocalization with cells expressing F4/80. (C) Relative abundance of genera of all viable colonies from the fungal culture of CD45+F480+ cells sorted from the wounds of *D. hansenii* infected, DSS recovery model as in FIG. 10A identified by ITS sequencing. Data for relative abundance are broken down by individual mice on the x-axis. Data are displayed as mean±SEM. (D) Representative images of day 12 wounds from biopsy injured WT SPF mice infected with or without *D. hansenii* stained for different immune cells (CD45: immune cells, F4/80: macrophages, CD3: T cells, B220: B cells, Ly6g: neutrophils, CD11c: dendritic cells) and bis benzimide (nuclei) (n=27-39 wounds from 9-12 mice per group from 4 experiments). Bars=50 μM. (E) Quantification of cells from the groups in (D). Significance was determined by two-way ANOVA and TUKEY's post-hoc test: ****p<0.0001. All values are displayed as mean±SEM.
Figure 19B:
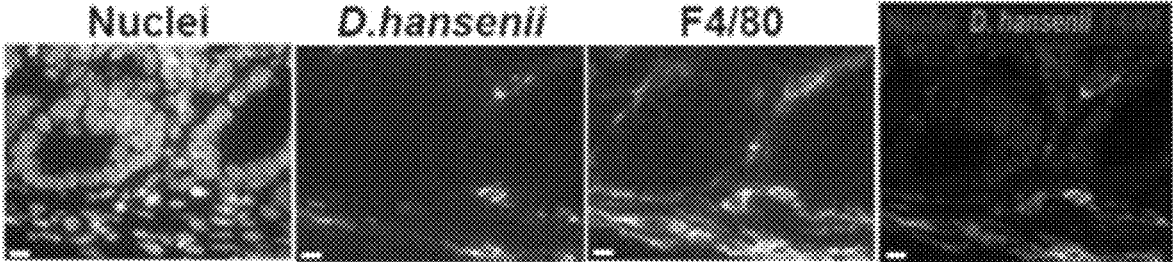

Immunofluorescence analysis of VNAM treated colonic wounds, where *Debaryomyces* is the dominant fungus detected (FIG. 2B, E), indicated that majority of intracellular fungi were located within F4/80+ macrophages as compared to Ly6G positive neutrophils (FIG. 19A). We also found that pre-labeled *D. hansenii*, when administered to biopsy injured WT mice, preferentially co-localized with F480+ macrophages (FIG. 19B).

Wound bed cells of *D. hansenii* infected WT mice were sorted using cell cytometry as described below. Colons were flushed with Ca2+/Mg2+ free PBS and cells were isolated. Briefly, colons were opened longitudinally, cut open in 2 cm pieces, and incubated in HBSS (Invitrogen) with 2 mM EDTA (Sigma) at 37° C. for 20 minutes in a shaker. After two washes in EDTA, colons were cut into small pieces using sterile scissors and digested completely in HBSS containing collagenase type VIII (1.5 mg/ml, Sigma) and DNase I (40 μg/ml, Roche) while incubating at 37° C. for 30 minutes in a shaker. Cells were then passed through a sterile filter and resuspended in 5% FBS in PBS. Cells were then stained with Fc block (anti CD16/32, BioLegend)) for 15 minutes followed by staining with fluorescently labeled antibodies: CD45 (BioLegend; Rat anti-mouse, 30-F11), F480 (BioLegend; Rat anti-mouse, BM8). Next, the cells were washed, resuspended in fresh PBS containing 5% FBS, and stained with 7-AAD. 7-AAD was added 5 minutes before sorting. Cells were gated on singlets followed by live cells and sorted into three distinct populations: CD45+ F480+, CD45+F480−, CD45−F480− Sorting was performed on a modified Sony Synergy SY3200 (Sony Biotechnology, San Jose, CA) updated to 24 parameters. Software used for acquisition was Winlist version 8 (Verity Software House, Topsham, ME). Sorted cells were collected in PBS containing 80% FBS, allowed to sit on ice for 30 minutes followed by resuspension in either lysis buffer for RNA extraction or water for fungal culture on SDA plates.

Figure 19C:
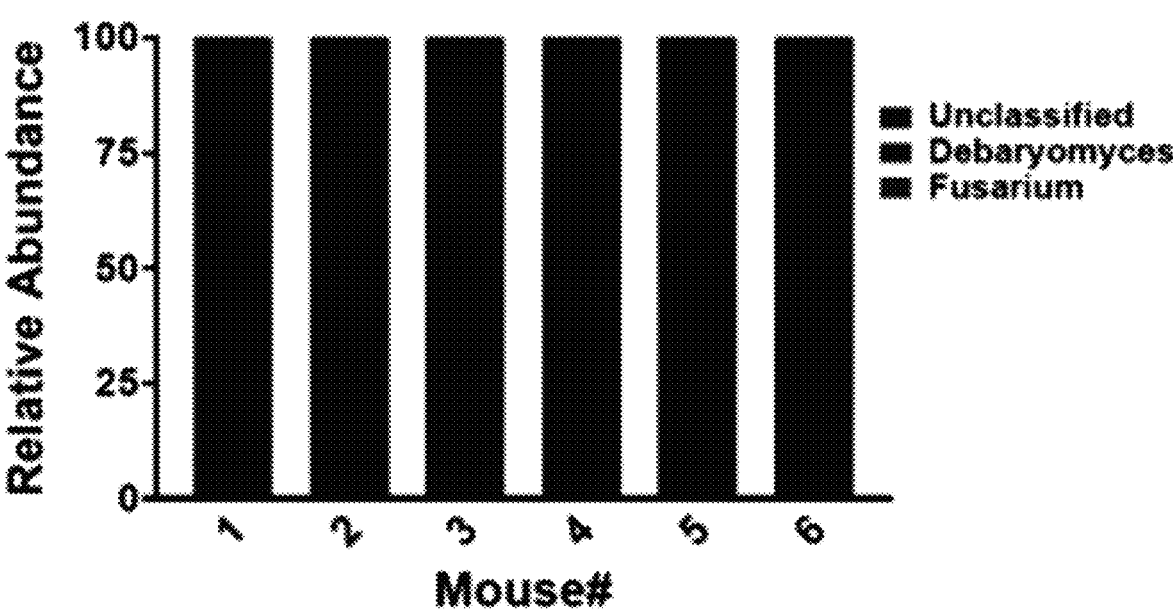
Figure 19D:
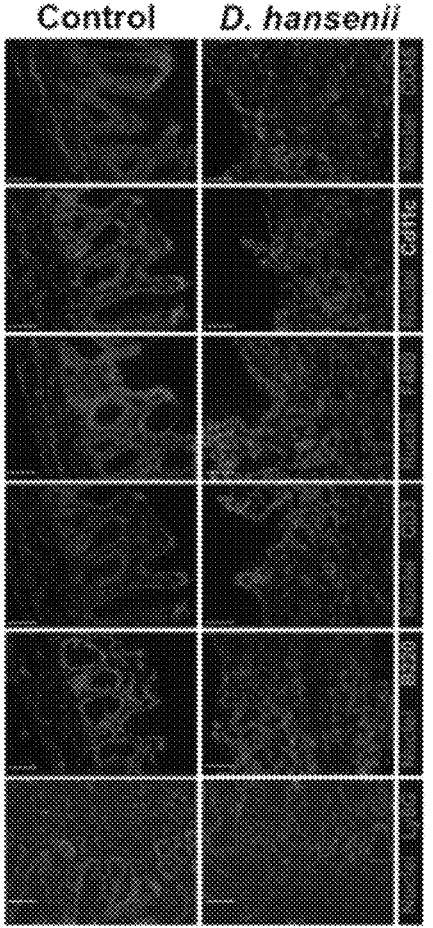
Figure 19E:
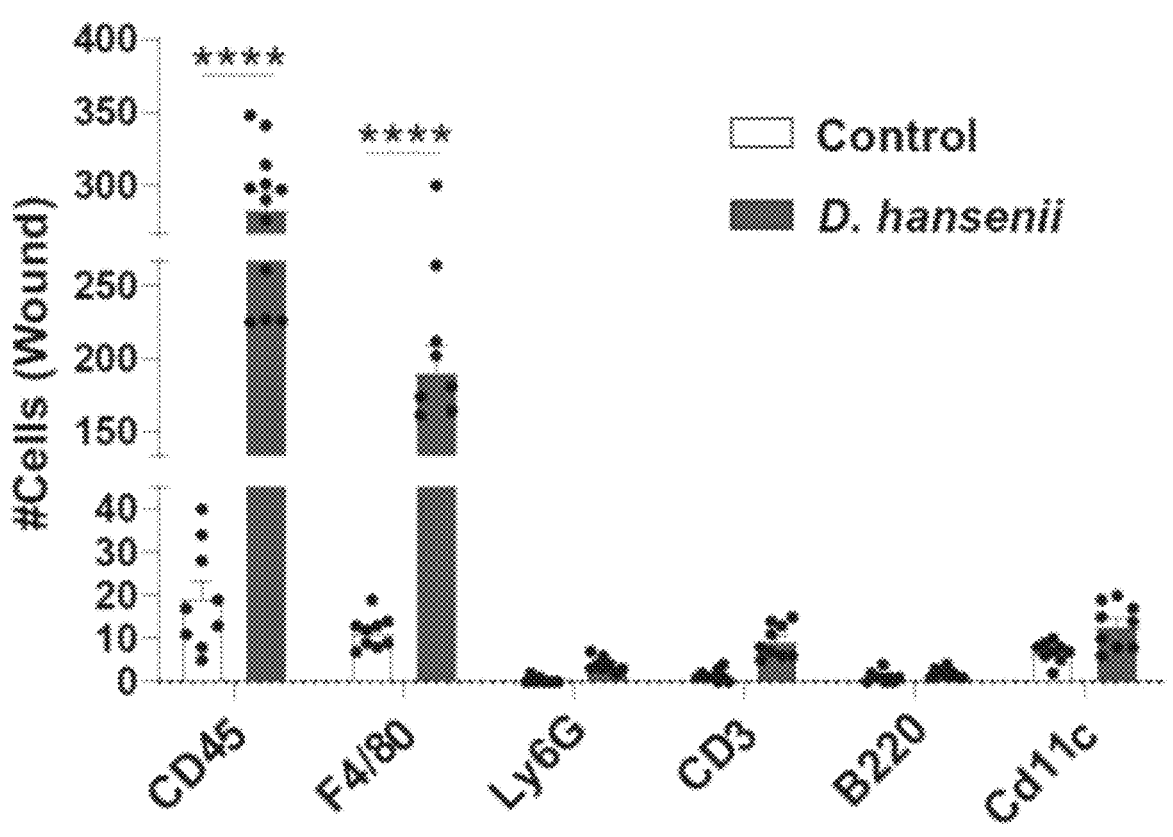
Figure 20A:
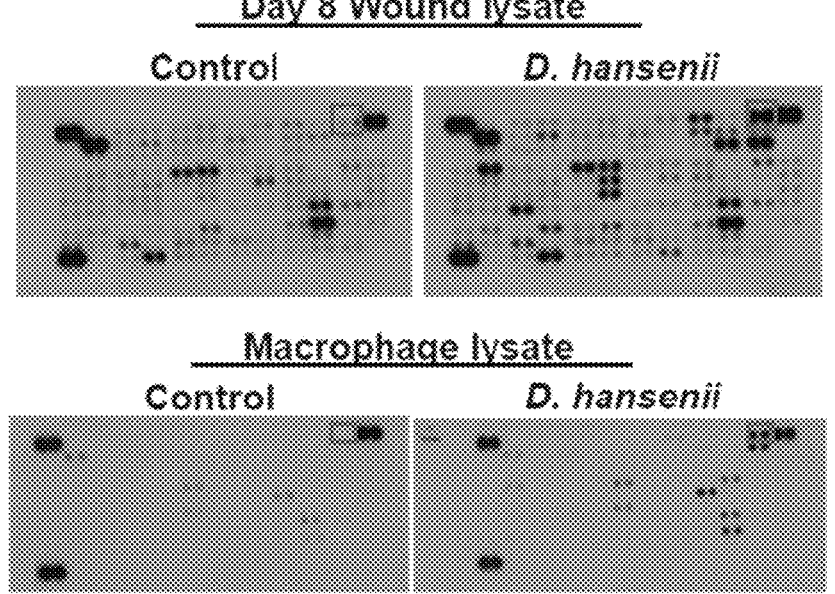
FIG. 20: *D. hansenii* induces CCL5 production. (A) Cytokine/chemokine profile changes in *D. hansenii* infected wounds (n=11 wounds from 5 mice/group from 2 experiments) or macrophages versus uninfected controls (n=3 experiments). Red boxes indicate CCL5 on the membrane. (B) Wound CCL5 levels at day 8 post-injury from uninfected (control) or *D. hansenii*-infected mice evaluated by ELISA (n=15-27 wounds/group from 5-8 mice/group). Significance was determined by unpaired Student's t-test: **p<0.01. (C) Bone marrow-derived macrophages were cultured in the presence or absence of live *D. hansenii* or *S. cerevisiae* (MOI 1:10) for 24 hours followed by quantification of CCL5 in the supernatant by ELISA (n=3 independent experiments). Significance was determined by one-way ANOVA and TUKEY's post-hoc test: ****p<0.0001 (D) Bone marrow-derived macrophages were cultured and stimulated with *D. hansenii* or vehicle (control) and CCL5 was measured in the 24-hour culture supernatants (n=4 independent experiments). MOI=Multiplicity of infection. (E) In situ hybridization for detecting Ccl5 in the ulcers of DSS fed germ-free mice pre colonized with ASF in the presence or absence of *D. hansenii* (Bars=50 μm). All values in B, C, and D are displayed as mean±SEM.
Figure 20B:
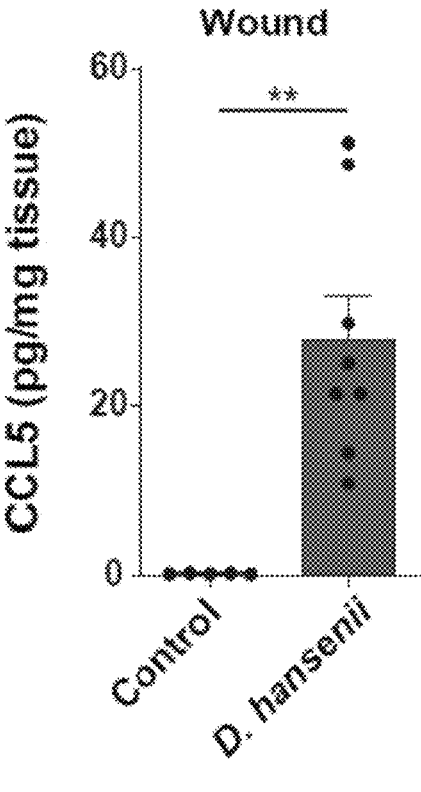
Figure 20C:
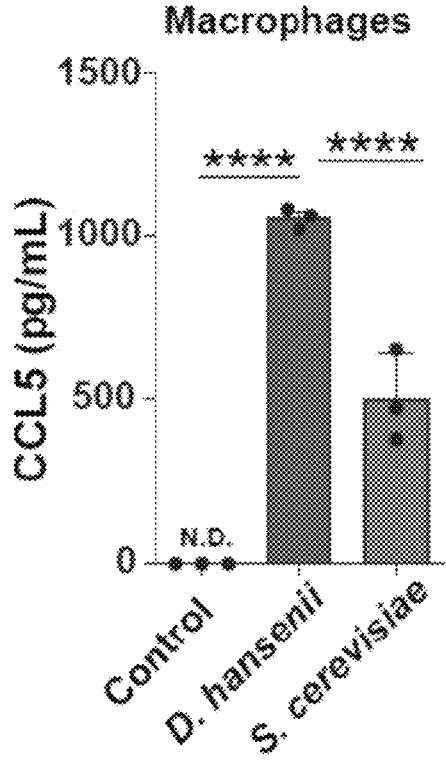
Figure 20D:
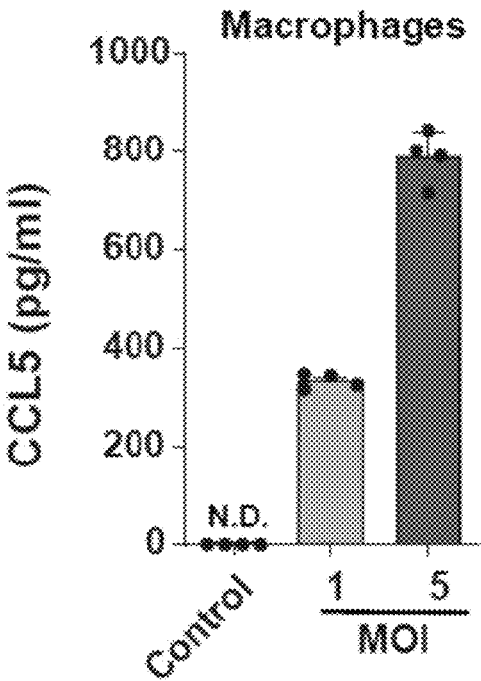
Figure 20E:
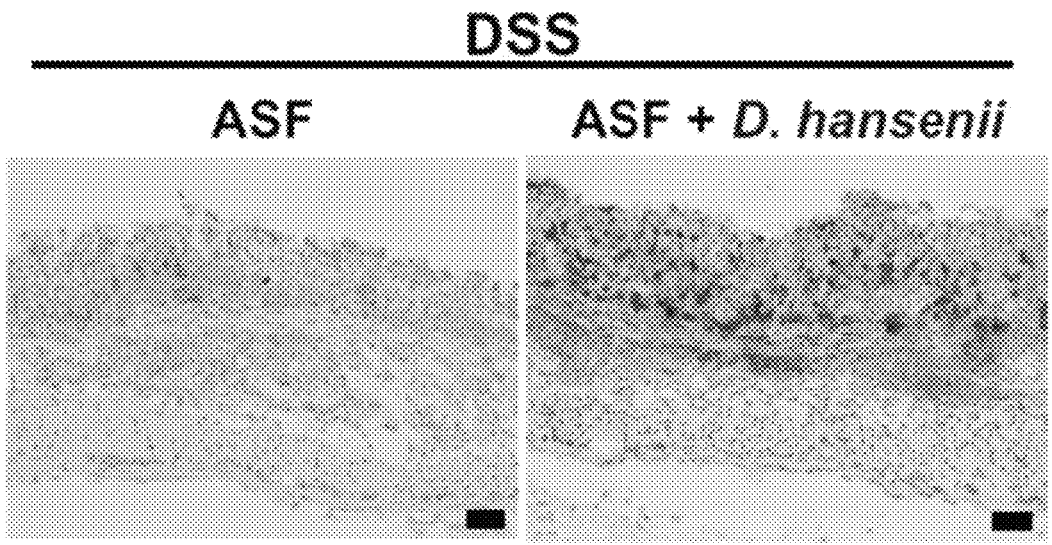

Analysis of sorted wound bed cells of *D. hansenii* infected WT mice showed that F4/80+ macrophages predominantly contained *D. hansenii* as shown by sequencing and culture of the intracellular contents of these cells (FIG. 3A, B and FIG. 19C). These findings were consistent with a preferential infiltration of macrophages within wounds colonized by *D. hansenii* (FIG. 19D, E).

For protein measurements by ELISA and cytokine/chemokine array, wounds were collected in PBS and homogenized in RIPA buffer containing protease and phosphatase inhibitors (Thermo Fisher Scientific) using Lysing Matric D tubes (MP Biomedicals) and an automated bead beater (FastPrep-24 5G; MP Biomedicals). The supernatant was centrifuged at 10,000 g for 15 mins and the resulting supernatants were collected and stored at −80° C. until further analysis. The array coordinates are listed in FIG. 15.

Figure 32B:
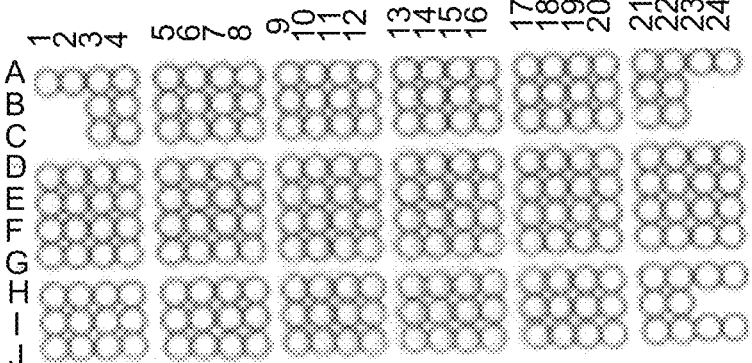
FIG. 32: (A) Cytokine coordinates and the (B) cytokine array membrane.

To identify the most prominent immune responses induced by *D. hansenii*, we compared the expression of 111 different cytokines in parallel from wound tissue lysates from PBS and *D. hansenii* gavaged mice, as well as lysates from cultured macrophages stimulated with or without *D. hansenii* in vitro. The R&D Proteome Profiler Mouse XL Cytokine Array (FIGS. 32A and 32B) was used for quantification of 111 different chemokines and/or cytokines in the lysates of wounds or macrophages according to the protocol recommended by the manufacturer. Image J was used for quantification.

Figure 10A:
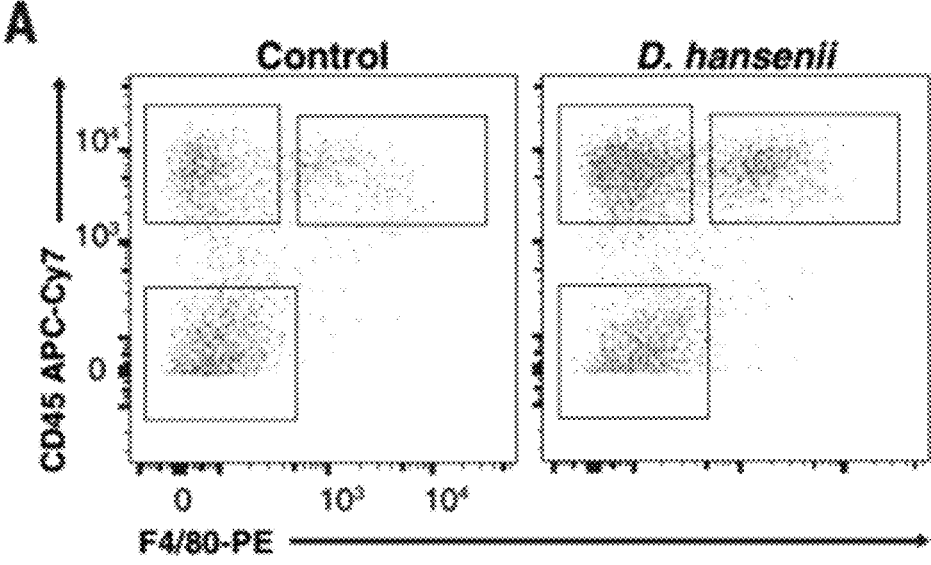
FIG. 10: *D. hansenii* impaired crypt regeneration via type 1 IFN and CCL5. (A) Representative plots ex vivo sorting of live cell populations from the colons of mice 5 days post DSS withdrawal colonized with or without *D. hansenii*. (B) Cells sorted in (A) were lysed and plated on SDA plates for fungal culture (n=4-6 mice per group). Significance was determined by two-way ANOVA with Tukey's post hoc test: ***p<0.001. (C) Scatter plot showing the fold change in *D. hansenii*-infected wounds (black circles) or macrophages (gray circles) compared to their respective PBS treated controls. (D-E) Ccl5−/− and WT littermate controls were gavaged with *D. hansenii* and subsequently biopsy injured using the same protocol depicted in FIG. 9F. (D) Representative H&E stained sections from the infected WT and Ccl5−/− mice and (E) wound bed length at day 12 post-injury (n=12-17 wounds/group from 5-7 mice/group). Significance was determined by unpaired Student's t-test: ****p<0.0001. (F) Percent crypt loss in the distal colon of Ccl5−/− and WT littermate controls subjected to the DSS treatment and recovery model in the absence or presence of *D. hansenii* (n=6 mice/group from 2 experiments). Significance was determined by two-way ANOVA and Tukey's post hoc test: **p<0.01. (G) Bone marrow-derived macrophages from indicated genotypes were cultured in the presence of live *D. hansenii* (MOI 1:10) for 24 hours followed by quantification of CCL5 in the supernatant by ELISA (n=4 independent experiments). All values for the Ifnar−/− group were below detection limit, referred to as N.D. (not detected). (H-I) Ifnar−/− and WT littermate controls were gavaged with *D. hansenii* and subsequently biopsy injured using the protocol depicted in FIG. 9F. (H) Representative H&E stained sections from the WT and Ifnar−/− mice and (I) wound bed length at day 12 post-injury (n=16 wounds from 6-7 mice/group). Significance was determined by unpaired Student's t-test: ****p<0.0001. (J) CCL5 measured in the supernatants of WT and Stat1−/− macrophages post *D. hansenii* stimulation as in (G) (n=4 independent experiments). Significance was determined by unpaired Student's t-test: ****p<0.0001. (K) Representative H&E stained sections and (L) percent crypt loss in the distal colons of littermate LysMCre Stat1 fl/fl and Stat1fl/fl mice subjected to DSS treatment and repair in the presence of *D. hansenii* (n=6-10 mice/group). Significance was determined by unpaired Student's t-test: ****p<0.0001. All values in B, E, F, G, I, J, and L are displayed as mean±SEM. The dashed black line in D and H at the center of the wound represents wound bed length (largest distance between the crypts). Bars=100 μm.
Figure 10B:
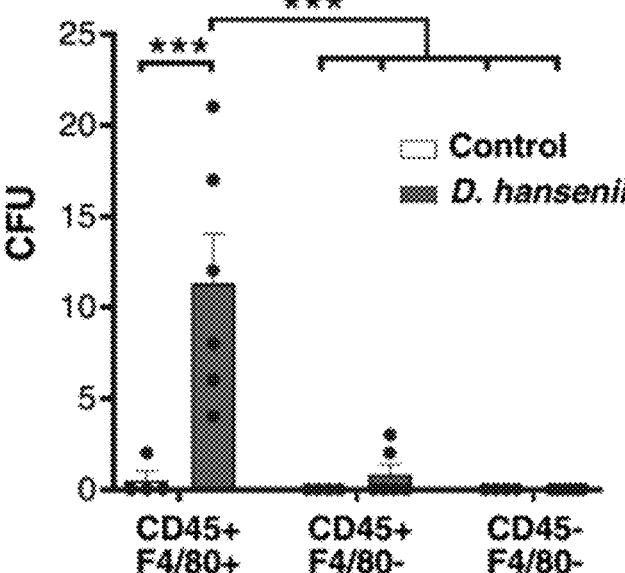
Figure 10C:
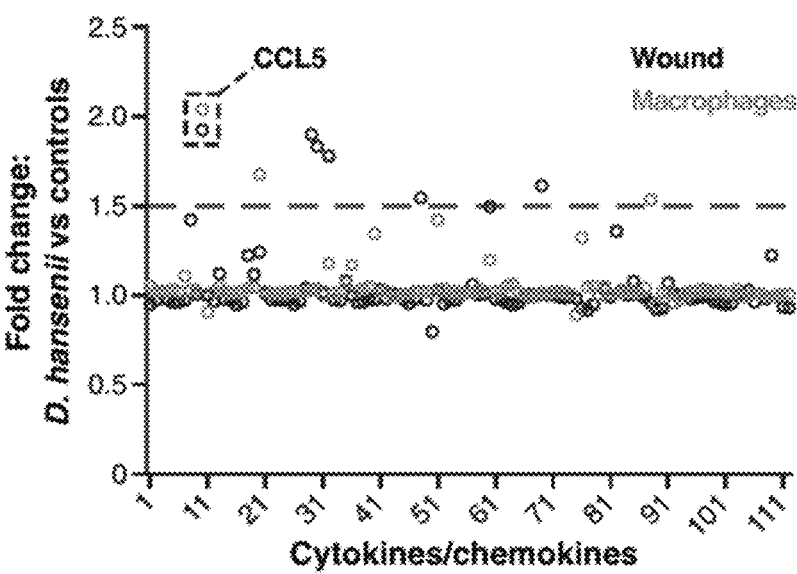
Figure 10D:
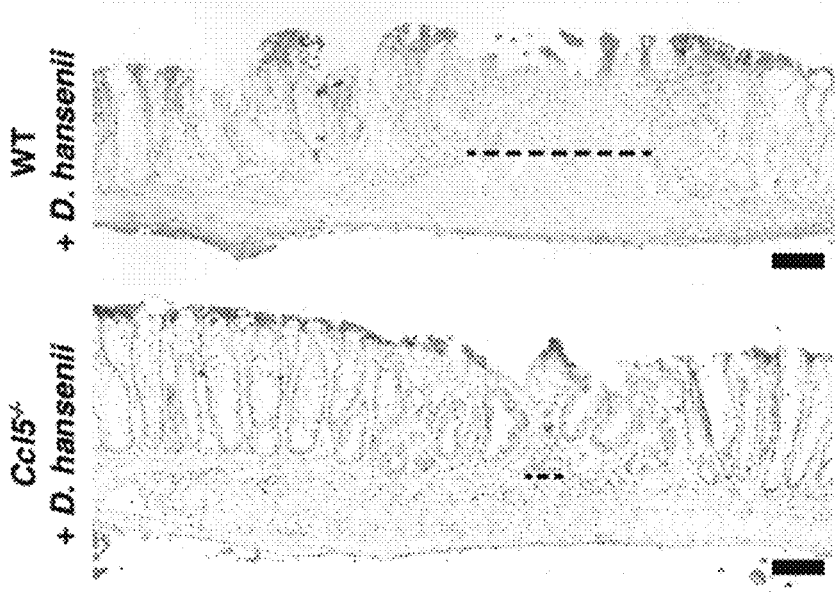
Figure 10E:
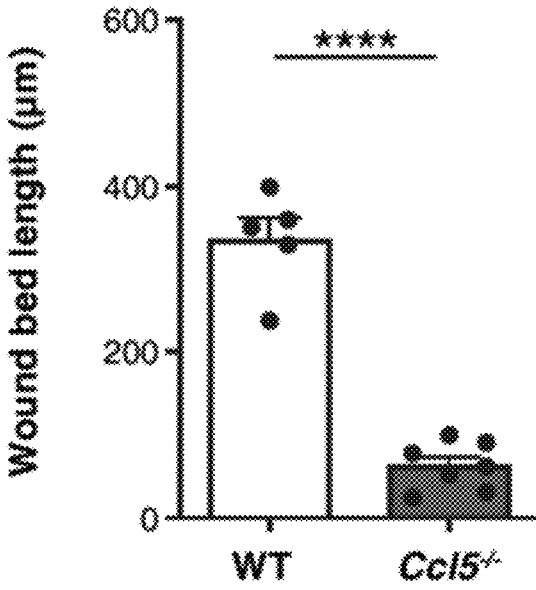
Figure 10F:
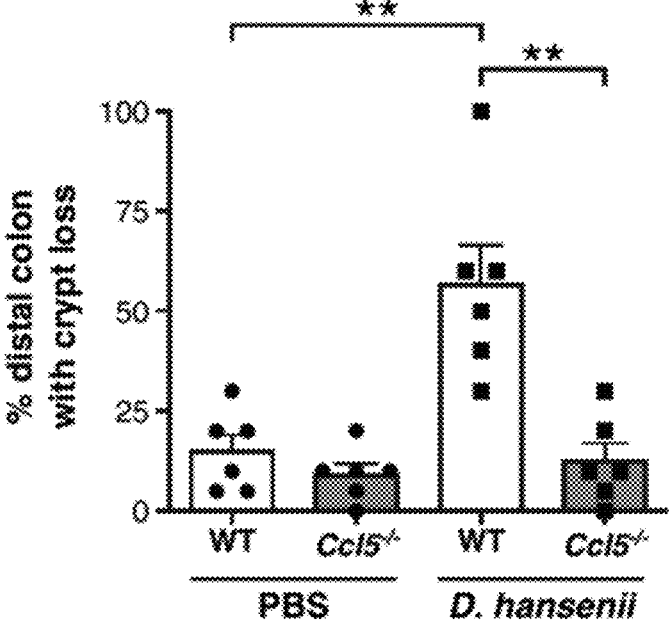
Figure 21:
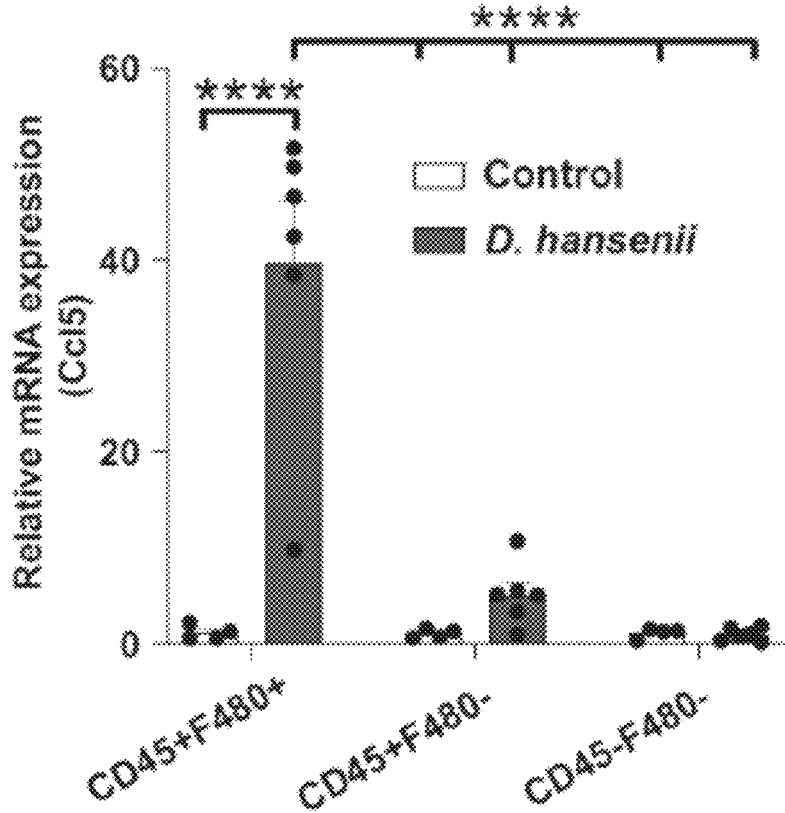
FIG. 21: CD45+F480+ cells are a major source of Ccl5 in the colonic wounds of *D. hansenii* infected mice. WT mice were administered PBS (controls) or *D. hansenii*, exposed to DSS for 7 days followed by 5 days of regular drinking water. Relative expression of Ccl5 in the indicated cell fractions isolated from the colons of mice 5 days post-DSS cessation, in the presence or absence of *D. hansenii* (n=4-6 mice/group from 2 separate experiments). Significance was determined by two-way ANOVA and TUKEY's post-hoc test: ****p<0.0001. All values are displayed as mean±SEM.
Figure 22A:
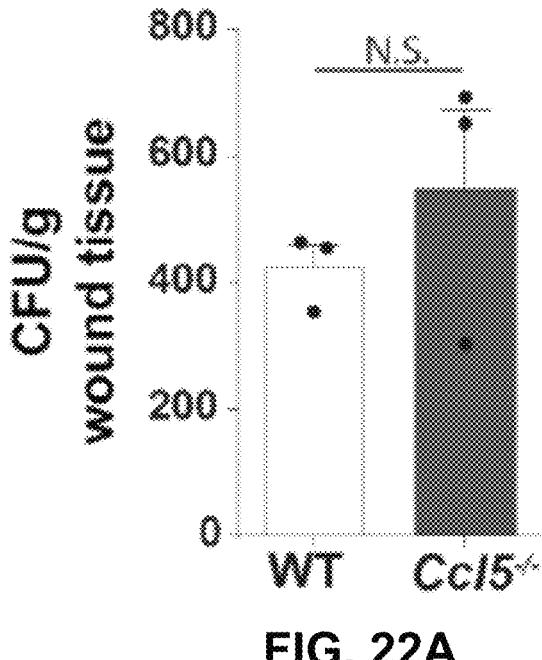
FIG. 22: Debaryomyces colonization was similar between WT and Ccl5–/– mice. Wounds at day 8 post-injury from *D. hansenii* colonized littermate WT and Ccl5–/– mice were homogenized and plated on SDA pates. (A) Colony counts and (B) relative abundance of genera of all viable colonies in the indicated groups of mice identified by ITS sequencing (n=13 wounds from 3 mice/group) (note all six bars show only *D. hansenii*). Data for relative abundance is broken down by individual mice on the x-axis. Significance was determined by unpaired Student's t-test. N.S.=not significant. Data are displayed as mean±SEM.
Figure 22B:
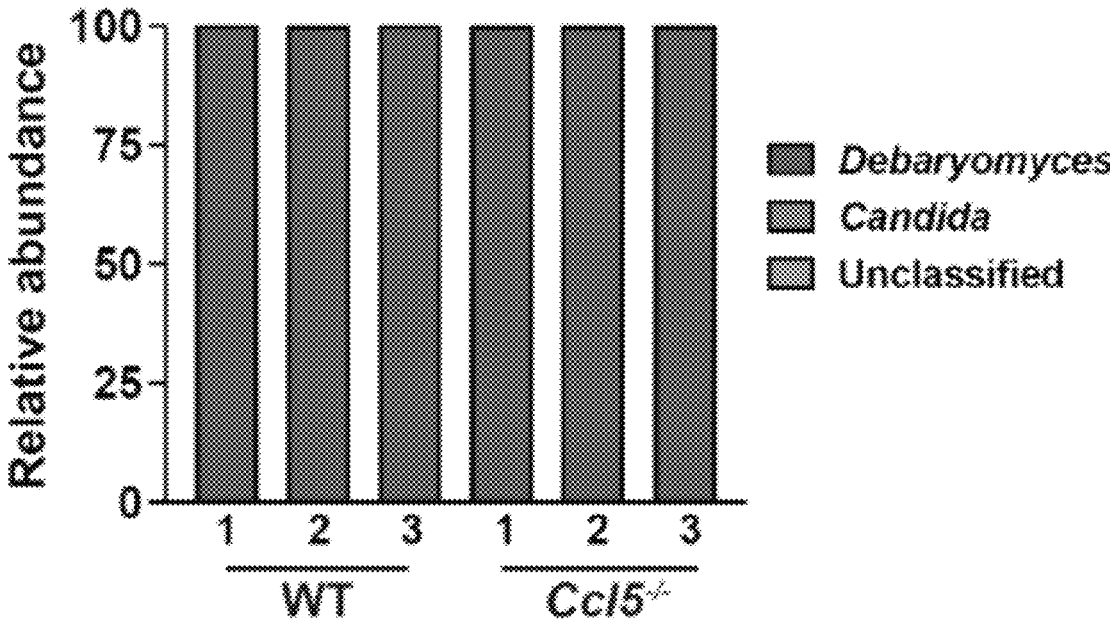

Analysis of cytokine arrays showed that *D. hansenii* was not broadly pro-inflammatory and instead induced a robust production of CCL5 both in vitro and in vivo which we further validated by ELISA and in situ hybridization in multiple models (FIG. 10C, FIGS. 20 and 32). In situ hybridization for CCL5 was performed on 5 μm sections using manual RNAscope assay according to the manufacturer's instructions (Advanced Cell Diagnostics). RNAscope probe was used for CCL5: (NM_013653.3, region 4-597). The expression of CCL5 was preferentially induced in F480+ macrophages in the wound bed in vivo (FIG. 21).

Example 9: Ccl5 Modulation by *Debaryomyces hansenii*

To characterize whether *D. hansenii* colonization impairs wound healing through upregulation of CCL5, the following experiments were conducted.

Knockout mice, all on C57BL6 genetic background, were used along with WT controls were used in these experiments. The knockout mice included strains Ccr5–/– (JAX stock #005427), Ccl5–/– (JAX stock #005090), Tlr3–/– ((JAX stock #009675), Stat1–/–, Ifnar1–/–(48), LySMCre and Stat1fl/fl. All mouse colonies were maintained as heterozygous crosses to obtain littermate controls. Germ-free mice were bred and maintained in isolators of a germ-free facility. 5-10-week-old male mice were used for all the experiments.

In contrast to WT littermate controls, *D. hansenii* gavage did not impede mucosal healing in Ccl5–/– mice despite similar colonization within wounds as WT mice (FIG. 10D-F, and FIG. 22).

Figure 23A:
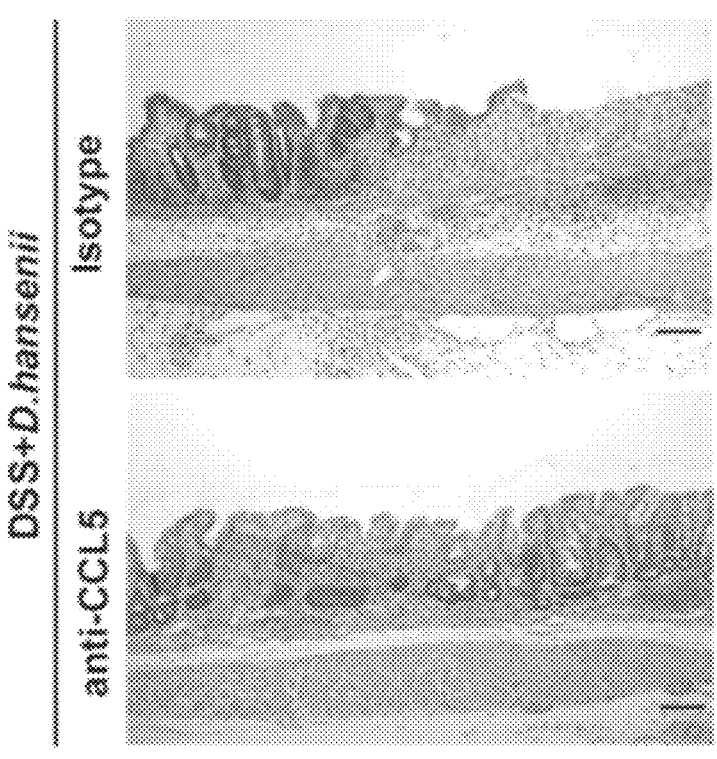
FIG. 23: CCL5 neutralization rescues healing defect associated with colonization by *D. hansenii*. WT SPF mice gavaged with *D. hansenii* were treated with anti-CCL5 antibody or isotype control and exposed to DSS followed by two weeks of recovery. (A) Representative H&E stained images and (B) percent crypt loss from the distal colon in the indicated groups of mice (n=6-7 mice per group from 3 experiments). Significance was determined by unpaired Student's t-test: ****p<0.0001.
Figure 23B:
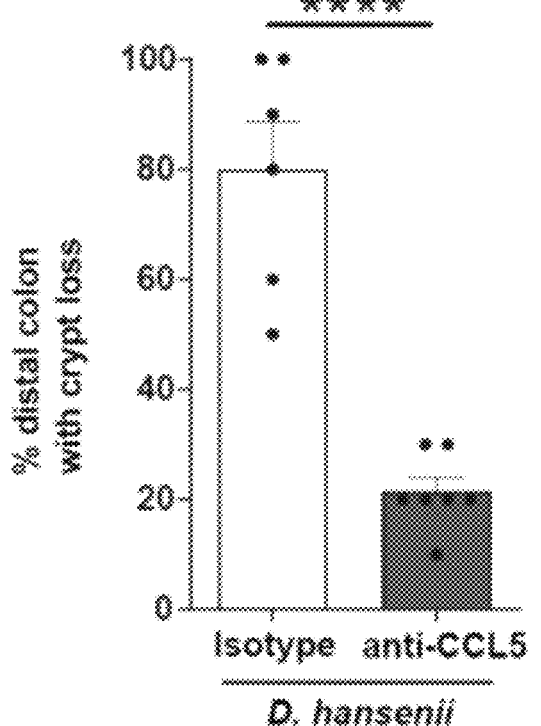
Figure 24:
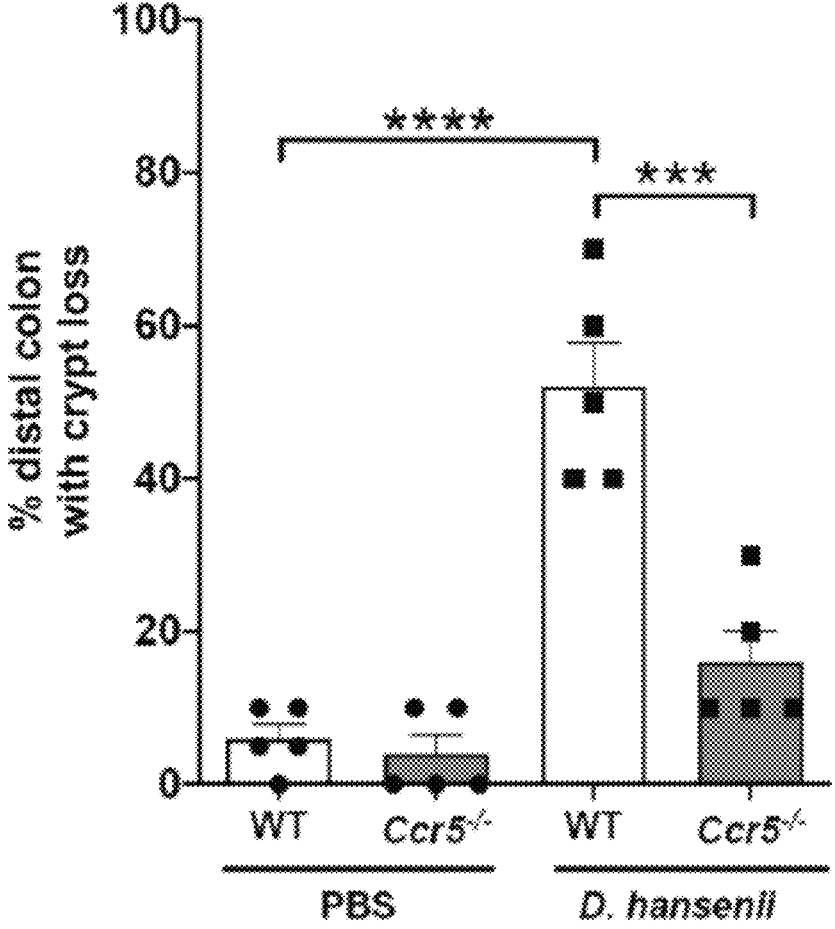
FIG. 24: Pathogenic effects of *D. hansenii* were diminished in mice lacking the CCL5 receptor encoded by Ccr5. Ccr5–/– and WT littermate controls were gavaged with *D. hansenii* or PBS (controls) and exposed to DSS followed by two weeks recovery. (A) Percent of crypt loss in the distal colon (n=5 mice/group from 2 experiments). Significance was determined by two-way ANOVA with Tukey's post hoc test: *p<0.001, **p<0.0001. Data are displayed as mean±SEM.

To test if this phenotype in Ccl5–/– mice was potentially due to developmental defects, the following experiment was conducted. In the DSS recovery model, WT mice were infected with *D. hansenii* with either a CCL5 neutralizing antibody or an isotype control. WT mice were treated with anti-CCL5 antibody (R&D; MAB478) or isotype controls three times a week (intraperitoneally, 50 µg/injection) until the end of the experiment. CCL5 inhibition rescued the wound repair defect (FIG. 23). Because CCL5 interacts with CCR5 to induce pathology in the context of fungal infections, Ccr5–/– mice were similarly tested and found to be resistant to the detrimental effects of *D. hansenii* (FIG. 24). Given that CCL5 is known to be elevated in Crohn's disease (CD), targeting CCL5 has the potential to be an effective therapeutic approach to improving mucosal healing in this disease.

To determine how *D. hansenii* induces CCL5, an RNA-seq analysis of bone marrow-derived macrophages (BMDMs) in the presence or absence of *D. hansenii* was performed.

Bone marrow cells from femurs and tibia of mice were isolated and plated in dishes (not treated for tissue culture) containing high glucose DMEM (Life Technologies) with 5% horse serum (Sigma), 10% fetal bovine serum (Sigma), Penicillin-Streptomycin (Sigma), 10 mM HEPES (Corning), 1% L-glutamine, 1% sodium pyruvate and Macrophage Colony-Stimulating Factor (Biolegend) at 10 ng/ml for 7 days prior to the experimental procedure.

For stimulation experiments, macrophages were collected in DMEM by cell scraper and reseeded in 6- or 12-well plates in DMEM containing 10% Fetal bovine serum, Penicillin-Streptomycin (Sigma), 10 mM HEPES (Corning) and allowed to adhere. After 24 hours, cells were washed with sterile PBS and resuspended in fresh media and stimulated with live *D. hansenii* or *Saccharomyces cerevisiae* (MOI—1:5 or 1:10) or vehicle (PBS). 24 hours post-stimulation, supernatants were collected and assayed for CCL5 by ELISA. CCL5 was quantified by ELISA (BD Biosciences) according to the manufacturer's instructions. In some experiments 24 hours post-stimulation, cells were washed with PBS and lysed in RIPA (Sigma) containing protease and phosphatase inhibitors (Thermo Fisher Scientific). These lysates were used for quantification of cytokines/chemokines as described above. In some experiments, RNA was isolated from total cell lysates with Trizol Reagent via NucleoSpin RNA Isolation Kits.

RNA library preparations and sequencing reactions were conducted at GENEWIZ, LLC. (South Plainfield, NJ, USA). RNA samples were quantified using Qubit 2.0 Fluorometer (Life Technologies, Carlsbad, CA, USA) and RNA integrity was checked using Agilent TapeStation 4200 (Agilent Technologies, Palo Alto, CA, USA). RNA sequencing libraries were prepared using the NEBNext Ultra RNA Library Prep Kit using the manufacturer's instructions (NEB, Ipswich, MA, USA). Briefly, mRNAs were initially enriched with Oligo d(T) beads. Enriched mRNAs were fragmented for 15 minutes at 94° C. First-strand and second-strand cDNA were subsequently synthesized. cDNA fragments were end-repaired and adenylated at 3'-ends, and universal adapters were ligated to cDNA fragments, followed by index addition and library enrichment by PCR with limited cycles. The sequencing library was validated on the Agilent TapeStation (Agilent Technologies, Palo Alto, CA, USA), and quantified by Qubit 2.0 Fluorometer (Invitrogen, Carlsbad, CA) as well as by quantitative PCR (KAPA Biosystems, Wilmington, MA, USA). The sequencing libraries were clustered on a single lane of a flowcell. After clustering, the flowcell was loaded on the Illumina HiSeq instrument (4000 or equivalent) according to the manufacturer's instructions. The samples were sequenced using a 2×150 bp Paired-End (PE) configuration. Image analysis and base calling were conducted by the HiSeq Control Software (HCS). Raw sequence data generated from Illumina HiSeq was converted into fastq files and de-multiplexed using Illumina's bcl2fastq 2.17 software. One mismatch was allowed for index sequence identification. Sequence reads were trimmed to remove possible adapter sequences and nucleotides with poor quality using Trimmomatic v.0.36. The trimmed reads were mapped to the *Mus musculus* GRCm38 reference genome available on ENSEMBL using the STAR aligner v.2.5.2b. Unique gene hit counts were calculated by using feature counts from the Subread package v.1.5.2. The hit counts were summarized and reported using the gene_id feature in the annotation file. Only unique reads that fell within exon regions were counted. Since a strand-specific library preparation was performed, the reads were strand-specifically counted.

After extraction of gene hit counts, differential expression analysis was conducted in R (version 4,0). Counts were normalized using the EdgeR package (version 3.30), and only genes with at least 1 count per million reads in at least 3 samples were retained for downstream analysis (n=12, 693). The Limma package was used for differential expression testing using the voom method with empirical Bayes moderation (version 3.44.1). Functional enrichment analysis was performed using the Fast Gene Set Enrichment Analysis package compared to GO Biological Process pathways (FGSEA package version 1.14).

Figure 25A:
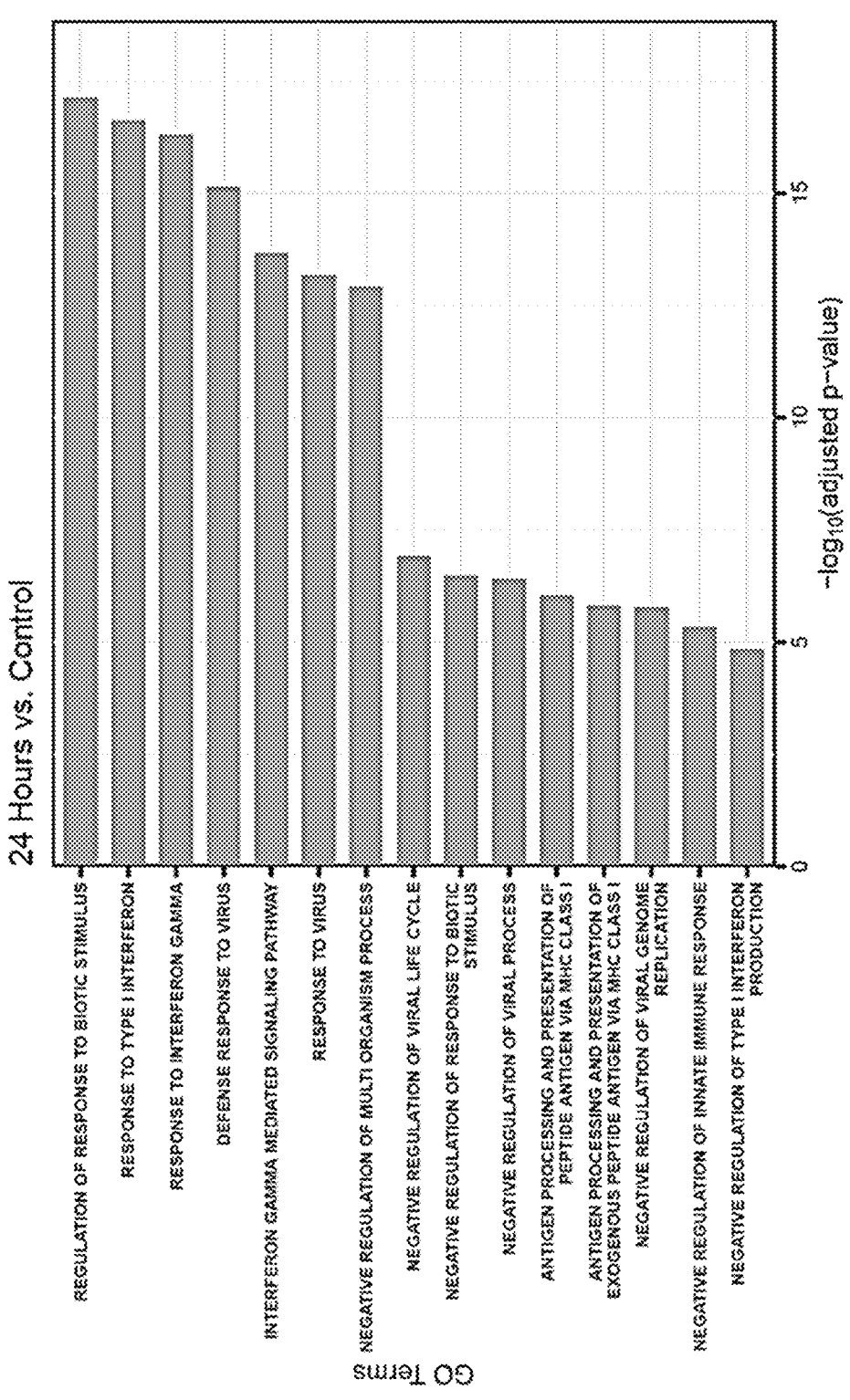
FIG. 25: *D. hansenii* induces type 1 IFN signature in macrophages. (A) Bone marrow-derived macrophages were cultured with or without *D. hansenii* and RNA was extracted for RNA seq analysis at 24 hours post-stimulation (n=3 replicates per group). The 15 GO categories with the largest Normalized Enrichment Score are plotted. (B) Bone marrow-derived macrophages were cultured in the presence or absence of live *D. hansenii* (MOI 1:10) for 8 hours and relative mRNA expression of IFN-β was analyzed by qPCR (n=3 independent experiments). Significance was determined by unpaired Student's t-test: *p<0.05.
Figure 25B:
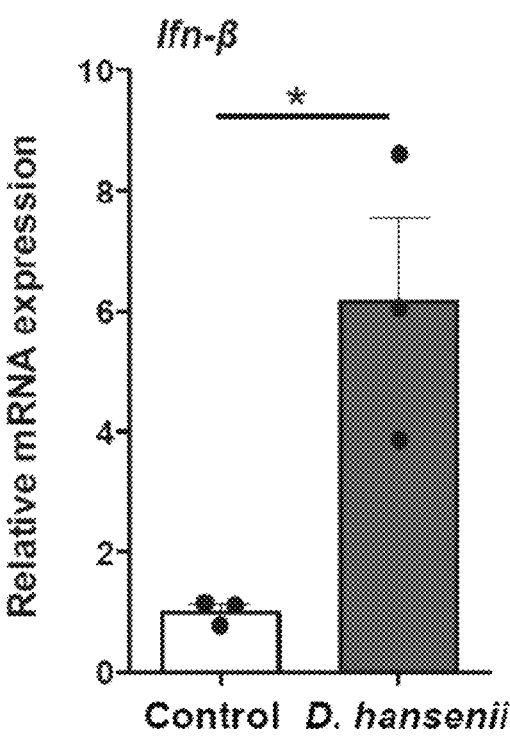

Significant increases in genes associated with the type 1 interferon (IFN) pathway were associated with *D. hansenii* or *Saccharomyces cerevisiae* stimulation (FIG. 25).

To validate RNA-seq findings in vivo, we quantified the expression of type I IFN pathway genes, including Irf7, Isg15, and Mx2. For RNA quantification, cDNA was synthesized using iScript cDNA Synthesis Kit (BioRad) and qPCR was performed SYBRGreen Master Mix (Roche) with the following conditions: 50° C. for 2 minutes, then 95° C. for 10 minutes followed by 40 cycles of 95° C. for 15 seconds and 60° C. for 1 minute. The following primers were used as described previously (34, 53-55)—Mx2: forward (5'-GAGGCTCTTCAGAATGAGCAAA-3', SEQ ID NO:11), reverse (5'-CTCTGCGGTCAGTCTCTCT-3', SEQ ID NO:12), Irf7: forward (5'-CTGGAGC-CATGGGTATGCA-3', SEQ ID NO:13), reverse (5'-AAGCACAAGCCGAGACTGCT-3', SEQ ID NO:14), Isg15 forward (5'-AAGCTCAGCCAGAACTGGTCT-3', SEQ ID NO:15), reverse (5'-ATGGCCTGGGACCTAAAGGTGAA-3', SEQ ID NO:16), mouse Gapdh: forward (5'-AGGTCGGTGTGAACGGAT-TTG-3', SEQ ID NO:17), reverse (5'-TGTAGAC- CATGTAGTTGAGGTCA-3', SEQ ID NO:18), human Gapdh: forward (5'-GACCTGCCGTCTAGAAAAACC-3', SEQ ID NO:19), reverse (5'-GCTGTAGCCAAAT-TCGTTGTC-3', SEQ ID NO:20), Ifn-β: forward (5'-CTG-GAGCAGCTGAATGGAAAG-3', SEQ ID NO:21), reverse (5'-CTTCTCCGTCATCTCCATAGGG-3', SEQ ID NO:22) and Ccl5: forward (5'-TGCCCACGTCAAGGAGTATTTC-3', SEQ ID NO:23), reverse (5'-AACC-CACTTCTTCTCTGGGTTG-3', SEQ ID NO:24).

Figure 26:
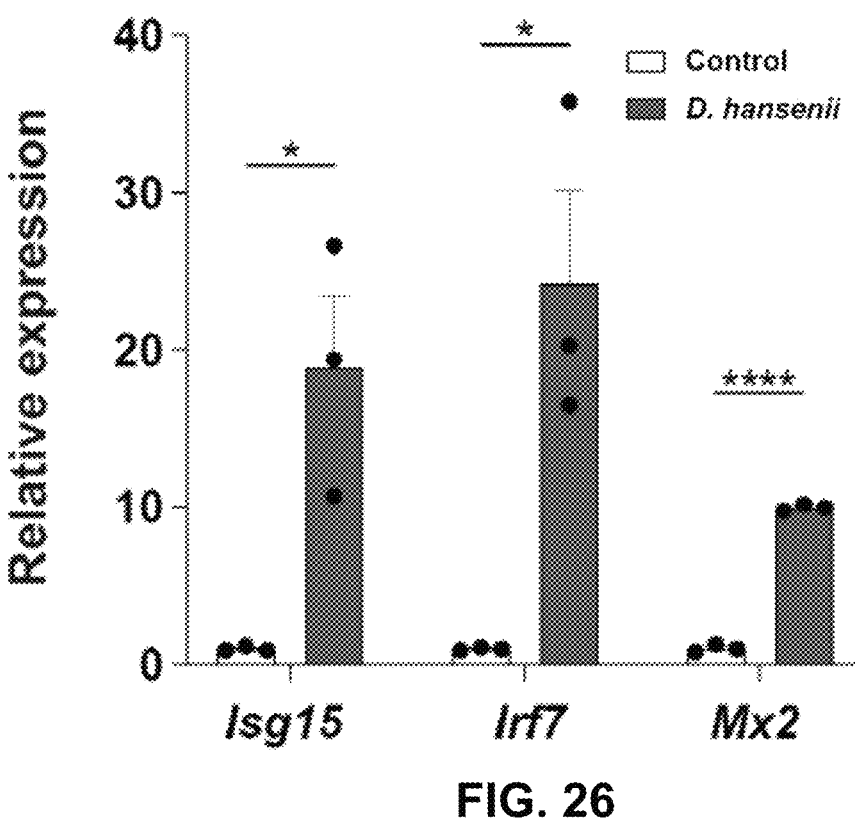
FIG. 26: *D. hansenii* induces type 1 IFN signature in vivo. Relative mRNA expression of the indicated transcripts from day 8 wounds of biopsy injured mice gavaged with *D. hansenii* or PBS (control) (n=9 wounds from 3 mice/group). Significance was determined by unpaired Student's t-test: *p<0.05, ****p<0.0001.

The expression of type I IFN pathway genes Irf7, Isg15, and Mx2 were significantly elevated in the wounds of *D. hansenii* colonized mice as compared to controls (FIG. 26). Furthermore, in concordance with CCL5 expression data, IFN-β mRNA was also preferentially induced in the wound bed F480+ macrophages in vivo (FIG. 27).

Figure 10G:
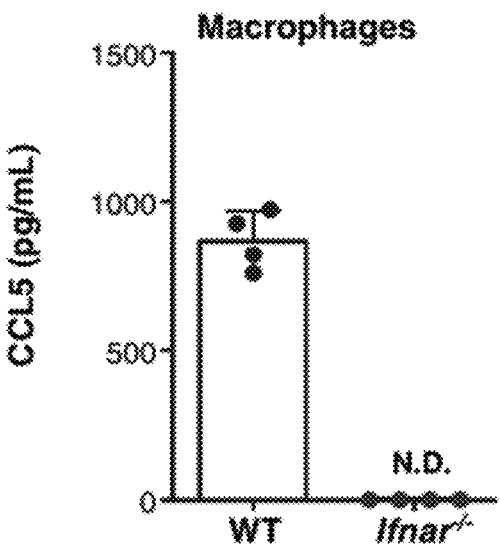
Figure 10H:
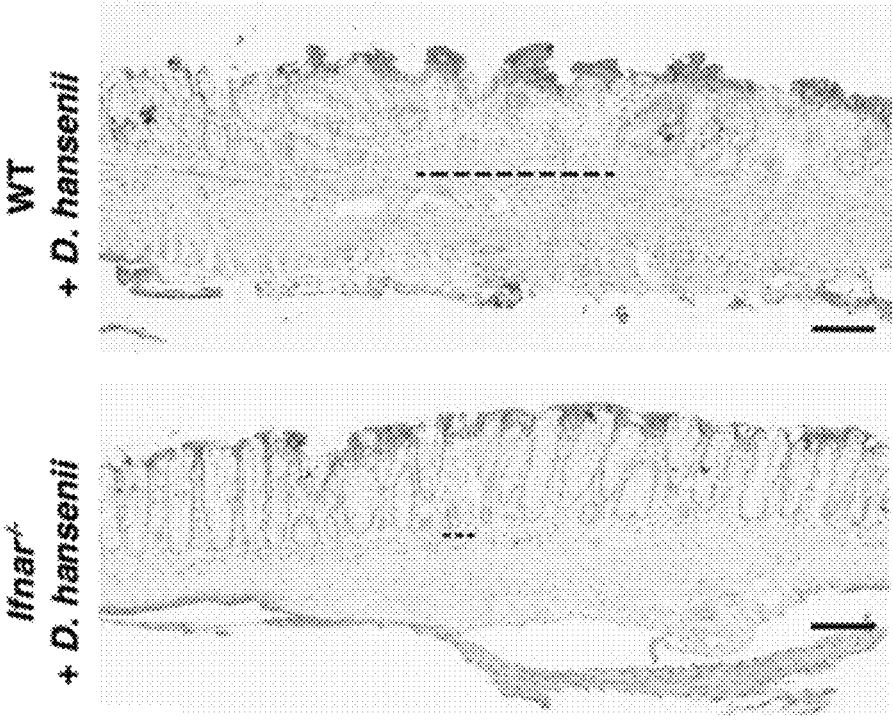
Figure 10I:
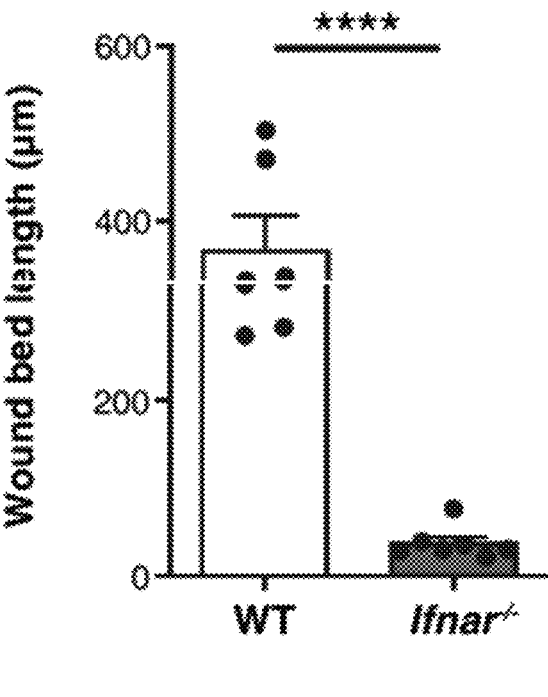
Figure 10J:
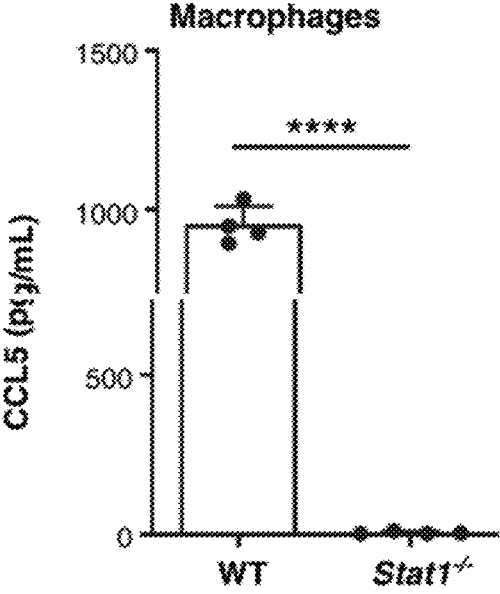
Figure 10K:
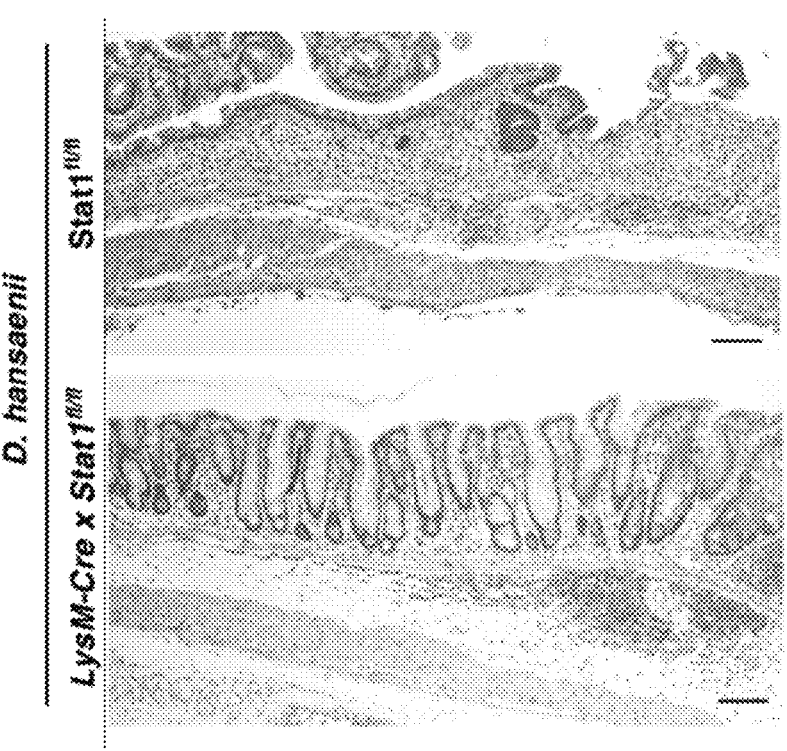
Figure 10L:
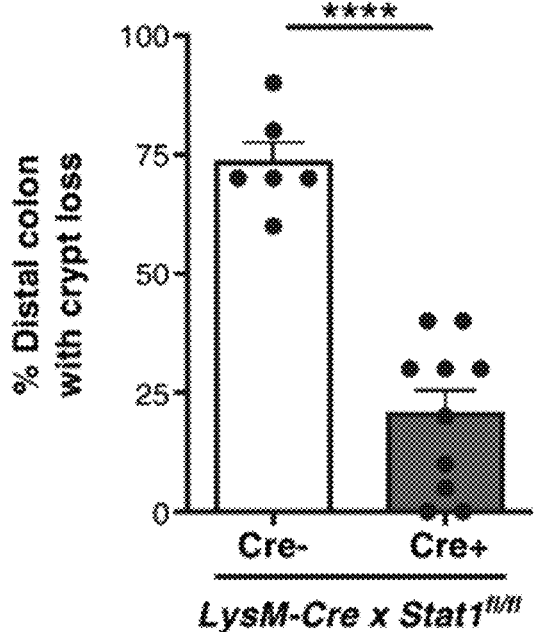

To determine if type 1 IFN activity was required for the increase in CCL5 production in the presence of *D. hansenii*, macrophages from WT mice and mice lacking the type 1 IFN receptor (IFNAR) were stimulated with *D. hansenii* and CCL5 was measured in the supernatants as described above. Strikingly, the absence of Ifnar completely abolished the production of CCL5 in response to *D. hansenii*, suggesting type 1 IFN activity is upstream of CCL5 induction (FIG. 10G). The pathogenic effects of *D. hansenii* were abolished in mice lacking Ifnar (FIG. 10H, I). Stat1, a key transcription factor downstream of IFNAR), was also required for *D. hansenii* induced CCL5 production. Mice lacking Stat1 in myeloid cells were protected from *D. hansenii* induced healing defects compared to littermate controls (FIG. 10J-L). Candidate pathways upstream of CCL5 were also tested. The effects of *D. hansenii* were Dectin-1 independent but partially dependent on TLR3 (FIG. 28). Collectively, these findings suggested that *D. hansenii* requires type 1 IFN and CCL5 in myeloid cells to impair mucosal healing post-injury.

Example 10: *Debaryomyces hansenii* in Crohn's (Cd) Patients

Crohn's disease is characterized by impaired mucosal healing and is closely associated with fungal dysbiosis, To test the hypothesis that *Debaryomyces* is present in the tissues obtained from individuals with CD, the following experiments were conducted.

The human subjects used in the experiments described below included healthy controls and various cohorts of patients with Crohn's disease (CD). Demographic information on the CD subjects included in these experiments is summarized in Table 2 below. All human samples were assigned an anonymized identification number with no relation to patient identity. For the samples collected prospectively (surgical and colonoscopy cohort, Table 2), an intestinal biopsy was obtained from patients with Crohn's disease who were undergoing colonoscopy for routine care from areas of active inflammation based on symptoms and/or imaging and from healthy controls (Sex: 4 males and 6 females; Age (Mean±SD): 57±6) undergoing colon cancer screening. Control patients were free of major cardiovascular disease, diabetes, malignancy, active infection, or gastrointestinal disease. For the surgical cohort, ileal specimens were collected from patients with Crohn's disease undergoing resection. All specimens were received fresh, within 20 minutes of resection. A pathologist opened the specimen and collected 1 cm×1 cm each of non-inflamed and inflamed tissue as determined by gross inspection. Collected specimens were put in fresh phosphate-buffered saline and sampled for DNA extraction or streaking on Sabouraud dextrose agar (SDA) as described below.

For retrospective analysis (Biobank samples), samples were acquired from three independent cohorts (Ileum1, Ileum 2, and Colon; Table 1; matched inflamed and uninflamed).

TABLE 2

| Demographic data for CD subjects included in the analyses. | | | | | |
|---|---|---|---|---|---|
| | Surgical Cohort (N = 6) | Colonos-copy Cohort (N = 7) | Biobank Colon (N = 8) | Biobank Ileum 1 (N = 7) | Biobank Ileum 2 (N = 10) |
| Age (median years, IQR) | 34 (12) | 49 (18) | 29 (17) | 35 (7) | 39 (12) |
| Female (n, %) | 2 (33) | 4 (57) | 4 (50) | 6 (86) | 6 (60) |
| Family History (n, %) | 0 (0) | 1 (14) | 2 (25) | 6 (86) | 4 (40) |
| Race (n, %) | | | | | |
| American Indian or Alaska Native | 0 (0) | 0 (0) | 0 (0) | 0 (0) | 0 (0) |
| Asian | 0 (0) | 0 (0) | 0 (0) | 0 (0) | 0 (0) |
| Black | 1 (17) | 0 (0) | 0 (0) | 0 (0) | 0 (0) |
| Native Hawaiian or Other Pacific Islander | 0 (0) | 0 (0) | 0 (0) | 0 (0) | 0 (0) |
| White | 5 (83) | 7 (100) | 8 (100) | 7 (100) | 10 (100) |
| Hispanic or Latino | 0 (0) | 0 (0) | 0 (0) | 0 (0) | 0 (0) |
| Current smoker (n, %) | 2 (33) | 0 (0) | 2 (25) | 1 (14) | 1 (10) |
| Disease duration (median years, IQR) | 13 (4) | 26 (19) | 9 (6) | 18 (15) | 15 (17) |
| Disease location (n, %) | | | | | |
| Ileal (L1) | 2 (33) | 2 (29) | 1 (13) | 2 (29) | 4 (40) |
| Colonic (L2) | 0 (0) | 0 (0) | 0 (0) | 0 (0) | 0 (0) |
| Ileocolonic (L3) | 4 (67) | 5 (71) | 7 (88) | 5 (71) | 6 (60) |
| Upper gut (L4) | 0 (0) | 3 (43) | 1 (13) | 0 (0) | 0 (0) |
| Perianal disease (n, %) | 1 (17) | 3 (43) | 2 (25) | 1 (14) | 2 (20) |

TABLE 2-continued

Demographic data for CD subjects included in the analyses.

| | Surgical Cohort (N = 6) | Colonoscopy Cohort (N = 7) | Biobank Colon (N = 8) | Biobank Ileum 1 (N = 7) | Biobank Ileum 2 (N = 10) |
|---|---|---|---|---|---|
| Disease phenotype (n, %) | | | | | |
| Nonstricturing-nonpenetrating (B1) | 0 (0) | 3 (43) | 1 (13) | 0 (0) | 0 (0) |
| Stricturing (B2) | 3 (50) | 1 (14) | 4 (50) | 3 (43) | 3 (30) |
| Penetrating (B3) | 3 (50) | 3 (43) | 3 (38) | 4 (57) | 7 (70) |
| Previous IBD surgery (n, %) | 4 (67) | 3 (43) | 3 (38) | 1 (14) | 2 (20) |
| Current medications (n, %) | | | | | |
| Antibiotics | 2 (33) | 2 (29) | 3 (38) | 1 (14) | 0 (0) |
| Systemic corticosteroids | 3 (50) | 2 (29) | 4 (50) | 1 (14) | 5 (50) |
| Aminosalicylate | 0 (0) | 1 (14) | 2 (25) | 1 (14) | 2 (20) |
| Immunomodulator | 2 (33) | 1 (14) | 3 (38) | 1 (14) | 1 (10) |
| Anti-TNF | 1 (17) | 2 (29) | 3 (38) | 2 (29) | 5 (50) |
| Vedolizumab | 2 (33) | 2 (29) | 0 (0) | 1 (14) | 0 (0) |
| Ustekinumab | 2 (33) | 0 (0) | 2 (25) | 3 (43) | 0 (0) |
| Previously failed anti-TNF (n, %) | 6 (100) | 4 (57) | 4 (50) | 5 (71) | 3 (30) |

IBD = Inflammatory bowel disease;
IQR = Interquartile range

Figure 11A:
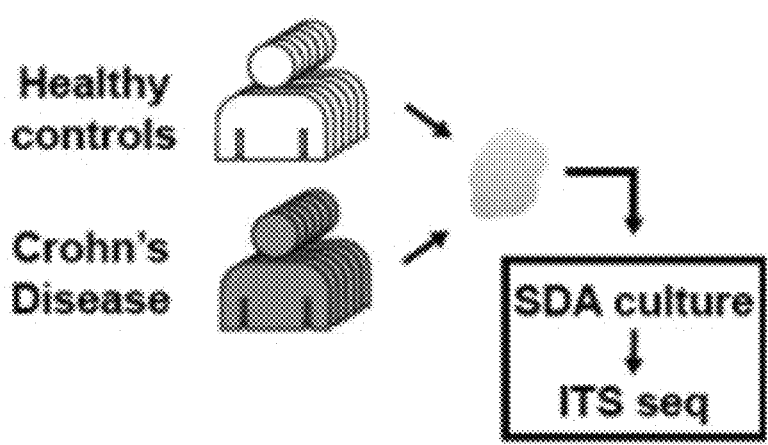
FIG. 11: *D. hansenii* was enriched in inflamed intestinal tissue of patients with CD and the human isolate impaired crypt regeneration in vivo. (A-B) Inflamed ileal biopsy tissue was collected from healthy individuals and CD patients, homogenized, and plated on SDA medium. (A) Schematic representation of the procedures and analysis. (B) Relative abundance of fungi growing in culture at the genus level as assessed by ITS sequencing of the pooled colonies growing per individual. The data is shown per patient (D) or healthy individual (H) on the x-axis and relative abundance of genus on the y-axis. (C-D) DNA was isolated from the inflamed and non-inflamed ileal regions of surgical resections obtained from CD patients and ITS amplicons were sequenced. (C) Schematic representation of the procedures and analysis. (D) Relative abundance of fungi at the genus level in inflamed and non-inflamed regions. Only genera with a combined mean across both groups of >1.5% relative abundance are plotted. All other genera are combined into "Other." (E) Intestinal tissue samples from the surgical cohort in 11C were homogenized and cultured on SDA plates. Relative abundance of genera of all viable colonies in the indicated samples identified by ITS sequencing of pooled colonies per sample. Data for relative abundance are broken down by individual samples (non-inflamed vs inflamed) on the x-axis. Fungi could be cultured from only one non-inflamed region whereas viable colonies were recovered from all inflamed tissues. (F) DNA was isolated from intestinal tissue; *D. hansenii* abundance was analyzed by qPCR and normalized to Gapdh DNA. Significance was determined by paired Student's t-test: *p<0.05 and **p<0.01. (G-I) SPF WT mice were gavaged with *D. hansenii* (obtained from CD tissue in (B)) in the presence or absence of amphotericin B (AmpB) and biopsy injured. (G) Schematic representation of the experiment. (H) Representative images of H&E stained sections (Bars=100 μm) and (I) wound bed length at day 12 post-injury from indicated groups of mice (n=14-17 wounds/group from 5-7 mice/group). Significance was determined by one-way ANOVA and TUKEY's post-hoc test: ****p<0.0001. All values in H are displayed as mean±SEM. The dashed black line in G at the center of the wound represents wound bed length (largest distance between the crypts).

In the colonoscopy cohort, ileal biopsy tissue was obtained from CD patients and healthy controls undergoing routine endoscopy as illustrated in FIG. 11A. These tissues were homogenized, streaked on SDA media, and subjected to ITS sequencing in a manner similar to the methods described above. In the surgical cohort, ITS sequencing was performed on genomic DNA isolated directly from ileal resection samples of CD patients.

Figure 11B:
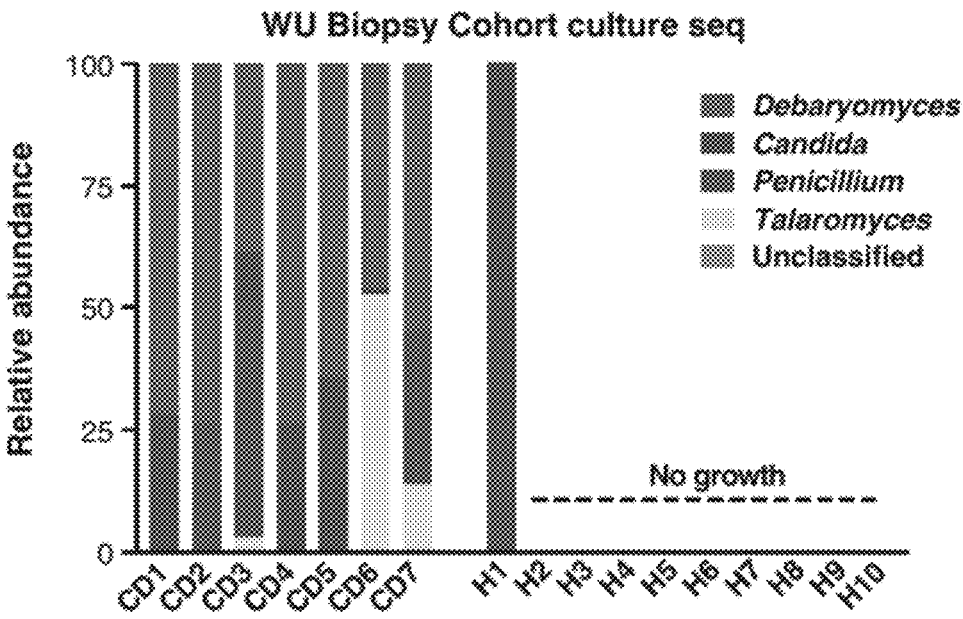
Figure 11C:
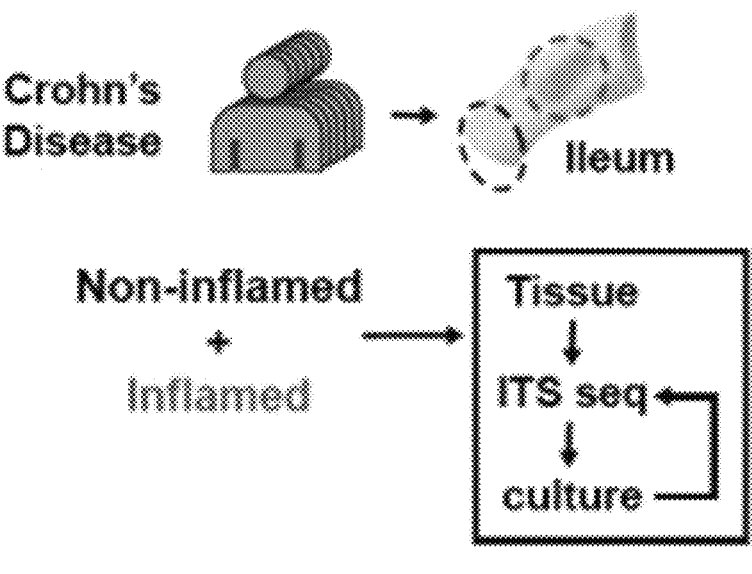
Figure 11D:
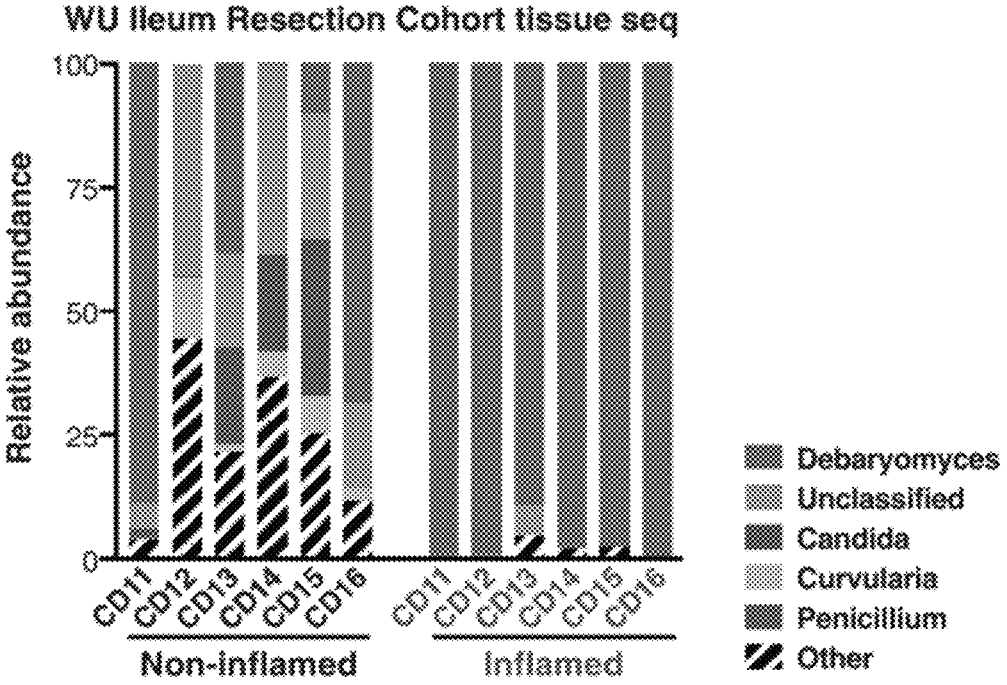
Figure 11E:
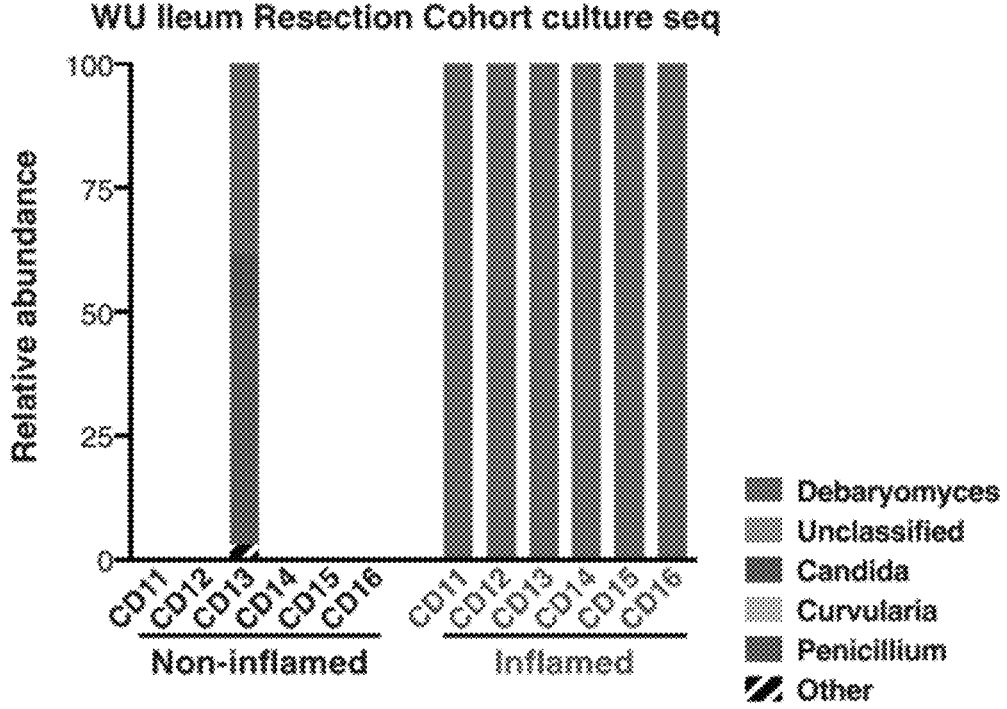

Fungi were present in all the homogenates from CD biopsy tissues but only one of ten healthy biopsy tissues (FIG. 11B). *Debaryomyces* was detected in all CD patient tissue samples as determined by ITS sequencing of pooled colonies (FIG. 11B). *Debaryomyces* was significantly enriched in inflamed regions compared to uninflamed regions from the same patient (FIG. 11C, D, and FIG. 29). Importantly, inflamed regions of CD tissue samples from surgical resections were highly enriched for culturable *Debaryomyces* (FIG. 11E). Despite detectable *Debaryomyces* sequencing reads in non-inflamed regions (FIG. 11D), viable fungi were not recovered in 5 out of 6 tissue samples.

Having confirmed the presence of *Debaryomyces* using two independent approaches, the analysis of CD samples from the surgical cohort was expanded using *D. hansenii* species-specific primers as described above.

Figure 11F:
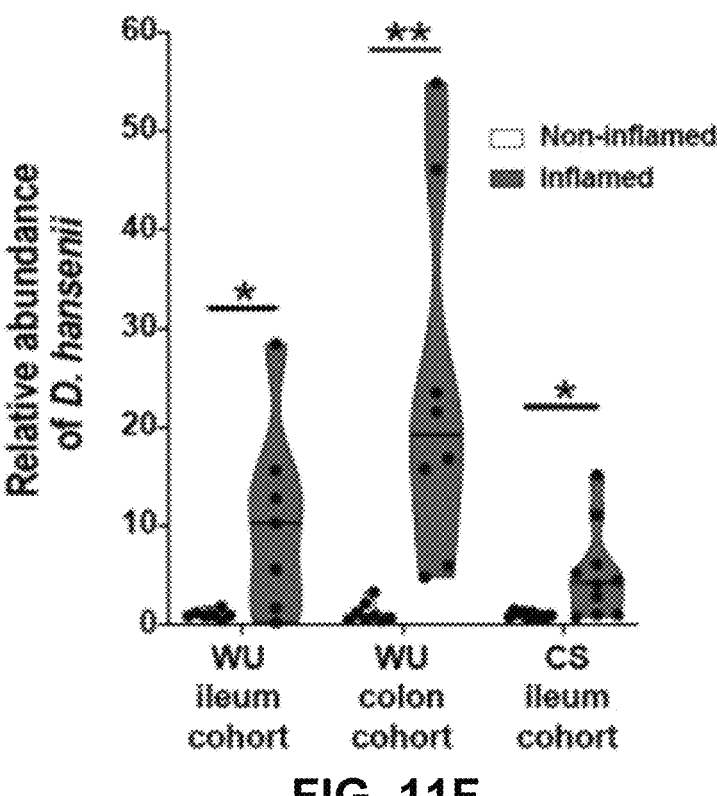

*D. hansenii* was significantly enriched in inflamed areas of both the ileum and colon as compared to respective uninflamed counterparts (FIG. 11F). In the Ileum2 cohort, *D. hansenii* demonstrated increased abundance in inflamed ileal tissue as compared to uninflamed ileal tissue from the same patient (FIG. 11F).

As serum antibodies directed against fungi have been associated with severe CD, the following experiment was conducted to test if antibodies in CD serum could recognize *D. hansenii*. A clinical isolate of *D. hansenii* (CDA1, Table 3) was subjected to 5 freeze-thaw cycles and sonication to obtain *D. hansenii* lysate. This lysate was used as a coating antigen in the ELISA assay. 96 well high binding plates were coated with the *D. hansenii* lysate overnight followed by 5 washes with the Wash Buffer (0.05% Tween 20 in PBS) and blocking nonspecific binding with 1% BSA for 2 hours. The plates were then washed and incubated with serum samples (1:1000 dilution) overnight at 4° C. Next, the plates were washed and incubated with HRP Goat anti-human IgA Antibody (BioLegend) for 30 minutes and developed using 1-step ultra TMB substrate (Thermo Fisher Scientific). The reaction was stopped with 2% sulphuric acid and read at 405 nm at Synergy (BioTek) microplate reader. All serum samples (healthy controls and CD subjects) were run on the same plate.

TABLE 3

Debaryomyces isolates obtained from inflamed CD tissue identified via ACT1 sequencing

| CD patient # | Isolate name | Identity |
|---|---|---|
| 1 | CDA1 | *Debaryomyces hansenii* |
| 2 | CDB1 | *Debaryomyces hansenii* |
| 2 | CDC1 | *Debaryomyces hansenii* |

IgA that recognized the CDA1 clinical isolate of *D. hansenii* (FIG. 30A) and CCL5 (FIG. 30B) was elevated in the serum of CD patients compared to healthy controls. In addition, the level of IgA showed a significant correlation with serum CCL5 levels (FIG. 30C).

Example 11: Repair Defects Induced by *Debaryomyces hansenii*

Figure 11G:
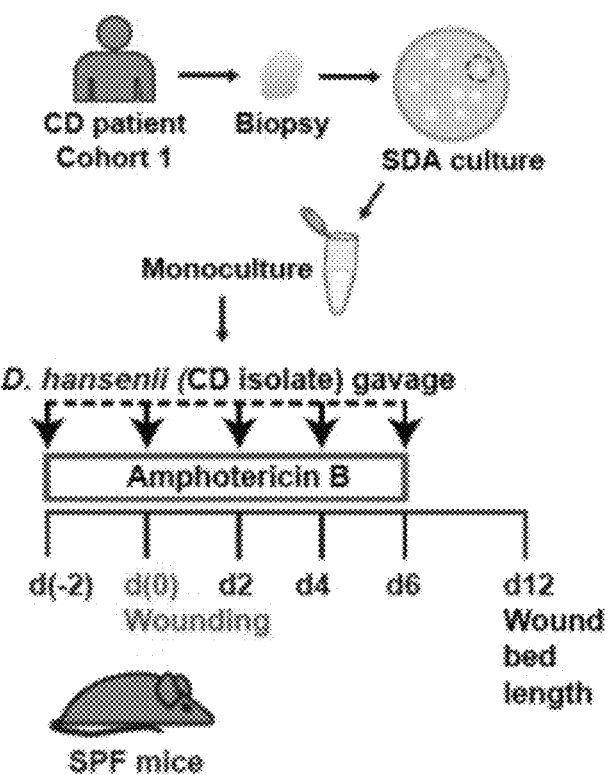
Figure 11H:
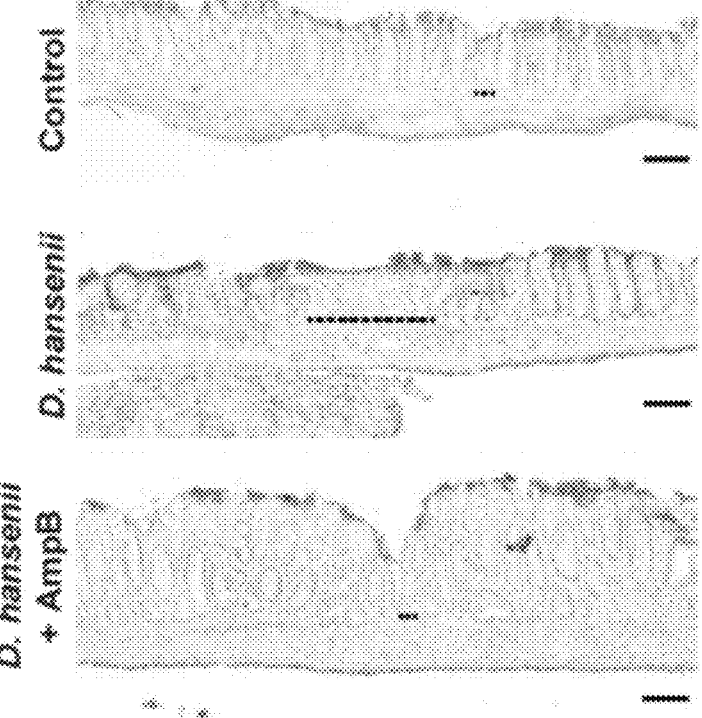
Figure 11I:
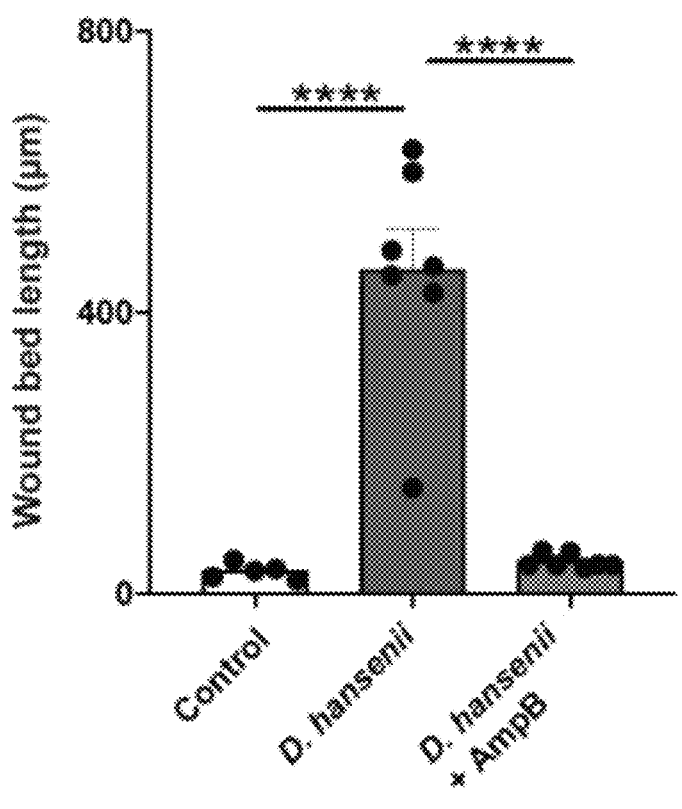
Figure 31:
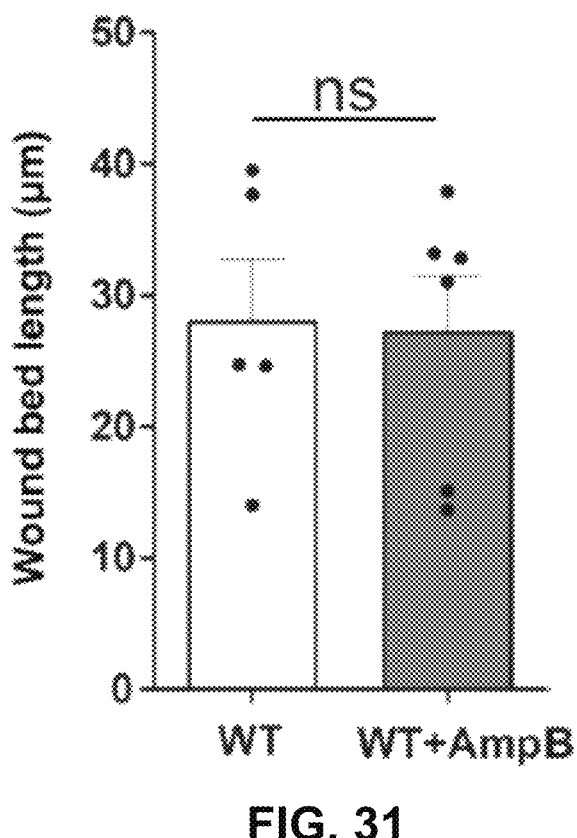
FIG. 31: Amphotericin B does not impact healing in WT mice. Wound bed length at day 12 post-injury in biopsy injured WT mice treated with or without amphotericin B (n=14-21 wounds from 5-6 mice per group). Significance was determined by unpaired Student's t-test. ns=not significant". Data are displayed as mean±SEM.

To ascertain whether human clinical isolates of *D. hansenii* were capable of inducing repair defects, the following experiments were conducted. WT mice were gavaged with *D. hansenii* CDA1 (Table 3) using methods similar to those described above. The CDA isolate was associated with impaired crypt regeneration in the biopsy injury model, and this effect was reversed by amphotericin B treatment (FIG. 11G, I). Further, administration of amphotericin B, in the absence of *D. hansenii* gavage, did not demonstrate any obvious defects in repair of WT mice (FIG. 31). Collectively these findings suggested that *D. hansenii* is enriched in inflamed tissues of individuals with CD and that the *D.*

*hansenii* isolates impair colonic repair in mouse models of colonic damage, suggesting that targeting this microbe could be a therapy for CD.

What is claimed is:

1. A method for treating Crohn's disease in a human patient with symptoms of Crohn's disease comprising:

a) detecting at least one of the following:

i) the presence of *Debaryomyces hansenii* deoxyribonucleic acid (DNA) sequences in a sample, or a culture thereof, obtained from said patient, wherein said sample comprises an inflamed intestinal biopsy sample, or an inflamed excised intestinal tissue sample, and ii) concentration of antibodies against *Debaryomyces hansenii* in a blood or serum sample obtained from said patient that is higher than the average concentration in a blood or serum sample obtained from healthy controls; and b) administering a therapeutically effective amount of an antifungal compound to the patient.

2. The method of claim 1, wherein the antifungal compound is administered to reduce levels of said *Debaryomyces hansenii* in the gut microbiome of the patient.

3. The method of claim 1, wherein the antifungal compound is selected from the group consisting of: fluconazole, caspofungin, flucytosine, and any combination thereof.

4. The method of claim 1, wherein said detecting comprises detecting the presence of said *Debaryomyces hansenii* DNA sequences.

5. The method of claim 1, wherein said detecting comprises detecting said concentration of antibodies against *Debaryomyces hansenii.*

* * * * *